US006653486B2

(12) United States Patent
Chappelow et al.

(10) Patent No.: US 6,653,486 B2
(45) Date of Patent: Nov. 25, 2003

(54) SPIROORTHOCARBONATES CONTAINING EPOXY GROUPS

(75) Inventors: Cecil C. Chappelow, Leawood, KS (US); Charles S. Pinzino, Kansas City, MO (US); J. David Eick, Gladstone, MO (US)

(73) Assignee: Curators of the University of Missouri, Columbia, MO (US)

( * ) Notice: Subject to any disclaimer, the term of this patent is extended or adjusted under 35 U.S.C. 154(b) by 0 days.

(21) Appl. No.: 10/234,551

(22) Filed: Sep. 4, 2002

(65) Prior Publication Data

US 2003/0119931 A1 Jun. 26, 2003

Related U.S. Application Data

(62) Division of application No. 09/232,500, filed on Jan. 15, 1999, now Pat. No. 6,458,865.

(51) Int. Cl.$^7$ .............................................. C07D 319/00

(52) U.S. Cl. ...................... 549/335; 549/334; 522/169; 526/268; 528/403; 528/406

(58) Field of Search .................. 522/169; 526/268; 528/403, 406; 549/335, 334

(56) References Cited

U.S. PATENT DOCUMENTS

| | | | |
|---|---|---|---|
| 4,368,314 A | * | 1/1983 | Endo |
| 4,387,215 A | * | 6/1983 | Bailey |
| 4,528,386 A | * | 7/1985 | Poshkus |
| 4,656,294 A | * | 4/1987 | Kanayama |
| 4,738,899 A | * | 4/1988 | Bluestein et al. |
| 4,851,550 A | * | 7/1989 | Mues et al. |
| 4,855,367 A | * | 8/1989 | Flury |
| 4,870,193 A | * | 9/1989 | Taguchi et al. |
| 4,876,323 A | * | 10/1989 | Engel et al. |
| 4,988,607 A | * | 1/1991 | Ali |
| 5,194,365 A | * | 3/1993 | Goodin et al. |
| 5,236,812 A | * | 8/1993 | Vassiliou et al. |
| 5,298,631 A | * | 3/1994 | Sanda et al. |
| 5,362,889 A | * | 11/1994 | Stansbury |
| 5,463,008 A | * | 10/1995 | Stansbury |
| 5,492,942 A | * | 2/1996 | Kobayashi et al. |
| 5,556,896 A | * | 9/1996 | Byerley et al. |
| 5,631,307 A | * | 5/1997 | Tanaka et al. |
| 5,798,396 A | * | 8/1998 | Takahashi et al. |
| 5,808,108 A | * | 9/1998 | Chappelow et al. |
| 5,877,232 A | * | 3/1999 | Storch et al. |
| 5,980,253 A | * | 11/1999 | Oxman et al. |
| 5,998,495 A | * | 12/1999 | Oxman et al. |

FOREIGN PATENT DOCUMENTS

| | | | |
|---|---|---|---|
| JP | 64726 | * | 4/1986 |
| WO | WO 96/13538 | * | 5/1996 |
| WO | WO 98/47046 | * | 10/1998 |
| WO | WO 98/47047 | * | 10/1998 |

OTHER PUBLICATIONS

Bailey, "Matrices that Expand on Curing for High Strength Composites and Adhesives," *Materials Science & Engineering*, A126, pp. 271–279, 1990.

Bailey et al., "Radical Ring–Opening Polymerization and Copolymerization with Expension in Volume," *Journal of Polymer Science: Polymer Symposium*, vol. 64, pp. 17–26, 1978.

Blomquist et al. "The Mineral Acid–catalyzed Reaction of Cyclohexene with Formaldehyde," *Acid–Catalyzed Reaction of Cyclohexene with Formaldehyde*, pp. 6025–6030, Nov. 20, 1957.

Byerley et al., "Expandable Matrix Monomers for Dental Composites," *Journal of Dental Research*, 69(SI), p. 263, Abstract No. 1233, Mar., 1990.

Byerley et al., "Expandable Matrix Monomers for Dental Composites," pp. 1–9, Mar. 1990.

Byerley et al., "Spiroorthocarbonates: Polymerization and Volume Change Determinations," *Journal of Dental Research*, 70(SI), p. 527, Abstract No. 2087, 1991.

DeWolfe, "Synthesis of Carboxylic and Carbonic Orthor Esters," pp. 153–172, Mar. 1974.

He et al., "Study on Copolymer Epoxy Resin Matrix without Shrinkage: Part 1 Volume Change During Cure Processes," *Chinese Journal of Polymer Science*, vol. 6, pp. 30–35, 1988.

He et al., "Epoxy Resin Copolymer with Zero Shrinkage, Part I Volume Change on Cure," *Journal of Material Science*, vol. 24, pp. 1528–1532, 1989.

He et al., "Epoxy Resin Copolymer with Zero Shrinkage, Part II Thermal and Mechanical Properties," *Journal of Material Science*, vol. 26, pp. 3792–3796, 1991.

He et al., *Chem. Abs.*, 109, Ab. #74464, 1989.

(List continued on next page.)

Primary Examiner—Susan W. Berman
(74) Attorney, Agent, or Firm—Stinson Morrison Hecker LLP

(57) ABSTRACT

Photopolymerizable compositions are provided which are the reaction products of a vinyl ether, a photoinitiator system comprising an iodonium salt, a visible light sensitizer, and an electron donor compound. These monomeric/oligomeric compositions may also include epoxides, polyols, spiroorthocarbonates. One embodiment of the present invention is a polymerizable composition comprised of a vinyl ether, a spiroorthocarbonate, and a photoinitiator system. Another embodiment of the present invention is a polymerizable composition comprised of a vinyl ether, an epoxide, a polyol, and a photoinitiator system. Still another embodiment of the present invention is a polymerizable composition comprised of a vinyl ether, an epoxide, a polyol, a spiroorthocarbonate, and a photoinitiator system.

Still further, another embodiment of the present invention is certain novel spiroorthocarbonate compounds. Each of these novel spiroorthocarbonate compounds include at least one epoxy group as a substituent.

2 Claims, 1 Drawing Sheet

OTHER PUBLICATIONS

Manzhen, "Photoinitiated Cationic Copolymerization of an Aiclyclic Epoxy Compound and a Spiroorthocarbonate," *International Journal of Polymeric Materials,* vol. 18, pp. 1–7, 1992.

Manzhen, "Effect of Structural Difference of Photoinitiator on Photocopolymerization of an Alicyclic Epoxy Compound and a Spiroorthocarbonate," *International Journal of Polymeric Materials,* vol. 18, pp. 189–195, 1992.

Millich et al., "Expansion Polymerization Density Change Determination," pp. 1–17.

Phillips, "Restorative Resins," *Science of Dental Materials,* 9th ed., pp. 215–233, 1991.

Stansbury et al., "Evaluation of Spiro Orthocarbonate Monomers Capable of Polymerization with Expansion as Ingredients in Dental Composite Materials", *Progress in Biomedical Polymers,* pp. 133–139, 1990.

Anderson et al., "A Simple Procedure for the Epoxidation of Acid–Sensitive Olefinic Compounds with m–Chloroperbenzoic Acid in an Alkaline Biphasic Solvent System," *Journal of Organic Chemistry,* vol. 38, pp. 2267–2268, 1973.

Bai et al., "Gaodeng Zueziao Huazue Zuebao", vol. 16, Abstract No. 123:258384, pp. 1487–1489, 1995.

Bailey et al., "Convenient Preparation of Trans–1,3–Dioxadecalin Via the Prins Reaction," *Synthetic Communications,* 17(15), pp. 1769–1772, 1987.

Bailey et al., "Recent Advances in Ionic Polymerization with Expansion in Volume," *Polymers Preprint,* vol. 26, pp. 50–51, 1985.

Brautigam et al., "New Vinyl Ether Oligomers and Diluent Monomers for Cationic Curing," *Vectomer™ 005R Vinyl Ether Oligomers and Monomers,* 6 pages, 1990.

Byerley et al., "Synthesis and Polymerization of New Expanding Dental Monomers," *Dental Materials,* vol. 8, pp. 345–350, Nov. 1992.

Chappell et al., "Density Determination and Volume Change Calculations for Monomer to Polymer," *Journal of Dental Research,* 75(SI), p. 462, Abstract No. 492, 1995.

Chappelow et al., "Design and Development of Isocyanatoacrylates as Dental Adhesives," *Journal of Dental Research,* 75(2), pp. 761–767, 1996.

Depres et al., "Improved Selectivity in the Preparation of Some 1,1–Difunctionalized 3–Cyclopentenes. High Yield Synthesis of 3–Cyclopentenecarboxylic Acid," *Journal of Organic Chemistry,* vol. 49, pp. 928–931, 1984.

Dougherty et al., "Vinyl Ethers for Cationic UV Curing," RADCURE '86 Conf. Proc. 10th, *Assoc. Finish Processes SME,* pp. 1–8, 1986.

Eick et al., "Photoreactivity of Vinyl Ether/Epoxy–Based Candidate Dental Adhesives," *Journal of Dental Research,* 77B, p. 639, Abstract 63, Jun. 24, 1998.

Eick et al., "Adhesives and Nonshrinking Dental Resins of the Future," *Journal of Dental Research,* 72(SI), p. 189, Abstract No. 685, 1993.

Eick et al., "Properties of Expanding SOC/Epoxy Copolymers for Dental Use," *Journal of Dental Research,* 71(SI), p. 598, Abstract No. 662, 1992.

Eick et al., "Properties of expanding SOC/Epoxy Copolymers for Dental Use in Dental Composites," *Dental Material,* vol. 9, pp. 123–127, Mar. 1993.

Eick et al., "Symposium: Dental Composites and Adhesives in the 21st Century—The Gunnar Ryge Memorial Symposium," *Journal of Dental Research,* 72(SI), p. 189, Abstract No. 682, 1993.

Endo et al., "Polymerization and Block Copolymerization Initiated by Unusually Stable Living Propagating Species Formed in the Cationic Polymerization of Spiro Ortho Carbonate," vol. 21, pp. 1186–1187, 1988.

Endo et al., "Synthesis and Cationic Polymerization of 3,9–Dibenzyl–1,5,7,11–tetraoxaspiro[5,5]undecane," *Macromolecules,* vol. 20, pp. 1416–1419, 1987.

Fujinami et al., "Effect of Substituents on Cationic Polymerization of Six–Membered Spiro Orthocarbonates," *Polymer Journal,* vol. 9, pp. 553–560, 1977.

Gharbi et al., "Condensation of Substituted Styrenes with Aliphatic and Aromatic Aldehydes; An Extension of the Prins Reaction," *A Communication to Synthesis,* 0039–7881/81/0532–0361, pp. 361–362, 1981.

Chappelow et al., "Development of Non–shrinking adhesive Composite Materials," Presented at the Dental Materials Symposium on Progress in– Dentin, Dentin Bonding, and Restorative Materials at the 27th Annual Meeting of the American Association for Dental Research, Minneapolis, Minnesota, Mar. 1998.

Chappelow et al., "Isocyanatoacrylate Copolymer Dental Adhesives—Priming and Crosslinking Systems," *Academy of Dental Materials,* vol. 9, p. 255, 1996.

Chappelow et al., "Photocured Epoxy/SOC Matrix Resin Systems for Dental Composites," *Polymer Preprints,* 38(2), p. 90, 1997.

Chappelow et al., "Photopolymerization of Epoxy/Polyol Mixtures Containing Spiroorthocarbonates," *Journal of Dental Research,* 76(SI), p. 40, 1997.

Chappelow et al., "Photoreactivity of Expanding Monomers in Dental Matrix Resins Systems," *Journal of Dental Research,* 77B, p. 639, Abstract No. 62, Jun. 24, 1998.

Chappelow et al., "Photoreactivity of Substituted 1,5,7,11–Tetraoxaspiro[5,5]undecane/Diepoxide/Poplyol Matrix Resin Systems," Presented at the 27th Annual Meeting of the American Association for Dental Research, Minneapolis, Minnesota, Mar. 1998.

Chappelow et al., "Synthesis and Photopolymerization of Substituted 1,5,7,11–Tetraoxaspiro[5,5]undecanes," *Journal of Dental Research,* 75(SI), p. 235, Abstract No. 492, 1995.

Cipollina et al., "Synthesis and Biological Activity of the Putative Metabolites of the Atypical Antipsychotic Agent Tiospirone," *Journal of Medical Chemistry,* vol. 34, pp. 3316–3328, 1991.

Corey et al., "A Mild Procedure for the Conversion of 1,2–Diols to Olefins," *Tetrahedron Letters,* vol. 23, pp. 1979–1982, 1982.

Delmas et al., "Selective Synthesis of 4–Aryl–1,3–cioxanes from Arylalkenes and Paraformaldehyde using an Ion Exchange Resin as Catalyst; Extension to Natural Compounds," *A Communication to Synthesis,* 0039–7881/80–1132–0871, pp. 871–872, 1980.

Delmas et al., "Supported Acid Catalysis with Ion–exchange Resins I. Role of Benzene as Solvent During the Prins Reaction," *Journal of Molecular Catalysis,* 4(1978), pp. 443–447, 1978.

Harris et al., "Hompolymerization of Spiroorthocarbonate: A Computational Study," *Journal of Dental Research,* 77(SI), p. 154, 1998.

Hellier et al., "Carbon–13 N.M.R. Studies of Stereoisomerism in a Spiro Carbonate," *Journal of Chemical Research,* (S), pp. 1388–1399, 1988.

Heslinga, "The Acetolysis of 4–Phenyl–1,3–Diozan. A New Synthesis of Cinnamyl Esters," *Recueil,* vol. 78, pp. 473–479, 1959; CA 54, 1403e, *Rec. Travl. Chim...*

Janzen et al., "Synthesis and Spin–Trapping Chemistry of 5,5–Dimethyl–2–(trifluoromethyl)–1–pyrroline N–Oxide," *Journal of Organic Chemistry,* vol. 60, pp. 5434–5440, 1995.

Kostoryz et al., "Reduced Cytotoxicity of New Dental Resins Containing Spiroorthocarbonate/Epoxy Copolymers," *Journal of Dental Research,* 76(SI), p. 321, 1997.

Krapcho et al., "2–Carbethoxyclyclooctanone," *Organic Syntheses,* vol. 47, pp. 20–23, 1967.

"Aliphatic Nucleophilic Substitution," *Advanced Organic Chemistry,* 4th Ed., pp. 392–393, Mar. 1992.

"Photopolylmerization Test Procedure—Visible Light photolysis using Photo–DSC Technique," *Epoxy Resins Chemistry and Technology,* May 1988.

Millich et al., "Determination of Density Changes with Expansion Polymerization," *Journal of Polymer Science: Part B: Polymer Physics,* vol. 31, pp. 729–733, 1993.

Penny et al., "Phenyl Phosphorodichloridate in the Synthesis of Cyclic Phosphate Diesters of Biological Interest," *Canadian Journal of Chemistry,* vol. 56, pp. 2396–2404, 1978.

Pinzino et al., "Visible Light Inducted Polymerization Studies of SOCs and Monofunctional Epoxides," *Journal of Dental Research,* 76(SI), p. 41, 1997.

Power et al., "Photoinitiated Polymerization of Isocyanatoacrylates as Dental Adhesives," *Journal of Dental Research,* 76(SI), p. 257, 1997.

Power et al., Visible Light Cured Isocyanatoacrylate Base Dental Adhesives, *Polymer Preprints,* 38(2), p. 145, 1997.

Rose et al., "A Study of the Mutagenicity of Non–Shrinking Spiroorthocarbonate Co–Polymers," *Journal of Dental Research,* 75(SI), p. 329, Abstract No. 2492, 1996.

Sadhir et al., Expanding Monomers Synthesis, Characterization, and Applications, *CRC Press,* 1992; pp. 329–332.

Sakai et al., "Reaction of Dialkyltin Dialkoxides with Carbon Disulfide at Higher Temperature. Preparation of Orthocarbonates," *Journal of Organic Chemistry,* vol. 36, pp. 1176–1180, 1971.

Soai et al., "A Chemoselective One–Step Reduction of β–Ketoesters to 1,3–Diols," _*Syntheses Communications,* pp. 605–607, 1984.

Stansbury et al., "Evaluation of Spiro Orthocarbonate Monomers Capable of Polymerization with Expansion as Ingredients in Dental Composite Materials," *Polymeric Material Science and Engineering,* vol. 59 pp. 402–406, 1988.

Stansbury, "Improved Monomers for Double Ring–Opening Polymerization with Expansion," *Journal of Dental Research,* vol. 70, p. 527, Abstract No. 2088, 1991.

Thompson et al., Dental Resins with Reduced Shrinkage During Hardening, *Journal of Dental Research,* vol. 58, pp. 1522–1532, 1979.

Uchida et al., "The Prins Reaction of Cyclooctene and Cyclododecene," *Bulletin of the Chemical Society of Japan,* vol. 46, pp. 2512–2515, 1973.

Yano et al., "Activation and Control of the Reaction of Dioxastannolane with Carbon Disulfide and Phenyl Isothiocyanate by the Addition of Bases," *Chem. Ber.,* vol. 124, pp. 1881–1884, 1991.

Yourtee et al., "The Effect of Spiroorthocarbonate Volume Modifier Co–monomers on the In Vitro Toxicology of Trial Non–shrinking Dental Expoxy Co–polymers," *Research Communications in Molecular Pathology and Pharmacology,* vol. 86, pp. 347–360, Dec. 1994.

Zhuang et al., "Evaluation of a Tetrazolium Colorimetric Test for Biomaterial Cytotoxicity Determination," *Journal of Dental Research,* 72(SI), p. 162, Abstract No. 469, 1993.

BASF, Vinyl Ethers, The Innovative Challenge Brochure, 2 pages, no date indicated.

Allied Signal Inc., Vectomer™ 2010 Brochure, 1 page, 1990.

Allied Signal Inc., Vectomer™ 2015 Brochure, 1 page, 1990.

Allied Signal Inc., Vectomer™ 2020 Brochure, 1 page, 1990.

Allied Signal Inc., Vectomer™ 4010 Brochure, 1 page, 1990.

Allied Signal Inc., Vectomer™ 4020 Brochure, 1 page, 1990.

"Rapi–Cure—Vinyl Ethers Reactivity Agents for Radiation Curing Systems," *International Specialty Products,* 21 pages, no date indicated.

* cited by examiner

SPIROORTHOCARBONATES CONTAINING EPOXY GROUPS

CROSS-REFERENCE TO RELATED APPLICATIONS

This application is a Divisional of U.S. patent application Ser. No. 09/232,500, filed on Jan. 15, 1999, now U.S. Pat. No. 6,458,865, which is hereby incorporated herein by reference.

STATEMENT REGARDING FEDERALLY SPONSORED RESEARCH OR DEVELOPMENT

The government has certain rights in this invention.

FIELD OF THE INVENTION

This invention relates in general to compositions of matter and, more particularly, to compositions that include a vinyl ether and a photoinitiator system. These compositions may also include an epoxide, a polyol, and/or a spiroorthocarbonate (SOC), which may be one of the novel spiroorthocarbonates disclosed herein. The polymerizable compositions of the present invention are useful for a variety of applications, including for use as dental materials such as adhesives and composites.

BACKGROUND OF THE INVENTION

Many types of monomers undergo shrinkage during polymerization to a degree that makes them generally unsuited for use in numerous applications, including for use as stress-free composites, high-strength adhesives, and precision castings. As an example, when such monomers are used in composites which contain inorganic fillers, the polymeric matrix is subject to failure when the polymer shrinks and pulls away from the filler particles. Failure of the composite can also occur when the matrix ruptures as a result of voids or micro cracks which form in the matrix during polymerization shrinkage.

Polymeric matrices commonly employed in dental materials such as adhesives and composites are based on 2,2'-bis[4-(2-hydroxy-3-methacryloyloxypropoxy)]phenyl propane (BisGMA). A significant problem associated with the use of this monomer in dental applications is the shrinkage which occurs as the monomer is polymerized. The BisGMA monomer itself typically experiences high shrinkage, and when a low viscosity reactive diluent is combined with the monomer, the shrinkage may even be higher. The adverse effects of such shrinkage are believed to include increased postoperative sensitivity, the formation of marginal gaps between the dental restoration and the cavity wall, cracking of the restoration, and microleakage and potential failure of the restoration.

The discovery that spiroorthocarbonates may undergo reduced polymerization contraction and possibly polymerization expansion has led to the suggestion of their use in reinforced composites, including as dental materials. Spiroorthocarbonates are esters of orthocarboxylic acid and have four oxygen atoms bonded to a single carbon atom, with the carbon atom being common to two ring systems. The expansion of the spiroorthocarbonates on polymerization is attributed to a double spiro-cyclic ring opening of the spiroorthocarbonates, resulting in the breaking of two covalent bonds to form one new bond.

Initial attempts to form a homogeneous polymer matrix from certain spiroorthocarbonates and BisGMA resin mixtures proved unsuccessful because of the incomplete polymerization of the spiroorthocarbonates. Thompson et al., J. Dental Research 58:15221532 (1979). More recent studies demonstrated that homogeneous mixtures of other spiroorthocarbonates and BisGMA could be obtained. Stansbury, J. Dental Research 70:527; Abstract No. 2088(1991).

The photocationic-initiated expansion polymerization of alicyclic spiroorthocarbonate monomers and the potential use of the resulting polymers in dental materials have been previously reported by some of the present inventors, with others. Byerley et al., Dent. Mater. 8:345–350 (1992). The specific spiroorthocarbonates identified by Byerley et al. include cis/cis, cis/trans, and trans/trans configurational isomers of 2,3,8,9-di(tetramethylene)-1,5,7,11-tetraoxaspiro [5.5] undecane. These spiroorthocarbonates were determined to undergo an expansion of 3.5% during homopolymerization and demonstrated acceptable cytotoxicity and genotoxicity properties, making them promising components of composite resin matrix materials.

Some of the present inventors, with others, have also previously reported on the preparation of a copolymer of an alicyclic spiroorthocarbonate and an unidentified monofunctional epoxide, with the observation that there were no indications of the formation of small ring compounds as polymerization by-products. Byerley et al., J. Dental Research 69:263; Abstract No. 1233 (1990). The copolymerization of trans/trans-2,3,8,9-di(tetramethylene)-1,5,7,11-tetraoxaspiro[5.5]undecane and commercially available multifunctional epoxides was also disclosed in a paper presented by Byerley et al., Abstract No. 1233, cited above. However, no physical or mechanical properties, including percentage shrinkage, of the copolymer compositions were disclosed. Still further, spiroorthocarbonate copolymers have been created that are capable of yielding a hard, non-shrinking matrix resin. These copolymers include a trans/trans-2,3,8,9-di(tetramethylene)-1,5,7,11-tetraoxaspiro[5.5]undecane spiroorthocarbonate, a polymerizable epoxy resin, and a hydroxyl containing material, as described in U.S. Pat. No. 5,808,108.

A polymeric composition that includes a vinyl ether, a diepoxide, a polyol, and a photoinitiator system including an iodonium salt and a visible light sensitizer has previously been disclosed by one of the present inventors. Eick et al., J. Dental Research, 77B:639; Abstract No. 63 (1998). This photoinitiator system is similar to that disclosed in PCT/US95/14098, but does not utilize an electron donor compound. The reaction rate for forming this disclosed polymeric composition has subsequently been determined to be very slow, making the composition generally unsuited for use in applications requiring faster reaction rates.

An epoxide/polyol polymeric composition that includes a photoinitiator system comprising an iodonium salt, a visible light sensitizer, and an electron donor compound is disclosed by one of the present inventors, with another, in PCT application Nos. PCT/US98/04458 ('458 application) and PCT/US98/04029 ('029 application). The '458 application further suggests that other cationically polymerizable polymers, such as vinyl ethers, can be incorporated into the epoxide/polyol polymeric composition. However, this application does not suggest that vinyl ether may be a substantial component of the composition, but only an optional additive.

The results of an attempted block polymerization of a living poly (spiroorthocarbonate) and a vinyl ether are disclosed by T. Endo et al. in Macromolecules, vol. 21, pp. 1186–1187, in an article entitled "Polymerization and Block Copolymerization Initiated by Unusually Stable Living Propagating Species Formed in the Cationic Polymerization of Spiro Ortho Carbonate" (1988). The disclosed reactions required heat and a considerable amount of time for polymerization. In addition, homopolymerization of n-butyl vinyl ether was observed. This article does not disclose using a ternary photoinitiator system to promote polymerization.

A diepoxy spiroorthocarbonate, namely, 3,23-dioxatrispiro[tricyclo[3.2.1.0<2,4>]octane-6,5'-1,3-dioxane-2'2"-1,3-dioxane-5",7'"-tricyclo[3.2.1.0<2,4>octane], is disclosed in a book entitled, "Expanding Monomers, Synthesis, Characterization and Applications," edited by R. J. Sadhir and R. M. Luck, CRC Press, Boca Raton (1992), pp. 329–332. This compound is purported to have the following structure:

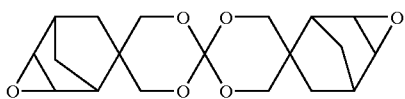

The book does not suggest that vinyl ethers may be combined with this spiroorthocarbonate, and the polymerization of the compound is reported to require extended reaction times and high temperatures (i.e., 1 hr/110° C., 1 hr/125° C., 4 hr/150° C., and 8 hr/150° C.). The disclosed polymerizations involved using a cationic initiator, but there is no suggestion that a visible light photoinitiator system could be used. The extended reaction times, elevated temperatures, and reaction conditions make the disclosed polymerizable composition generally unsuited for many applications, including use as dental materials.

Despite the advances resulting from the above-noted polymeric compositions and SOCs, a need still exists for polymerizable compositions having properties desirable for use as dental materials such as adhesives and composites, as well as other applications.

SUMMARY OF THE INVENTION

In one aspect, the present invention is directed to a photopolymerizable composition comprising a substantial amount of a vinyl ether, and a photoinitiator system that includes an iodonium salt, a visible light sensitizer, and an electron donor compound. The photoinitiator system has a photoinduced potential greater than or equal to that of N,N-dimethylaniline in a standard solution of $2.9 \times 10^{-5}$ moles/g diphenyl iodonium hexafluoroantimonate and $1.5 \times 10^{-5}$ moles/g camphorquinone in 2-butanone. The composition of the invention produces a polymerized product by subjecting the composition to conditions suitable for causing polymerization of the vinyl ether. The composition may further include an epoxide, a polyol, and/or one or more compounds represented by formula I below:

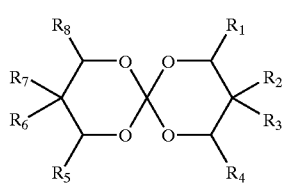

(I)

wherein $R_1$–$R_8$ are independently selected from the group consisting of hydrogen; alkyl; aryl; substituted alkyl; substituted aryl; 6-oxabicyclo[3.1.0]hex-2-yl; 6-oxabicyclo[3.1.0]hex-3-yl; (6-oxabicyclo[3.1.0]hex-2-yl)methyl; (6-oxabicyclo[3.1.0]hex-3-yl)methyl; (6-oxabicyclo[3.1.0]hex-2-yl)methoxy; (6-oxabicyclo[3.1.0]hex-3-yl)methoxy; 7-oxabicyclo[4.1.0]hept-2-yl; 7-oxabicyclo[4.1.0]hept-3-yl; (7-oxabicyclo[4.1.0]hept-2-yl)methyl; (7-oxabicyclo[4.1.0]hept-3-yl)methyl; (7-oxabicyclo[4.1.0]hept-2-yl)methoxy; (7-oxabicyclo[4.1.0]hept-3-yl)methoxy; and —(CH$_2$)$_n$—O—(O=C)—R$_9$, where n=1 through 9 and R$_9$=H, alkyl, aryl, substituted alkyl or substituted aryl, or $R_1 \cdot R_2$, $R_2 \cdot R_3$, $R_5 \cdot R_6$, and $R_6 \cdot R_7$ are independently selected from the group consisting of —CH$_2$(CH$_2$)$_n$CH$_2$— where n=3, 4, 5, and 6; —CH$_2$-epoxy-(CH$_2$)$_n$—CH$_2$— where n=0, 1, and 2; and —O— so as to form an alicyclic ring or an oxirane ring between R$_1$ and R$_2$, R$_2$ and R$_3$, R$_5$ and R$_6$, and R$_6$ and R$_7$, provided that R$_3$, R4, R$_7$, and R$_8$ are hydrogen when R$_1$•R$_2$ and R$_5$•R6 are independently selected from the group consisting of —CH$_2$(CH$_2$)$_n$CH$_2$— where n=3, 4, 5 and 6 so as to form an alicyclic ring between R$_1$ and R$_2$ and between R$_5$ and R$_6$;

R$_2$, R$_3$, R$_4$, R$_6$, R$_7$, and R$_8$ are hydrogen when R$_1$ and R$_5$ are independently selected from the group consisting of alkyl, aryl, substituted alkyl, and substituted aryl;

R$_1$, R$_4$, R$_5$, and R$_8$ are hydrogen when R$_2$ and R$_8$ are independently selected from the group consisting of alkyl, aryl, substituted alkyl, and substituted aryl and R$_3$ and R$_7$ are independently selected from the group consisting of —(CH$_2$)$_n$—O—(O=C)—R$_9$ where n=1 and 2 and R$_9$=H, alkyl, aryl, substituted alkyl or substituted aryl;

R$_1$, R$_4$, R$_5$, and R$_8$ are hydrogen when R$_2$ and R$_3$ are independently selected from the group consisting of H, alkyl, aryl, substituted alkyl, and substituted aryl and R$_6$•R$_7$=—CH$_2$-epoxy-(CH$_2$)$_n$—CH$_2$— where n=0, 1, and 2 so as to form an alicyclic ring between R$_6$ and R$_7$;

R$_1$, R$_4$, R$_5$, and R$_8$ are hydrogen when R$_2$•R$_3$ and R$_6$•R$_7$ are independently selected from the group consisting of —CH$_2$-epoxy-(CH$_2$)$_n$—CH$_2$— where n=0, 1, and 2 so as to form an alicyclic ring between R$_2$ and R$_3$ and between R$_6$ and R$_7$;

R$_1$, R$_4$, R$_5$, and R$_8$ are hydrogen when R$_2$ is independently selected from the group consisting of 6-oxabicyclo [3.1.0]hex-2-yl, 6-oxabicyclo[3.1.0]hex-3-yl, (6-oxabicyclo[3.1.0]hex-2-yl)methyl, (6-oxabicyclo[3.1.0]hex-3-yl)methyl, (6-oxabicyclo[3.1.0]hex-2-yl)methoxy, (6-oxabicyclo[3.1.0]hex-3-yl)methoxy, 7-oxabicyclo[4.1.0]hept-2-yl, 7-oxabicyclo[4.1.0]hept-3-yl, (7-oxabicyclo[4.1.0]hept-2-yl)methyl, (7-oxabicyclo[4.1.0]hept-3-yl)methyl, (7-oxabicyclo[4.1.0]hept-2-yl)methoxy, and (7-oxabicyclo[4.1.0]hept-3-yl)methoxy, and R$_3$, R$_6$, and R$_7$ are independently selected from the group consisting of hydrogen, alkyl, aryl, substituted alkyl, and substituted aryl;

R$_1$, R$_4$, R$_5$, and R$_8$ are hydrogen when R$_2$ and R$_3$ are independently selected from the group consisting of 6-oxabicyclo[3.1.0]hex-2-yl, 6-oxabicyclo[3.1.0]hex-3-yl, (6-oxabicyclo[3.1.0]hex-2-yl)methyl, (6-oxabicyclo[3.1.0]hex-3-yl)methyl, (6-oxabicyclo[3.1.0]hex-2-yl)methoxy, (6-oxabicyclo[3.1.0]hex-3-yl)methoxy, 7-oxabicyclo[4.1.0]hept-2-yl, 7-oxabicyclo[4.1.0]hept-3-yl, (7-oxabicyclo[4.1.0]hept-2-yl)methyl, (7-oxabicyclo[4.1.0]hept-3-yl)methyl, (7-oxabicyclo[4.1.0]hept-2-yl)methoxy, and (7-oxabicyclo[4.1.0]hept-3-yl)methoxy, and R$_3$ and R$_7$ are independently selected from the group consisting of hydrogen, alkyl, aryl, substituted alkyl, and substituted aryl;

$R_3$, $R_4$, $R_5$, $R_6$, $R_7$, and $R_8$ are independently selected from the group consisting of the group consisting of hydrogen, alkyl, aryl, substituted alkyl, and substituted aryl, when $R_1 \cdot R_2 =$—O— so as to form an oxirane ring between $R_1$ and $R_2$; and $R_3$, $R_4$, $R_7$, and $R_8$ are independently selected from the group consisting of hydrogen, alkyl, aryl, substituted alkyl, and substituted aryl, when $R_1 \cdot R_2$ and $R_5 \cdot R_6 =$—O— so as to form an oxirane ring between $R_1$ and $R_2$ and between $R_5$ and $R_6$. As used herein, alkyl refers to groups having 1 to 12 carbon atoms, preferably 1 to 10 carbon atoms, and more preferably 1 to 8 carbon atoms. The term "SOC" is used herein to refer to spiroorthocarbonates. When a spiroorthocarbonate is used in the polymerizable composition, the composition is particular useful as a dental material such as an adhesive or a composite, with the reaction product forming a matrix in which nonreactive dental fillers may be dispersed.

Another aspect of the present invention is directed to certain novel spiroorthocarbonates of formula (I) that contain epoxy groups. Namely, the invention includes the compounds 5,5-diethyl-19-oxadispiro[1,3-dioxane-2,2'-1,3-dioxane-5'4"-bicyclo[4.1.0]heptane](DECHE), 7,26-dioxatrispiro[bicyclo[4.1.0]heptane-4,5'-1,3-dioxane-2'2"-1,3-dioxane-5",4"-bicyclo[4.1.0]heptane] (DCHE), 5-5-diethyl-18-oxadispiro[1,3-dioxane-2,2'-1,3-dioxane-5',4"-bicyclo[3.1.0]hexane] (DECPE), 6,24-dioxatrispiro[bicyclo[3.1.0]hexane-3,5'-1,3-dioxane-2'2"-1,3-dioxane-5"3'"-bicyclo[3.1.0]hexane] (DCPE), 3,3-diethyl-1,5,7,11-tetraoxa-9-[(6-oxabicyclo[3.1.0]hex-3-yl)methoxy]spiro[5.5]undecane, 3,9-bis[(6-oxabicyclo[3.1.0]hex-3-yl)methoxy]-3-ethyl-1,5,7,11-tetraoxaspiro[5.5]undecane, 3,3-diethyl-1,5,7,11-tetraoxa-9-[(6-oxabicyclo[3.1.0]hex-2-yl)methoxy]spiro[5.5]undecane, 3,9-bis[(6-oxabicyclo[3.1.0]hex-2-yl)methoxy]-3-ethyl-1,5,7,11-tetraoxaspiro[5.5]undecane, 3,3-diethyl-1,5,7,11-tetraoxa-9-[(6-oxabicyclo[3.1.0]hex-3-yl)methyl]spiro[5.5]undecane,3,9-bis[(6-oxabicyclo[3.1.0]hex-2-yl)methyl]-3-ethyl-1,5,7,11-tetraoxaspiro[5.5]undecane, 3,3-diethyl-1,5,7,11-tetraoxa-9-[(6-oxabicyclo[3.1.0]hex-2-yl)methyl]spiro[5.5]undecane, 3,9-bis[(6-oxabicyclo[3.1.0]hex-2-yl)methyl]-3-ethyl-1,5,7,11-tetraoxaspiro[5.5S]undecane, 3,3-diethyl-1,5,7,11-tetraoxa-9-[(7-oxabicyclo[4.1.0]hept-3-yl)methyl]spiro[5.5]undecane, 3,9-bis[7-oxabicyclo[4.1.0]hept-3-yl)methyl]-3-ethyl-1,5,7,11-tetraoxaspiro[5.5]undecane, 3,3-diethyl-1,5,7,11-tetraoxa-9-[(7-oxabicyclo[4.1.0]hept-2-yl)methyl]spiro[5.5]undecane, 3,9-bis[7-oxabicyclo[4.1.0]hept-2-yl)methyl]-3-ethyl-1,5,7,11-tetraoxaspiro[5.5]undecane, 3,3-diethyl-1,5,7,11-tetraoxa-9-[(6-oxabicyclo[3.1.0]hex-3-yl)spiro[5.5]undecane, 3,9-bis[6-oxabicyclo[3.1.0]hex-3-yl)-3-ethyl-1,5,7,11-tetraoxaspiro[5.5]undecane, 3,3-diethyl-1,5,7,11-tetraoxa-9-[(6-oxabicyclo[3.1.0]hex-2-yl)spiro[5.5]undecane, 3,9-bis[6-oxabicyclo[3.1.0]hex-2-yl)-3-ethyl-1,5,7,11-tetraoxaspiro[5.5]undecane, 3,9-bis[7-oxabicyclo[3.1.0]hex-3-yl)-3-ethyl-1,5,7,11-tetraoxaspiro[5.5]undecane, 3,3-diethyl-1,5,7,11-tetraoxa-9-[(7-oxabicyclo[3.1.0]hex-3-yl)spiro[5.5]undecane, 3,9-bis[7-oxabicyclo[3.1.0]hex-3-yl)-3-ethyl-1,5,7,11-tetraoxaspiro[5.5]undecane, 3,3-diethyl-1,5,7,11-tetraoxa-9-[(7-oxabicyclo[3.1.0]hex-2-yl)spiro[5.5]undecane, 2,4,7,9,11,14-hexaoxaspiro[bicyclo[4.1.0]heptane-3,3'bicyclo[4.1.0]heptane], 8,10,13-trioxaspiro[1,3-dioxane-2,3'-bicyclo[4.1.0]heptane], 5,12-diemthyl-2,4,7,9.11,14-hexaoxaspiro[bicyclo[4.1.0]heptane-3,3'bicyclo[4.1.0]heptane], 4,5,5,11-tetramethyl-8,10-13-trioxaspiro[1,3-dioxane-2,3'-bicyclo[4.1.0]heptane], and 1,5,7,11-tetraoxaspiro[5.5]undecane.

BRIEF DESCRIPTION OF THE DRAWING

In the accompanying drawing which forms a part of the specification and is to be read in conjunction therewith.

DESCRIPTION OF THE PREFERRED EMBODIMENTS

Figure 1:
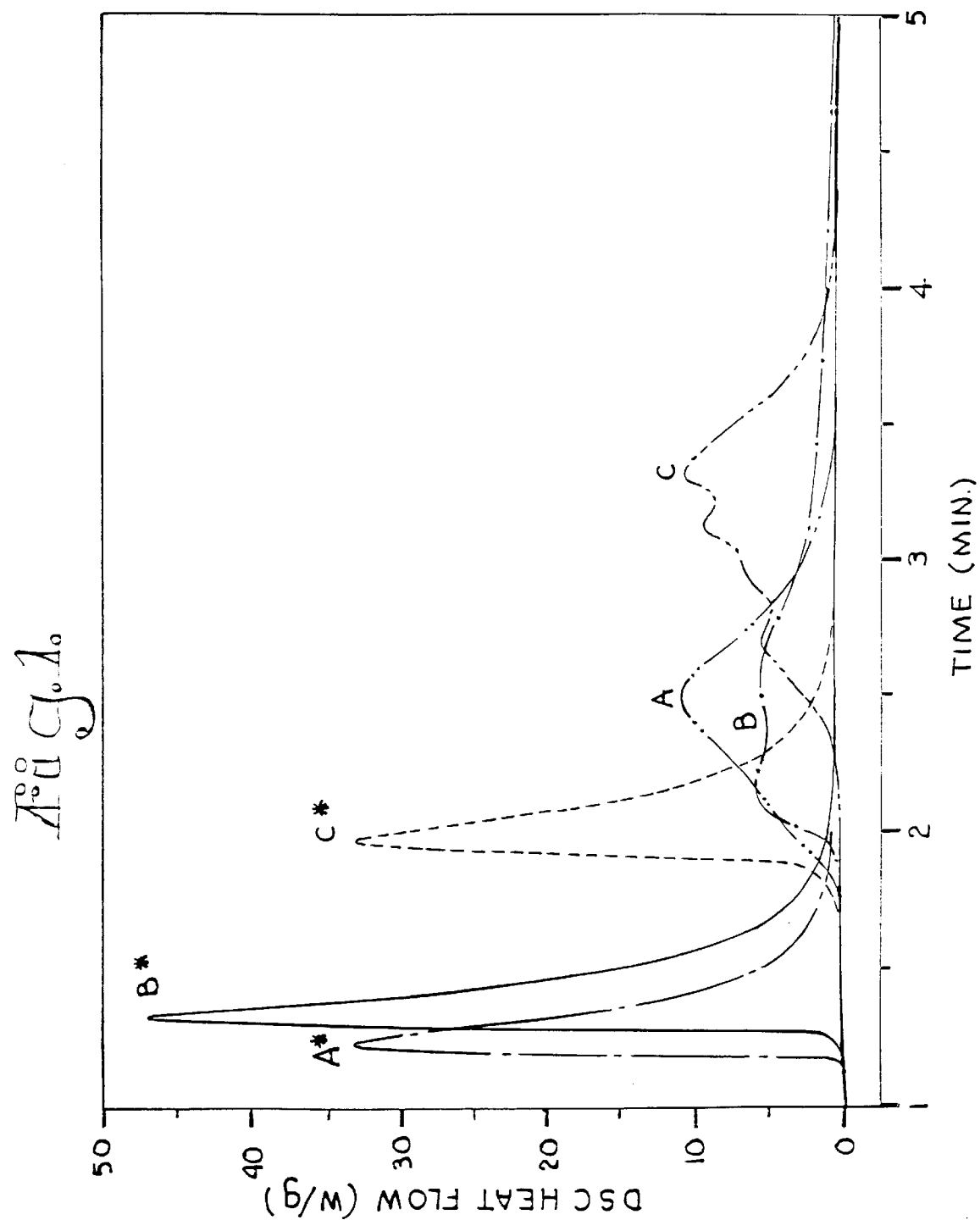
FIG. 1 is a graph showing the effect of an electron donor compound on the photohomopolymerization of vinyl ethers.

One aspect of the present invention is directed to a polymerizable composition comprising one or more vinyl ethers (VE) and a ternary photoinitiator system. The composition results in a polymerized product when the one or more vinyl ethers are contacted with the ternary photoinitiator system under conditions sufficient to promote polymerization of the vinyl ether. The polymerizable composition may also include an epoxy compound, an optional polyol, and an optional spiroorthocarbonate (SOC). Preferably, when an epoxy compound is included in the vinyl ether-based composition of the present invention, a polyol is also included as part of the composition. However, this need not be the case, and an epoxy compound may be included when a polyol is not included. In another embodiment, the polymerizable composition includes vinyl ether, an SOC, and the ternary photoinitiator system. In a further embodiment, the polymerizable composition includes vinyl ether, an epoxy compound, a polyol and the ternary photoinitiator system. Still another embodiment of the present invention is a polymerizable composition that includes vinyl ether, an SOC, an epoxy compound, a polyol and the ternary photoinitiator system.

Any cationically reactive vinyl ether may be used in polymerizable compositions of the present invention. Examples of vinyl ethers that may be used include, but are not limited to, tri(ethylene glycol)divinyl ether (TEGDVE), glycidyl vinyl ether (GVE), butanediol vinyl ether (BDVE), di(ethylene glycol)divinyl ether (DEGDVE), 1,4-cyclohexanedimethanol divinyl ether (CHDMDVE), 4-(1-propenyloxymethyl)-1,3-dioxolan-2-one (POMDO), 2-chloroethyl vinyl ether (CEVE), or 2-ethylhexyl vinyl ether (EHVE), ethyl vinyl ether (EVE), n-propyl vinyl ether (NPVE), isopropyl vinyl ether (IPVE), n-butyl vinyl ether (NBVE), isobutyl vinyl ether (IBVE), octadecyl vinyl ether (ODVE), cyclohexyl vinyl ether (CVE), butanediol divinyl ether (BDDVE), hydroxybutyl vinyl ether (HBVE), cyclohexanedimethanol monovinyl ether (CHMVE), tert-butyl vinyl ether (TBVE), tert-amyl vinyl ether (TAVE), dodecyl vinyl ether (DDVE), ethylene glycol divinyl ether (EGDVE), ethylene glycol monovinyl ether (EGMVE), hexanediol divinyl ether (HDDVE), hexanediol monovinyl ether (HDMVE), diethylene glycol monovinyl ether (MVE-2), triethyleneglycol methyl vinyl ether (MTGVE), tetraethylene glycol divinyl ether (DVE-4), trimethylolpropane trivinyl ether (TMPTVE), aminopropyl vinyl ether (APVE), poly-tetrahydrofuran divinyl ether (PTHFDVE), pluriol-E200 divinyl ether (PEG200-DVE), n-butyl vinyl ether (n-BVE), 4-hydroxybutylvinylether (HBVE), ethylene glycol butyl vinyl ether (EGBVE), 2-diethylaminoethyl vinyl ether (DEAEVE), dipropylene glycol divinyl ether (DPGDVE), octadecyl vinyl ether (ODVE), a vinyl ether terminated aromatic ester monomer (i.e., hydroxybutyl vinyl ether isophthalate which can be purchased from Allied-Signal Inc., Engineered Materials Sector, P.O. Box 2332R, Morristown, N.J. 07962 under the trademark VECTOMER 4010), a vinyl ether terminated aliphatic ester monomer (i.e., cyclohexane dimethanol monovinyl ether glutarate which can be purchased from Allied-Signal Inc. under the trademark VECTOMER 4020), a vinyl ether terminated aliphatic urethane oligomer (i.e., VECTOMER 2020 which can be purposed from Allied-Signal Inc.), and a vinyl ether terminated aromatic urethane oligomer (i.e., VECTOMER 2015 and VECTOMER 2010, both of which can be purchased from Allied Signal Inc.).

The ternary photoinitiator system used in the polymerizable compositions of the present invention allows efficient cationic polymerization under conditions of room temperature and standard pressure. In addition, the initiator system can, under appropriate conditions, initiate both cationic and free-radical polymerization. This property permits its use with a variety of photopolymerizable compositions. Use of the initiator systems of the invention can provide a substantial reduction in the time required for the present compositions to cure to a tack-free gel or solid. This reduction in gel time can in some cases represent about a 30 to 70% decrease in the time required for a resin composition to harden to a tack-free gel or solid. Some systems fail to polymerize altogether in the absence of an electron donor.

The first component of the ternary photoinitiator system is an iodonium salt (PI), i.e., a diaryliodonium salt. The iodonium salt should be soluble in a monomer used to make the composition and preferably is shelf-stable, meaning it does not spontaneously promote polymerization when dissolved therein in the presence of the sensitizer and the electron donor compound, the second and third components of the photoinitiator system. Accordingly, selection of a particular iodonium salt may depend to some extent upon the particular monomer, sensitizer and donor chosen. Suitable iodonium salts are described in U.S. Pat. Nos. 3,729,313; 3,741,769; 3,808,006; 4,250,053 and 4,394,403, the iodonium salt disclosures of which are incorporated herein by reference. The iodonium salt can be a simple salt, containing an anion such as Cl—, B—, I— or $C_6H_5SO_3$—; or a metal complex salt containing an antimonate, arsenate, phosphate or borate such as $SbF_5OH$— or $AsF_6$—. Mixtures of iodonium salts can be used if desired.

Aromatic iodonium complex salts of the structure below may be used as one of the components of the ternary photoinitiator system:

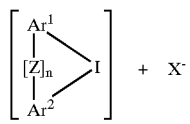

wherein
Ar$^1$ and Ar$^2$ are aromatic groups having 4 to 20 carbon atoms and are selected from the group consisting of phenyl, thienyl, furanyl and pyrazolyl groups;
Z is selected from the group consisting of oxygen; sulfur;

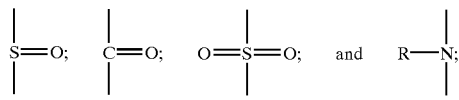

wherein R is aryl (of 6 to 20 carbons, such as phenyl) or acyl (of 2 to 20 carbons, such as acetyl, benzoyl, and the like); a carbon-to-carbon bond; or

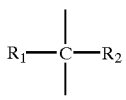

wherein $R_1$ and $R_2$ are selected from hydrogen, alkyl radicals of 1 to 4 carbons, and alkenyl radicals of 2 to 4 carbons;
n is zero or 1; and
X is a halogen-containing complex anion selected from the group consisting of tetrafluoroborate, hexafluorophosphate, hexafluoroarsenate, and hexafluoroantimonate.

The aromatic iodonium cations are stable and are well known and recognized in the art. See for example, U.S. Pat. Nos. 3,565,906; 3,712,920; 3,759,989; and 3,763,187; F. Beringer, et al., Diaryliodonium Salts IX, J. Am. Chem. Soc. 81,342–51 (1959) and F. Beringer, et al., Diaryliodonium Salts XXIII, J. Chem. Soc. 1964, 442–51; F. Beringer, et al., Iodonium Salts Containing Heterocyclic Iodine, J. Org. Chem. 30, 1141–8 (1965); J. Crivello et al., Photoinitiated Cationic Polymerization with Triarylsulfonium Salts, J. Polymer Science, 17, 977 (1979).

Representative $Ar_1$ and $Ar_2$ groups are aromatic groups having 4 to 20 carbon atoms selected from phenyl, thienyl, furanyl, and pyrazolyl groups. These aromatic groups may optionally have one or more fused benzo rings (e.g., naphthyl and the like; benzothienyl; dibenzothienyl; benzofuranyl, dibenzofuranyl; and the like). Such aromatic groups may also be substituted, if desired, by one or more of the following non-basic groups which are essentially non-reactive with epoxide and hydroxy: halogen, nitro, N-arylanilino groups, ester groups (e.g., alkoxycarbonyl such as methoxycarbonyl and ethoxycarbonyl, phenoxycarbonyl), sulfo ester groups (e.g., alkoxysulfonyl such as methoxysulfonyl and butoxysulfonyl, phenoxysulfonyl, and the like), amido groups (e.g., acetamido, butyramido, ethylsulfonamido, and the like), carbamyl groups (e.g., carbamyl, N-alkylcarbamyl, N-phenylcarbamyl, and the like), sulfamyl groups (e.g., sulfamyl, N-alkylsulfamyl, N,N-dialkylsulfamyl, N-phenylsulfamyl, and the like), alkoxy groups (e.g., methoxy, ethoxy, butoxy, and the like), aryl groups (e.g., phenyl), alkyl groups (e.g., methyl, ethyl, butyl, and the like), aryloxy groups (e.g., phenoxy)alkylsulfonyl (e.g., methylsulfonyl, ethylsulfonyl, and the like), arylsulfonyl groups (e.g., phenylsulfonyl groups), perfluoroalkyl groups (e.g., trifluoromethyl, perfluoroethyl, and the like), and perfluoroalkylsulfonyl groups (e.g., trifluoromethylsulfonyl, perfluorobutylsulfonyl, and the like).

Examples of useful aromatic iodonium complex salt photoinitiators include: diphenyliodonium tetrafluoroborate; di(4-methylphenyl)iodonium tetrafluoroborate; phenyl4-methylphenyliodonium tetrafluoroborate; di(4-heptylphenyl)iodonium tetrafluoroborate; di(3-nitrophenyl) iodonium hexafluorophosphate; di(4-chlorophenyl) iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl) iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; (4-octyloxyphenyl)phenyliodonium hexafluoroantimonate; diphenyliodonium hexafluoroantimonate; [4-(2-hydroxytetradecyloxyphenyl)]phenyliodonium hexafluoroantimonate (CD 1012); and [4-(1-methylethyl)phenyl](4-methylphenyl)iodonium tetrakis (pentafluorophenyl) borate (RHO 2074).

Of the aromatic iodonium complex salts which are suitable for use in the compositions of the invention, diaryliodonium hexafluorophosphate and diaryliodonium hexafluoroantimonate are among the preferred salts. Specific examples of such salts are (4-octyloxyphenyl) phenyliodonium hexafluoroantimonate (OPIA), [4-(2-hydroxytetradecyloxyphenyl)]phenyliodonium-hexafluoroantimonate, and [4-(1-methylethyl)phenyl](4methylphenyl)iodonium tetrakis (pentafluorophenyl) borate. These salts are preferred because, in general, they are more thermally stable, promote faster reaction, and are more soluble in inert organic solvents than are other aromatic iodonium salts of complex ions.

The aromatic iodonium complex salts may be prepared by metathesis of corresponding aromatic iodonium simple salts (such as, for example, diphenyliodonium bisulfate) in accordance with the teachings of Beringer et al., J. Am. Chem. Soc., 81,342 (1959). Thus, for example, the complex salt diphenyliodonium tetrafluoroborate is prepared by the addition at 60° C. of an aqueous solution containing 29.2 g silver fluoroborate, 2 g fluoroboric acid, and 0.5 g phosphorous acid in about 30 ml of water to a solution of 44 g (139 millimoles) of diphenyliodonium chloride. The silver halide that precipitates is filtered off and the filtrate concentrated to yield diphenyliodonium fluoroborate which may be purified by recrystallization.

The aromatic iodonium simple salts may be prepared in accordance with Beringer et al., above, by various methods including: (1) coupling of two aromatic compounds with iodyl sulfate in sulfuric acid, (2) coupling of two aromatic compounds with an iodate in acetic acid-acetic anhydride-sulfuric acid, (3) coupling of two aromatic compounds with an iodine acrylate in the presence of an acid, and (4) condensation of an iodoso compound, an iodoso diacetate, or an iodoxy compound with another aromatic compound in the presence of an acid. Diphenyliodonium bisulfate is prepared by method (3), for example, by the addition over a period of eight hours at below 5° C. of a mixture of 35 ml of conc. sulfuric acid and 50 ml of acetic anhydride to a well-stirred mixture of 55.5 ml of benzene, 50 ml of acetic anhydride, and 53.5 g of potassium iodate. The mixture is stirred for an additional four hours at 0°–5° C. and at room temperature (about 25° C.) for 48 hours and treated with 300 ml of diethyl ether. On concentration, crude diphenyliodonium bisulfate precipitates and may be purified by recrystallization if desired.

The second component in the photoinitiator system is the photosensitizer (PS). Desirably, the photoinitiator should be sensitized to the visible spectrum to allow the polymerization to be initiated at room temperature using visible light. The sensitizer should be soluble in the photopolymerizable composition, free of functionalities that would substantially interfere with the cationic curing process, and capable of light absorption within the range of wavelengths between about 300 and about 1000 nanometers.

A sensitizer is selected based in part upon shelf stability considerations. Accordingly, selection of a particular sensitizer may depend to some extent upon the particular vinyl ether, other resin components, iodonium salt, and electron donor chosen.

Suitable sensitizers include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring deep cure (e.g., cure of highly-filled composites), it is preferred to employ sensitizers having an extinction coefficient below about 1000 lmole$^{-1}$ cm$^{-1}$, more preferably about or below 100 lmole$^{-1}$ cm$^{-1}$, at the desired wavelength of irradiation for photopolymerization, or alternatively, the initiator should exhibit a decrease in absorptivity upon light exposure. Many of the alpha-diketones are an example of a class of sensitizers having this property, and are particularly preferred for dental applications.

By way of example, a preferred class of ketone sensitizers has the formula:

where X is CO or CR$^1$R$^2$ where R$^1$ and R$^2$ can be the same or different, and can be hydrogen, alkyl, alkaryl or aralkyl, b is zero or one, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable α-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzyl, 2,2'-3,3'- and 4,4'-dihydroxybenzyl, furyl, di-3,3'-indolylethanedione, 2,3-bomanedione (camphorquinone), biacetyl, 1,2-cyclohexanedione, 1,2-naphthaquinone, acenaphthaquinone, and the like.

Examples of particularly preferred visible light sensitizers include camphorquinone (CQ); 2-chlorothioxanthan-9-one; glyoxal; biacetyl; 3,3,6,6-tetramethylcyclohexanedione; 3,3,7,7-tetramethyl-1,2-cycloheptanedione; 3,3,8,8-tetramethyl-1,2-cyclooctanedione; 3,3,18,18-tetramethyl-1,2-cyclooctadecanedione; dipivaloyl; benzyl; furyl; hydroxybenzyl; 2,3-butanedione; 2,3-pentanedione; 2,3-hexanedione; 3,4-hexanedione; 2,3-heptanedione; 3,4-heptanedione; 2,3-octanedione; 4,5-octanedione; and 1,2- cyclohexanedione. Most preferably, the photosensitizer is (+/−) camphorquinone.

The third component of the initiator system is one or more electron donor compounds (ED). The electron donor compound(s) should meet the requirements set forth below and be soluble in the polymerizable composition. The donor can also be selected in consideration of other factors, such as shelf stability and the nature of the polymerizable materials, iodonium salt and sensitizer chosen. A class of donor compounds that may be useful in the inventive systems may be selected from some of the donors described in Palazzotto et al., U.S. Pat. No. 5,545,676. Possible donor compounds that meet the criteria set forth by Palazzotto et al. must then be tested using one or both of the methods set forth below to determine if they will be useful donors for the photopolymerizable compositions of the invention.

The donor is typically an alkyl aromatic polyether or an alkyl, aryl amino compound wherein the aryl group is optionally substituted by one or more electron withdrawing groups. Examples of suitable electron withdrawing groups include carboxylic acid, carboxylic acid ester, ketone, aldehyde, sulfonic acid, sulfonate and nitrile groups.

The suitability of a compound for use as an electron donor in the compositions of the invention may be determined by measuring the photoinduced potential of a sample photoinitiator system that includes the compound. The photoinduced potential can be evaluated in the following manner. A standard solution is prepared that contains $2.9 \times 10^{-5}$ moles/g of diphenyl iodonium hexafluoroantimonate and $1.5 \times 10^{-5}$ moles/g of camphorquinone (CQ) in 2-butanone. A pH electrode is then immersed in the solution and a pH meter is calibrated to zero mV. A test solution of the standard solution and the compound is prepared next using the compound at a concentration of $2.9 \times 10^{-5}$ moles/g. This test solution is irradiated using blue light having a wavelength of about 400 to 500 nm having an intensity of about 200 to 400 mW/cm$^2$ for about 5 to 10 seconds at a distance of about 1 mm. Millivolts relative to the standard solution are then determined by immersing the pH electrode in the test solution and obtaining a mV reading on the pH meter. Useful donors are those compounds that provide a reading of at least 50 mV relative to the standard solution, and preferably provide a gel time for the compositions that is at least about 30 to 40 percent shorter than for compositions that do not contain the donor. Higher mV readings are generally indicative of greater activity.

In some instances there may be some uncertainty regarding the outcome of the above procedure. This may be due to questions or uncertainty arising from the instrumentation employed, from the way the procedure was carried out, or other factors, or one may wish to verify the suitability of a particular compound. A second test may be performed to verify the result obtained by following the above procedure and resolve any such uncertainty.

The second method involves the evaluation of the photoinduced potential of an initiator system that includes the compound compared to a system that includes N,N-dimethylaniline. For this method, a standard solution of $2.9 \times 10^{-5}$ moles/g diphenyl iodonium hexafluoroantimonate, $1.5 \times 10^{-5}$ moles/g camphorquinone (CQ) and $2.9 \times 10^{-5}$ moles/g of N,N-dimethylaniline in 2-butanone is prepared. A pH electrode is then immersed in the solution and a pH meter is calibrated to zero mV. The standard solution is irradiated with blue light having a wavelength of between about 400–500 nm and an intensity of about 200 to 400 mW/cm$^2$ for about 5 to 10 seconds using a focused light source such as a dental curing light at a distance of about 1 mm. After light exposure, the potential of the solution is measured by immersing a pH electrode in the irradiated standard solution and reading the potential in mV using a pH meter. A test solution is then prepared using $2.9 \times 10^{-5}$ moles/g of diphenyl iodonium hexafluoroantimonate, $1.5 \times 10^{-5}$ moles/g of camphorquinone and $2.9 \times 10^{-5}$ moles/g of the compound in 2-butanone. The test solution is irradiated and the photoinduced potential measured using the same technique as described for the standard solution. If the test solution has a photoinduced potential that is the same as or greater than that of the N,N-dimethylaniline containing standard solution, then the compound is a useful donor.

A preferred group of alkyl, aryl amine donor compounds is described by the following structural formula:

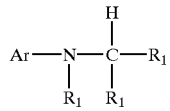

wherein
each $R_1$ is independently H; $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, COOH, COOC$_{1-18}$ alkyl, (C$_{1-18}$ alkyl)$_{0-1}$—CO—C$_{1-18}$ alkyl, SO$_3$R$^2$; aryl that is optionally substituted by one or more electron withdrawing groups; or the R$^1$ groups together may form a ring, where $R^2$ is H; $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, COOH, COOC$_{1-18}$ alkyl, (C$_{1-18}$ alkyl)$_{0-1}$—CO—C$_{1-18}$ alkyl, or SO$_3$H; and Ar is aryl that is optionally substituted by one or more electron withdrawing groups. Suitable electron withdrawing groups include —COOH, —COOR$^2$, —SO$_3$R$^2$, —CN, —CO—C$_{1-18}$alkyl, and C(O)H groups.

A preferred group of aryl alkyl polyethers has the following structural formula:

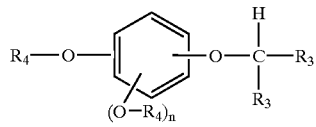

wherein n=1–3, each $R_3$ is independently H or $C_{1-18}$ alkyl that is optionally substituted by one or more halogen, —CN, —OH, —SH, $C_{1-18}$ alkoxy, $C_{1-18}$ alkylthio, $C_{1-18}$ cycloalkyl, aryl, substituted aryl, —COOH, —COOC$_{1-18}$ alkyl, —(C$_{1-18}$ alkyl)$_{0-1}$—COH, —(C$_{1-18}$ alkyl)$_{0-1}$—CO—C$_{1-18}$ alkyl, —CO—C$_{1-18}$ alkyl, —C(O)H or —C$_{2-18}$ alkenyl groups and each $R_4$ can be $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, substituted aryl, —COOH, —COOC$_{1-18}$ alkyl, —(C$_{1-18}$ alkyl)$_{0-1}$—COH, —(C$_{1-18}$ alkyl)$_{0-1}$—CO—C$_{1-18}$ alkyl, —CO—C$_{1-18}$ alkyl, —C(O)H or —C$_{2-18}$ alkenyl groups.

In each of the above formulas, the alkyl groups can be straight-chain or branched, and the cycloalkyl group preferably has 3 to 6 ring carbon atoms but may have additional alkyl substitutions up to the specified number of carbon atoms. The aryl groups may be carbocyclic or heterocyclic aryl, but are preferably carbocyclic, and more preferably are phenyl rings.

Preferred donor compounds include, but are not limited to, 4,4'-bis(diethylamino) benzophenone, 4-dimethylaminobenzoic acid (4-DMABA), ethyl 4-dimethylaminobenzoate (EDMAB), 3-dimethylamino benzoic acid (3-DMABA), 4-dimethylaminobenzoin (DMAB), 4-dimethylaminobenzaldehyde (DMABAL), 1,2, 4-trimethoxybenzene (TMB), and N-phenylglycine (NPG).

The photoinitiator compounds are provided in an amount effective to initiate or enhance the rate of cure of the resin system. It has been found that the amount of donor that is used can be critical, particularly when the donor is an amine. Too much donor can be deleterious to cure properties. Preferably, the sensitizer is present in about 0.05–5 weight percent based on resin compounds of the overall composition. More preferably, the sensitizer is present at 0.10–1.0 weight percent. Similarly, the iodonium initiator is preferably present at 0.05–10.0 weight percent, more preferably at 0.10–5.0 weight percent, and most preferably 0.50–3.0 weight percent. Likewise, the donor is preferably present at 0.01–5.0 weight percent, more preferably 0.0514 1.0 weight percent, and most preferably 0.05–0.50 weight percent.

The cationically polymerizable epoxide useful in the compositions of the invention are organic compounds having an oxirane ring, i.e., a group of the formula:

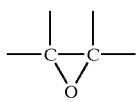

which is polymerizable by ring opening. Such materials, broadly called epoxides, include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. For example, the backbone may be of any type, and substituent groups thereon can be any group that does not substantially interfere with cationic cure at room temperature (RT). Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexene oxide groups, such as epoxycyclohexanecarboxylates, typified by 3',4'-epoxycyclohexylmethyl-3,4-epoxycyclohexane carboxylate (UVR 6105 or 6105), 3,4-epoxy-2-methylcyclohexylmethyl-3,4-epoxy-2-methylcyclohexane carboxylate, diglycidyl ether of bisphenol A, vinyl cyclohexene dioxide (ERL 4206 or 4206), butanediol diglycidyl ether (RD 2), and bis(3,4-epoxy-6-methylcyclohexylmethyl)adipate. For a more detailed list of useful epoxides of this nature, reference is made to the U.S. Pat. No. 3,117,099, which is incorporated herein by reference.

Further epoxy-containing materials which are useful in the compositions of this invention include glycidyl ether monomers of the formula:

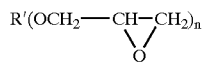

where R' is alkyl or aryl and n is an integer of 1 to 6. Examples of these materials are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type are described in U.S. Pat. No. 3,018,262, which is incorporated herein by reference, and in "Handbook of Epoxy Resins" by Lee and Neville, McGraw-Hill Book Co., New York (1967).

There are a host of commercially available epoxy resins which can be used in this invention. In particular, epoxides which are readily available include octadecylene oxide, epichlorohydrin, styrene oxide, vinyl cyclohexene oxide, glycidol, glycidylmethacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "CYRACURE UVR 6110" or UVR 6105" from Union Carbide Corp.), 3,4-epoxy-6-methylcyclohexylmethyl-3,4epoxy-6-methyl-cyclohexene carboxylate (e.g., "ERL-4201" from Union Carbide Corp.), bis(3,4-epoxy-6-methylcyclohexylmethyl)adipate (e.g., "ERL-4289" from Union Carbide Corp.), bis(2,3-epoxycyclopentyl)ether (e.g., "ERL-0400" from Union Carbide Corp.), aliphatic epoxy modified from polypropylene glycol (e.g., "ERL4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, halogenated epoxy resins (e.g., "DER-580", a brominated bisphenol type epoxy resin available from Dow Chemical Co., which is flame retardant), 1,4-butanediol diglycidyl ether of phenolformaldehyde novolak (e.g., "DEN-431" and "DENA438" from Dow Chemical Co.), and resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5, 5-spiro-3,4-epoxy)cyclohexane-meta-dioxane (e.g., "ERL-4234" from Union Carbide Corp.), vinylcyclohexene monoxide 1,2-epoxyhexadecane (e.g., "VR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-ter butylphenyl glycidyl ether (e.g., "HELOXY Modifier 65" from Shell Chemical Co.), polyfunctional glycidyl ethers such as diglycidyl ether of 1,4- butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis[4-(2,3-epoxypropoxy)-phenyl] fluorenone (e.g., "Epon 1079" from Shell Chemical Co.).

Other useful epoxy resins are well known and contain such epoxides as epichlorohydrins, alkylene oxides, e.g., propylene oxide, styrene oxide; alkenyl oxides, e.g., butadiene oxide; glycidyl esters, e.g., ethyl glycidate. The polymers of the epoxy resin can optionally contain other functionalities that do not substantially interfere with cationic cure at room temperature.

Blends of various epoxy-containing materials are also contemplated in this invention. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar. Other cationically polymerizable polymers can additionally be incorporated, if desired.

The terms "polyol" and "hydroxyl-containing material" are used herein interchangeably. The hydroxyl-containing material which is used in the present invention can be any organic material having hydroxyl functionality of at least 1, and preferably at least 2.

Preferably, the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e. from about 32 to 200, intermediate molecular weight, i.e. from about 200 to 10,000, or high molecular weight, i.e. above about 10,000. As used herein, all molecular weights are weight average molecular weights.

The hydroxyl-containing material can optionally contain other functionalities that do not substantially interfere with cationic cure at room temperature. Thus, the hydroxyl-containing materials can be nonaromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic cure at room temperature. The hydroxyl-containing material can, for example, be selected from naturally occurring or synthetically prepared cellulosic materials. Of course, the hydroxyl-containing material is also substantially free of functionality which may be thermally or photolytically unstable or which may interfere with cationic cure; that is, the material will not decompose or liberate volatile components at temperatures below about 100° C. or in the presence of actinic light which may be encountered during the desired curing conditions for the photocopolymerizable composition.

Representative examples of suitable hydroxyl-containing materials having a hydroxyl functionality of 1 include alkanols, monoalkyl ethers of polyoxyalkyleneglycols, monoalkyl ethers of alkylene-glycols, and others known in the art.

Representative examples of useful monomeric polyhydroxy organic materials include alkylene glycols (e.g., 1,2-ethanediol; 1,3-propanediol; 1,4-butanediol; 1,6-hexanediol; 1,8-octanediol; 2-ethyl-1,6-hexanediol; bis(hydroxymethyl)cyclohexane; 1,18-dihydroxyoctadecane; 3-chloro-1,2-propanediol); polyhydroxyalkanes (e.g., glycerine, tri-methylolethane, pentaerythritol, sorbitol) and other polyhydroxy compounds such as N,N-bis(hydroxyethyl)benzamide; 2-butyne-1,4-diol; 4,4-bis(hydroxymethyl)diphenylsulfone; castor oil; and the like.

Representative examples of useful polymerizable hydroxyl-containing materials include polyoxyethylene and polyoxypropylene glycols, and particularly the polyoxyethylene and polyoxypropylene glycol diols and triols having molecular weights from about 200 to about 10,000 corresponding to a hydroxy equivalent weight of 100 to 5000 for the diols or 70 to 3300 for triols; polytetramethylene ether glycols such as polytetrahydroftiran or "poly THF" (pTHF) of varying molecular weight; copolymers of hydroxypropyl and hydroxyethyl acrylates and methacrylates with other free radical-polymerizable monomers such as acrylate esters, vinyl halides, or styrene; copolymers containing pendent hydroxy groups formed by hydrolysis or partial hydrolysis of vinyl acetate copolymers, polyvinylacetal resins containing pendent hydroxyl groups; modified cellulose polymers such as hydroxyethylated and hydroxypropylated cellulose; hydroxy-terminated polyesters; hydroxy-terminated polylactones, and particularly the polycaprolactones; fluorinated polyoxyethylene or polyoxypropylene glycols; hydroxy-terminated polyalkadienes; and 2-oxepanone polymer with 2-ethyl-2-(hydroxymethyl)-1,3-propane diol.

Useful commercially available hydroxyl-containing materials include the "TERATHANE" series of polytetramethylene ether glycols such as "TERATHANE" 650, 1000, 2000 and 2900 (available from du Pont de Nemours, Wilmington, Del.) the "PEP" series of polyoxyalkylene tetrols having secondary hydroxyl groups such as "PEP" 450, 550 and 650; "BUTVAR" series of polyvinylacetal resins such as "BUTVAR" B-72A, B-73, B-76, B-90 and B-98 (available from Monsanto Chemical Company, St. Louis, Mo.); and the "FORMVAR" series of resins such as 7/70, 12/85, 7/95S, 7/95E, 15/95S and 15/95E (available from Monsanto Chemical Company); the "TONE" series of polycaprolactone polyols such as "TONE" 0200, 0210, 0230, 0240, 0300 and 0301 (available from Union Carbide); "PARAPLEX U-148" aliphatic polyester diol (available from Rohm and Haas, Philadelphia, Pa.), the "MULTRON" R series of saturated polyester polyols such as "MULTRON" R-2, R-12A, R-16, R-18, R-38, R-68 and R-74 (available from Mobay Chemical Co.); "KLUCEL E" hydroxypropylated cellulose having an equivalent weight of approximately 100 (available from Hercules Inc.); "Alcohol Soluble Butyrate" cellulose acetate butyrate ester having a hydroxyl equivalent weight of approximately 400 (available from Eastman Kodak Co., Rochester, N.Y.); polyether polyols such as polypropylene glycol diol (e.g., "ARCOL PPG-425", "Arcol PPG-725", "ARCOL PPG-1025", "ARCOL PPG-2025", "ARCOL PPG-3025", "ARCOL PPG-4025"

from ARCO Chemical Co.); polypropylene glycol triol (e.g., "ARCOL LT-28", "ARCOL LHT42", "ARCOL LHT 112", "ARCOL LHT 240", "ARCOL LG-56", "ARCOL LG-168", "ARCOL LG-650" from ARCO Chemical Co.); ethylene oxide capped polyoxypropylene triol or diol (e.g., "ARCOL 11-27", "ARCOL 11-34", "ARCOL E-351", "ARCOL E452", "ARCOL E-785", "ARCOL E-786" from ARCO Chemical Co.); ethoxylated bis-phenol A; propylene oxide or ethylene oxide—based polyols (e.g., "VORANOL" polyether polyols from the Dow Chemical Co.).

The amount of hydroxyl-containing organic material used in the compositions of the invention may vary over broad ranges, depending upon factors such as the compatibility of the hydroxyl-containing material with the epoxide, the equivalent weight and functionality of the hydroxyl-containing material, the physical properties desired in the final cured composition, the desired speed of photocure, and the like.

Blends of various hydroxyl-containing materials are particularly contemplated in this invention. Examples of such blends include two or more molecular weight distributions of hydroxyl-containing compounds, such as low molecular weight (below 200), intermediate molecular weight (about 200 to 10,000) and higher molecular weight (above about 10,000). Alternatively or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

The spiroorthocarbonate compounds (SOCs) used in making the polymerizable compositions of the present invention are comprised of one or more compounds of the formula:

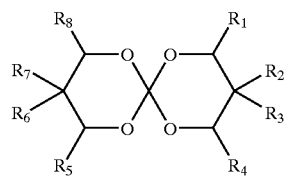

(I)

wherein $R_1$–$R_8$ are independently selected from the group consisting of hydrogen; alkyl; aryl; substituted alkyl; substituted aryl; 6-oxabicyclo[3.1.0]hex-2-yl; 6-oxabicyclo[3.1.0]hex-3-yl; (6-oxabicyclo[3.1.0]hex-2-yl)methyl; (6-oxabicyclo[3.1.0]hex-3-yl)methyl; (6-oxabicyclo[3.1.0]hex-2-yl)methoxy; (6-oxabicyclo[3.1.0]hex-3-yl)methoxy; 7-oxabicyclo[4.1.0]hept-2-yl; 7-oxabicyclo[4.1.0]hept-3-yl; (7-oxabicyclo[4.1.0]hept-2-yl)methyl; (7-oxabicyclo[4.1.0]hept-3-yl)methyl; (7-oxabicyclo[4.1.0]hept-2-yl)methoxy; (7-oxabicyclo[4.1.0]hept-3-yl)methoxy; and —$(CH_2)_n$—O—(O=C)—$R_9$, where n=1 through 9 and $R_9$=H, alkyl, aryl, substituted alkyl or substituted aryl, or $R_1 \cdot R_2$, $R_2 \cdot R_3$, $R_5 \cdot R_6$, and $R_6 \cdot R_7$ are independently selected from the group consisting of —$CH_2(CH_2)_nCH_2$— where n=3, 4, 5, and 6; —$CH_2$-epoxy-$(CH_2)_n$—$CH_2$— where n=0, 1, and 2; and —O— so as to form an alicyclic ring or an oxirane ring between $R_1$ and $R_2$, $R_2$ and $R_3$, $R_5$ and $R_6$, and $R_6$ and $R_7$, provided that $R_3$, $R_4$, $R_7$, and $R_8$ are hydrogen when $R_1 \cdot R_2$ and $R_5 \cdot R_6$ are independently selected from the group consisting of —$CH_2(CH_2)_nCH_2$— where n=3, 4, 5 and 6 so as to form an alicyclic ring between $R_1$ and $R_2$ and between $R_5$ and $R_6$;

$R_2$, $R_3$, $R_4$, $R_6$, $R_7$, and $R_8$ are hydrogen when $R_1$ and $R_5$ are independently selected from the group consisting of alkyl, aryl, substituted alkyl, and substituted aryl;

$R_1$, $R_4$, $R_5$, and $R_8$ are hydrogen when $R_2$ and $R_6$ are independently selected from the group consisting of alkyl, aryl, substituted alkyl, and substituted aryl and $R_3$ and $R_7$ are independently selected from the group consisting of —$(CH_2)_n$—O—(O=C)—$R_9$ where n=1 and 2 and $R_9$=H, alkyl, aryl, substituted alkyl or substituted aryl;

$R_1$, $R_4$, $R_5$, and $R_8$ are hydrogen when $R_2$ and $R_3$ are independently selected from the group consisting of H, alkyl, aryl, substituted alkyl, and substituted aryl and $R_6 \cdot R_7$=—$CH_2$-epoxy-$(CH_2)_n$—$CH_2$— where n 0, 1, and 2 so as to form an alicyclic ring between $R_6$ and $R_7$;

$R_1$, $R_4$, $R_5$, and $R_8$ are hydrogen when $R_2 \cdot R_3$ and $R_6 \cdot R_7$ are independently selected from the group consisting of —$CH_2$-epoxy-$(CH_2)_n$—$CH_2$— where n=0, 1, and 2 so as to form an alicyclic ring between $R_2$ and $R_3$ and between $R_6$ and $R_7$;

$R_1$, $R_4$, $R_5$, and $R_8$ are hydrogen when $R_2$ is independently selected from the group consisting of 6-oxabicyclo[3.1.0]hex-2-yl, 6-oxabicyclo[3.1.0]hex-3-yl, (6-oxabicyclo[3.1.0]hex-2-yl)methyl, (6-oxabicyclo[3.1.0]hex-3-yl)methyl, (6-oxabicyclo[3.1.0]hex-2-yl)methoxy, (6-oxabicyclo[3.1.0]hex-3-yl)methoxy, 7-oxabicyclo[4.1.0]hept-2-yl, 7-oxabicyclo[4.1.0]hept-3-yl, (7-oxabicyclo[4.1.0]hept-2-yl)methyl, (7-oxabicyclo[4.1.0]hept-3-yl)methyl, (7-oxabicyclo[4.1.0]hept-2-yl)methoxy, and (7-oxabicyclo[4.1.0]hept-3-yl)methoxy, and $R_3$, $R_6$, and $R_7$ are independently selected from the group consisting of hydrogen, alkyl, aryl, substituted alkyl, and substituted aryl;

$R_3$, $R_4$, $R_5$, $R_6$, $R_7$, and $R_8$ are independently selected from the group consisting of the group consisting of hydrogen, alkyl, aryl, substituted alkyl, and substituted aryl, when $R_1 \cdot R_2$=—O— so as to form an oxirane ring between $R_1$ and $R_2$; and $R_3$, $R_4$, $R_7$, and $R_8$ are independently selected from the group consisting of the group consisting of hydrogen, alkyl, aryl, substituted alkyl, and substituted aryl, when $R_1 \cdot R_2$ and $R_5 \cdot R_6$=—O— so as to form an oxirane ring between $R_1$ and $R_2$ and between $R_5$ and $R_6$.

Certain spiroorthocarbonates represented by formula (I) above are novel compounds. These compounds are compounds of formula (I)

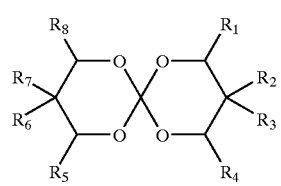

(I)

wherein $R_1$–$R_8$ are independently selected from the group consisting of hydrogen; alkyl; aryl; substituted alkyl; substituted aryl; 6-oxabicyclo[3.1.0]hex-2-yl; 6-oxabicyclo[3.1.0]hex-3-yl; (6-oxabicyclo[3.1.0]hex- 2-yl)methyl; (6-oxabicyclo[3.1.0]hex-3-yl)methyl; (6-oxabicyclo[3.1.0]hex-2-yl)methoxy; (6-oxabicyclo[3.1.0]hex-3-yl)methoxy; 7-oxabicyclo[4.1.0]hept-2-yl; 7-oxabicyclo[4.1.0]hept-3-yl; (7-oxabicyclo[4.1.0]hept-2-yl)methyl; (7-oxabicyclo[4.1.0]hept-3-yl)methyl; (7-oxabicyclo[4.1.0]hept-2-yl)methoxy; (7-oxabicyclo[4.1.0]hept-3-yl)methoxy; and —(CH$_2$)$_n$—O—(O=C)—R$_9$, where n=1 through 9 and R$_9$=H, alkyl, aryl, substituted alkyl and substituted aryl, or R$_1$•R$_2$, R$_2$•R$_3$, R$_5$•R$_6$, and R$_6$•R$_7$ are independently selected from the group consisting of —CH$_2$(CH$_2$)$_n$CH$_2$— where n=3, 4, 5, and 6 and —CH$_2$-epoxy-(CH$_2$)$_n$—CH$_2$— where n=0, 1, and 2, and —O— so as to form an alicyclic ring or an oxirane ring between R$_1$ and R$_2$, R$_2$ and R$_3$, R$_5$ and R$_6$, or R$_6$ and R$_7$;

provided that

R$_1$, R$_4$, R$_5$, and R$_8$ are hydrogen when R$_2$ is independently selected from the group consisting of 6-oxabicyclo[3.1.0]hex-2-yl, 6-oxabicyclo[3.1.0]hex-3-yl, (6-oxabicyclo[3.1.0]hex-2-yl)methyl, (6-oxabicyclo[3.1.0]hex-3-yl)methyl, (6-oxabicyclo[3.1.0]hex-2-yl)methoxy, (6-oxabicyclo[3.1.0]hex-3-yl)methoxy, 7-oxabicyclo[4.1.0]hept-2-yl, 7-oxabicyclo[4.1.0]hept-3-yl, (7-oxabicyclo[4.1.0]hept-2-yl)methyl, (7-oxabicyclo[4.1.0]hept-3-yl)methyl, (7-oxabicyclo[4.1.0]hept-2-yl)methoxy, (7-oxabicyclo[4.1.0]hept-3-yl)methoxy, and R$_3$, R$_6$ and R$_7$ are independently selected from the group consisting of hydrogen, alkyl, aryl, substituted alkyl, and substituted aryl;

R$_1$, R$_4$, R$_5$, and R$_8$ are hydrogen when R$_2$ and R$_3$ are independently selected from the group consisting of 6-oxabicyclo[3.1.0]hex-2-yl, 6-oxabicyclo[3.1.0]hex-3-yl, (6-oxabicyclo[3.1.0]hex-2-yl)methyl, (6-oxabicyclo[3.1.0]hex-3-yl)methyl, (6-oxabicyclo[3.1.0]hex-2-yl)methoxy, (6-oxabicyclo[3.1.0]hex-3-yl)methoxy, 7-oxabicyclo[4.1.0]hept-2-yl, 7-oxabicyclo[4.1.0]hept-3-yl, (7-oxabicyclo[4.1.0]hept-2-yl)methyl, (7-oxabicyclo[4.1.0]hept-3-yl)methyl, (7-oxabicyclo[4.1.0]hept-2-yl)methoxy, (7-oxabicyclo[4.1.0]hept-3-yl)methoxy, and R$_3$ and R$_7$ are independently selected from the group consisting of hydrogen, alkyl, aryl, substituted alkyl, and substituted aryl;

R$_3$, R$_4$, R$_5$, R$_6$, R$_7$, and R$_8$ are independently selected from the group consisting of the group consisting of hydrogen, alkyl, aryl, substituted alkyl, and substituted aryl, when R$_1$•R$_2$=—O— so as to form an oxirane ring between R$_1$ and R$_2$;

R$_3$, R$_4$, R$_7$, and R$_8$ are independently selected from the group consisting of the group consisting of hydrogen, alkyl, aryl, substituted alkyl, and substituted aryl, when R$_1$•R$_2$ and R$_5$•R$_6$=—O— so as to form an oxirane ring between R$_1$ and R$_2$ and between R$_5$ and R$_6$;

R$_1$, R$_4$, R$_5$, and R$_8$ are hydrogen when R$_2$ and R$_3$ are ethyl and R$_6$•R$_7$ are —CH$_2$— epoxy-(CH$_2$)$_n$-CH$_2$— where n=1 and 2 so as to form an alicyclic ring between R$_6$ and R$_7$; and R$_1$, R$_4$, R$_5$, and R$_8$ are hydrogen when R$_2$•R$_3$ and R$_6$•R$_7$ are —CH2-epoxy-(CH$_2$)$_n$—CH$_2$— where n=1 and 2 so as to form an alicyclic ring between R$_2$ and R$_3$ and R$_6$ and R$_7$.

These novel compounds include, but are not limited to, 5,5-diethyl-19-oxadispiro[1,3-dioxane-2,2'-1,3-dioxane-5'4"-bicyclo[4.1.0]heptane], 7,26-dioxatrispiro[bicyclo[4.1.0]heptane-4,5'-1,3-dioxane-2'2"-1,3-dioxane-5"',4"-bicyclo[4.1.0]heptane], 5-5-diethyl-18-oxadispiro[1,3-dioxane-2,2'-1,3-dioxane-5'3"-bicyclo[3.1.0]hexane], and 6,24-dioxatrispiro[bicyclo[3.1.0]hexane-3,5'-1,3-dioxane-2'2"-1,3-dioxane-5"3"'-bicyclo[3.1.0]hexane], 3,3-diethyl-1,5,7,11-tetraoxa-9-[(6-oxabicyclo[3.1.0]hex-3-yl)methoxy] spiro[5.5]undecane, 3,9-bis[(6-oxabicyclo[3.1.0]hex-3-yl)methoxy]-3-ethyl-1,5,7,11-tetraoxaspiro[5.5]undecane,3,3-diethyl-1,5,7,11-tetraoxa-9-[(6-oxabicyclo[3.1.0]hex-2-yl)methoxy]spiro[5.5]undecane, 3,9-bis[(6-oxabicyclo[3.1.0]hex-2-yl)methoxy]-3-ethyl-1,5,7,11-tetraoxaspiro[5.5]undecane, 3,3-diethyl-1,5,7,11-tetraoxa-9-[(6-oxabicyclo[3.1.0]hex-3-yl)methyl]spiro[5.5]undecane, 3,9-[bis(6-oxabicyclo[3.1.0]hex-2-yl)methyl]-3-ethyl-1,5,7,11-tetraoxaspiro[5.5]undecane, 3,3-diethyl-1,5,7,11-tetraoxa-9-[(6-oxabicyclo[3.1.0]hex-2-yl)methyl]spiro[5.5]undecane, 3,9-bis[(6-oxabicyclo[3.1.0]hex-2-yl)methyl]-3-ethyl-1,5,7,11-tetraoxaspiro[5.5]undecane, 3,3-diethyl-1,5,7,11-tetraoxa-9-(7-oxabicyclo[4.1.0]hept-3-yl)methyl]spiro[5.5]undecane, 3,9-bis(p7-oxabicyclo[4.1.0]hept-3-yl)methyl]-3-ethyl-1,5,7,11-tetraoxaspiro [5.5]undecane, 3,3-diethyl-1,5,7,11-tetraoxa-9-(7-oxabicyclo[4.1.0]hept-2-yl)methyl]spiro[5.5]undecane, 3,9-bis(7-oxabicyclo[4.1.0]hept-2-yl)methyl]-3-ethyl-1,5,7,11-tetraoxaspiro[5.5]undecane, 3,3-diethyl-1,5,7,11-tetraoxa-9-(6-oxabicyclo[3.1.0]hex-3-yl)spiro[5.5]undecane, 3,9-bis(6-oxabicyclo[3.1.0]hex-3-yl)-3-ethyl-1,5,7,11-tetraoxaspiro[5.5]undecane, 3,3-diethyl-1,5,7,11-tetraoxa-9-(6-oxabicyclo[3.1.0]hex-2-yl)spiro[5.5]undecane, 3,9-bis(6-oxabicyclo[3.1.0]hex-2-yl)-3-ethyl-1,5,7,11-tetraoxaspiro[5.5]undecane, 3,9-bis(7-oxabicyclo[3.1.0]hex-3-yl)-3-ethyl-1,5,7,11-tetraoxaspiro[5.5]undecane, 3,3-diethyl-1,5,7,11-tetraoxa-9-(7-oxabicyclo[3.1.0hex-3-yl)spiro[5.5]undecane, 3,9-bis(7-oxabicyclo[3.1.0]hex-2-yl)-3-ethyl-1,5,7,11-tetraoxaspiro[5.5]undecane, 3,3-diethyl-1,5,7,11-tetraoxa-9-(7-oxabicyclo[3.1.0]hex-2-yl)spiro[5.5]undecane, 2,4,7,9,11,14-hexaoxaspiro[bicyclo[4.1.0]heptane-3,3'bicyclo[4.1.0]heptane], 8,10,13-trioxaspiro[1,3-dioxane-2,3'-bicyclo[4.1.0]heptane], 5,12-dimethyl-2,4,7,9.11,14-hexaoxaspiro[bicyclo[4.1.0]heptane-3,3'bicyclo[4.1.0]heptane], 4,5,5,11-tetramethyl-8,10-13-trioxaspiro[1,3-dioxane-2,3'-bicyclo[4.1.0]heptane], and 5,5-dimethyl-8,10-13-trioxaspiro[1,3-dioxane-2,3'-bicyclo[4.1.0]heptane]. Each of these novel spiroorthocarbonates has at least one epoxy functional group.

The chemical structures of the above-listed novel compounds are as follows:

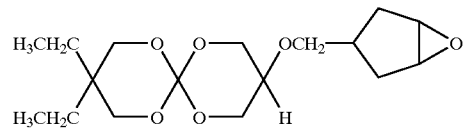

3,3-diethyl-1,5,7,11-tetraoxa-9-[(6-oxabicyclo[3.1.0]hex-3-yl)methoxy]spiro[5.5]undecane

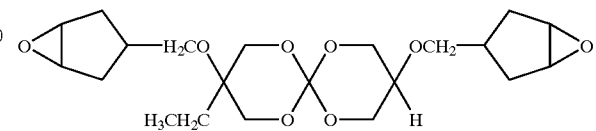

3,9-bis[(6-oxabicyclo[3.1.0]hex-3-yl)methoxy]3-ethyl-1,5,7,11-tetraoxaspiro[5.5]undecane

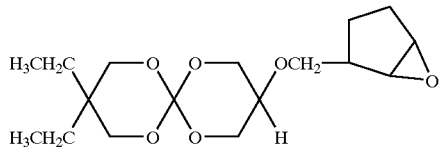

3,3-diethyl-1,5,7,11-tetraoxa-9-[(6-oxabicyclo[3.1.0]hex-2-yl)methoxy]spiro[5.5]undecane

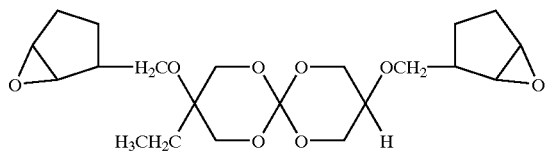

3,9-bis[(6-oxabicyclo[3.1.0]hex-2-yl)methoxy]3-ethyl-1,5,7,11-tetraoxaspiro[5.5]undecane

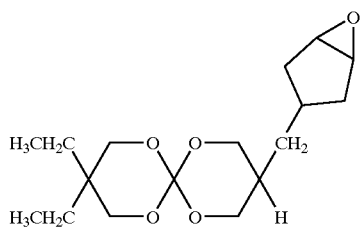

3,3-diethyl-1,5,7,11-tetraoxa-9-[(6-oxabicyclo[3.1.0]hex-3-yl)methyl]spiro[5.5]undecane

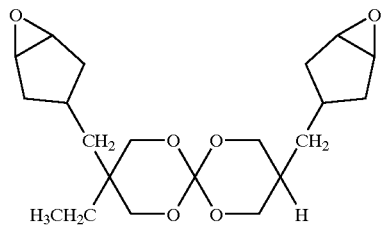

3,9-bis[(6-oxabicyclo[3.1.0]hex-3-yl)methyl]3-ethyl-1,5,7,11-tetraoxaspiro[5.5]undecane

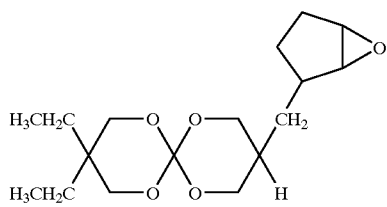

3,3-diethyl-1,5,7,11-tetraoxa-9-[(6-oxabicyclo[3.1.0]hex-2-yl)methyl]spiro[5.5]undecane

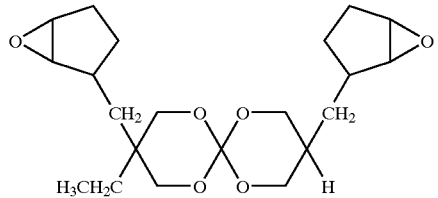

3,9-bis[(6-oxabicyclo[3.1.0]hex-2-yl)methyl]3-ethyl-1,5,7,11-tetraoxaspiro[5.5]undecane

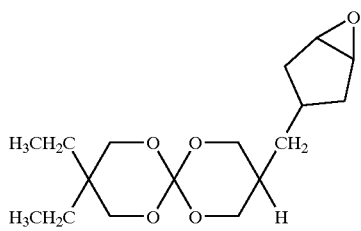

3,3-diethyl-1,5,7,11-tetraoxa-9-[(7-oxabicyclo[4.1.0]hept-3-yl)methyl]spiro[5.5]undecane

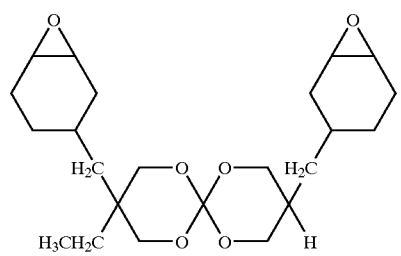

3,9-bis[(7-oxabicyclo[4.1.0]hept-3-yl)methyl]-3-ethyl-1,5,7,11-tetraoxaspiro[5.5]undecane

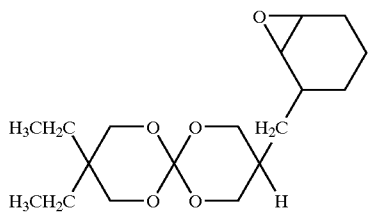

3,3-diethyl-1,5,7,11-tetraoxa-9-[(7-oxabicyclo[4.1.0]hept-2-yl)methyl]spiro[5.5]undecane

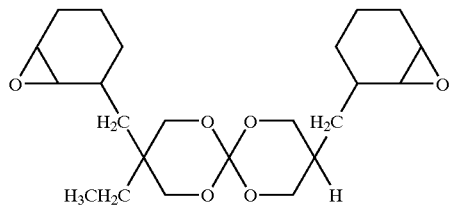

3,9-bis[(7-oxabicyclo[4.1.0]hept-2-yl)methyl]-3-ethyl-1,5,7,11-tetraoxaspiro[5.5]undecane

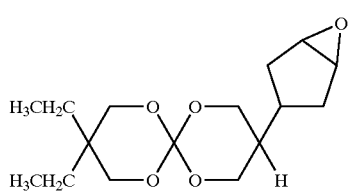

3,3-diethyl-1,5,7,11-tetraoxa-9-(6-oxabicyclo[3.1.0]hex-3-yl)spiro[5.5]undecane

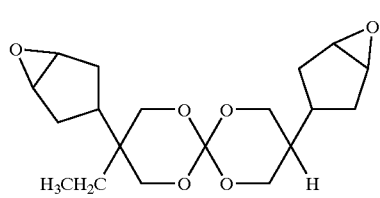

3,9-bis(6-oxabicyclo[3.1.0]hex-3-yl)-3-ethyl-1,5,7,11-tetraoxaspiro[5.5]undecane

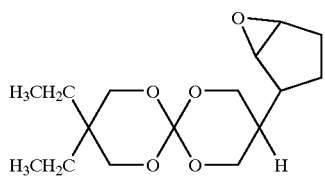

3,3-diethyl-1,5,7,11-tetraoxa-9-(6-oxabicyclo[3.1.0]hex-2-yl)spiro[5.5]undecane

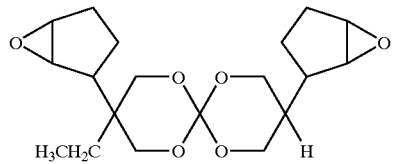

3,9-bis(6-oxabicyclo[3.1.0]hex-2-yl)-3-ethyl-1,5,7,11-tetraoxaspiro[5.5]undecane

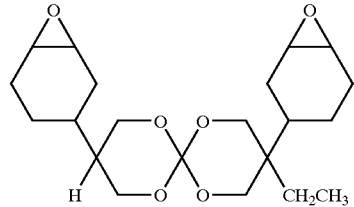

3,9-bis(7-oxabicyclo[4.1.0]hept-3-yl)-3-ethyl-1,5,7,11-tetraoxaspiro[5.5]undecane

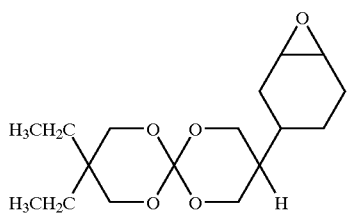

3,3-diethyl-1,5,7,11-tetraoxa-9-(7-oxabicyclo[4.1.0]hept-3-yl)spiro[5.5]undecane

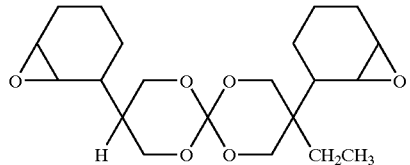

3,9-bis-(7-oxabicyclo[4.1.0]hept-2-yl)-3-ethyl-1,5,7,11-tetraoxaspiro[5.5]undecane

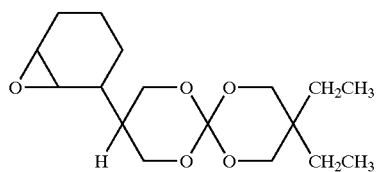

3,3-diethyl-1,5,7,11-textraoxa-9-(7-oxabicyclo[4.1.0]hept-2-yl)spiro[5.5]undecane

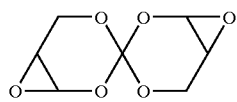

2,4,7,9,11,14-hexaoxaspiro[bicyclo [4.1.0]heptane-3,3'-bicyclo[4.1.0]heptane]

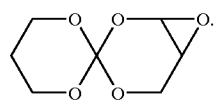

8,10,13-trioxaspiro[1,3-dioxane-2,3'-bicyclo[4.1.0]heptane]

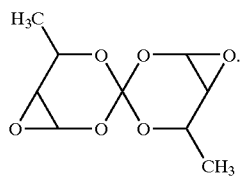

5,12-dimethyl-2,4,7,9,11,14-hexaoxaspiro[bicyclo[4.1.0]heptane-3,3'-bicyclo[4.1.0]heptane]

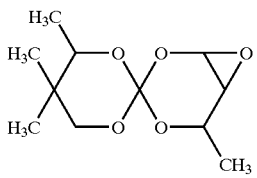

4,5,5,11-tetramethyl-8,10,13-trioxaspiro[1,3-dioxane-2,3'-bicyclo[4.1.0]heptane]

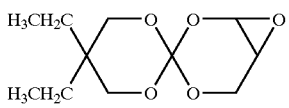

5,5-dimethyl-8,10,13-trioxaspiro[1,3-dioxane-2,3'-bicyclo[4.1.0]heptane]

The SOCs of formula I expand as they undergo ring-opening reactions and are particularly suited for use in reducing shrinkage of polymerizable compositions of the present invention. Preferably, the SOCs of formula I are tetraoxaspiroundecanes (TOSUs), which are SOCs having 2 six-membered rings that have oxygen atoms bonded to the center carbon.

The SOCs can be prepared by transesterification of tetraalkylorthocarbonates such as tetraethylorthocarbonate or tetramethylorthocarbonate and the corresponding diol using an aromatic hydrocarbon solvent such as toluene or xylene in the presence of a catalytic amount of an organic acid such as p-toluene sulfonic acid. The reaction is driven to completion by removal of the alcohol and is purified by distillation or chromatography and/or recrystallization. The spiroorthocarbonate compounds can also be prepared by other reactions involving thiophosgenation and organotin intermediates. See generally, R. K. Sadhir & R. M. Luck, *Expanding Monomers: Synthesis, Characterization and Applications*, CRC Press, Boca Raton, Fla. (1992).

The following examples, Examples 1–14, are given to illustrate methods of making various spiroorthocarbonates that may be used in making the polymerizable compositions of this invention. The examples are to be construed as illustrative and not in a limiting sense. Unless otherwise indicated, all parts and percentages are by weight, and all molecular weights are weight average molecular weight. Examples 11–14 illustrate methods of making certain novel spiroorthocarbonates of the present invention.

EXAMPLE 1 trans/trans-2,3,8,9-di(Trimethylene)-1,5,7,11-tetraoxaspiro[5.5]-undecane(DTM$_3$)

The sequence of synthetic reactions employed in the preparation of this spiroorthocarbonate is set forth in the following synthesis scheme. cis- and trans-2-Hydroxycyclopentanementhanol diacetates.

Cyclopentene was converted via a Prins reaction to an isomeric mixture (1:19) of the diacetate derivatives of the cis:trans diols. Cyclopentene (68 g, 1.0 mol), 100 mL of 37% aqueous formaldehyde (40 g, 1.3 mol), and glacial acetic acid (200 mL) were mixed and the mixture cooled to 0° C. Concentrated sulfuric acid (15 mL) was then added dropwise over a period of 1 hour and the mixture was stirred at room temperature for 18 hours. The phases were allowed to separate and the aqueous phase was discarded. The yellow-brown organic phase was washed with 50 mL of 10% aqueous sodium bicarbonate, 50 mL of 20% aqueous sodium bisulfite, 50 mL of distilled water, and 50 mL of aqueous sodium chloride. The organic phase was taken up in ether, dried over anhydrous magnesium sulfate, filtered, and the filtrate evaporated to obtain a dark liquid. The crude product was distilled at reduced pressure through a 50-cm vacuum jacketed column fitted with a spiral titanium wire to obtain 110 g (55% yield) of a 1:19 mixture of cis- and trans-2-hydroxycyclopentanementhanol diacetates (bp 91° to 93° C. at 4.8 mmHg). cis- and trans-2-Hydroxycyclopentanemethanols.

Transesterification of the diacetate mixture using sodium methoxide in methanol liberated an isomeric diol mixture. The mixture of isomeric diacetates (103 g, 0.5 mol) was dissolved in 500 mL of methanol, and the mixture was made weakly alkaline with 1 to 2 g sodium. The color turned to light yellow, and a strong smell of methyl acetate was evident. A mixture of methyl acetate and methanol was then distilled off in the range of 57° to 70° C. at atmospheric pressure using a fractionating still. The viscous residue was neutralized with a few milliliters of acetic acid. A small forerun with a strong smell of formaldehyde was first removed by distillation at waterpump pressure, and the diol mixture was finally distilled under reduced pressure to obtain (43 g, 96% yield) of product (bp 110° to 118° C. at 3.7 mmHg).

trans-2-Hydroxycyclopentanemethanol

The diol mixture was treated with anhydrous cupric sulfate and dry acetone to selectively convert the cis-isomer to an acetonide. The particulate matter was removed by filtration and the filtrate distilled, isolating the acetonide in the first fraction (26° to 28° C.; 1 mmHg), and the trans-diol 5 thereafter (96° to 99° C.); 1 mmHg, 121° to 125° C.; 6 mmHg, 137° to 140° C.; 13 mmHg). The acetonide can be converted back to the cis-diol by hydrolysis.

trans/trans-2,3,8,9-di(Trimethylene)-1,5,7,11-tetraoxaspiro[5.5]undecane trans-Diol 5 (30.6 g, 0.264 mol) and o-xylene (250 mL) were added to a flame-dried flask fitted with a Dean-Stark trap and reflux condenser. The reaction mixture was refluxed (140° C.) with azeotropic removal of water over 1.5 h. Upon cooling to room temperature, the mixture became turbid. Dried p-toluenesulfonic acid (PTSA) (0.7 g) and tetraethyl orthocarbonate 6 (26.2 g 97%, 0.132 moles) were added to the reaction mixture, which subsequently begin to clarify. The reaction was again heated, and 26.5 mL ethanol was collected within the first hour. The reaction was maintained at 108° C. overnight. An additional 1.8 mL ethanol was collected after heating for 2 h at 130° to 137° C. (Total ethanol collected and removed: 28.3 mL, 31 mL theory.) After cooling to room temperature, the PTSA was neutralized (~pH 7) with triethylamine (0.7 to 0.8 mL). o-Xylene was removed by rotary evaporation at 66° to 70° C. using a water aspirator and then at room temperature, using a mechanical pump. The residue oil (40.7 g) was stirred 700 mL hexane and warned to 60° C. to obtain a homogenous solution. After addition of magnesol 30/40 (10 g) and anhydrous MgSO$_4$ (10 g), heating was continued at 60° C. for 20 min. The mixture was filtered in vacuo two times, once hot and once at room temperature, using a small amount of methylene chloride to keep the oil in solution. Solvents were removed using a rotary evaporator at room temperature using a water aspirator and then at 60° to 70° C. using a mechanical pump.

The residual oil (29.2 of 31.1 g) was transferred to a 50-mL pear-shaped flask. The oil was distilled under vacuum using a short path distillation apparatus to yield 9.6 g of an oil solid. It was noted that the main compound (135° to 153° C.; 0.20 to 0.55 mmHg) readily crystallized at 145° to 149° C.; 0.20 to 0.35 mmHg. In order to obtain analytical sample, 3.33 g of the oil solid was recrystallized from dry acetone (3.33 g) to yield 0.21 g of 7. Crystals were filtered and dried at room temperature in vacuo. DSC 180.1° C.; $^1$H NMR (300 MHz, CDCl$_3$) δ 4.0 to 4.2 (m, 4H), 3.6 to 3.9 (m, 2H), 1.5 to 2. (m, 12H), 1.1 to 1.2 (m, 2H); $^{13}$C NMR (75 MHz, CDCl$_3$) δ 116.46, 78.56, 77.29, 68.57, 67.70, 40.94, 40.82, 27.88, 27.83, 21.85, 21.76, 19.22, 187.99; IR (photoacoustic) 2960, 2914, 2875, 1397, 1324, 1243, 1213, 1197, 1116, 1073, 1001, 951 cm$^{-1}$. Anal. calcd. for $C_{13}H_{20}O_4$; C, 64, 988; H, 8.39. Found C, 64.18; H, 8.68.

EXAMPLE 2 trans/trans-2,3,8,9-di(Tetramethylene)-1,5,7,11-tetraoxaspiro[5.5]undecane (DTM$_4$)

This spiroorthocarbonate was synthesized by the sequence of preparative reactions summarized in the appended synthetic scheme.

4,5-Tetramethylene-1,3-dioxane

This dioxane was prepared by the Prins reaction of cyclohexene and formaldehyde via a reported procedure. To a stirred solution consisting of 1200 mL aqueous formaldehyde (37%) and 80 mL conc. H$_2$SO$_4$ in a 2-L three-neck flask was added (all at once) 408 mL (4 moles) of cyclohexene. The reaction flask was fitted with a thermometer and a reflux condenser. The mixture was continuously stirred and heated to reflux (~70° C.) for 14 to 16 hr. After the mixture had cooled to room temperature, it was transferred to a large separatory funnel, and the organic and aqueous phases allowed to separate. The aqueous layer (bottom) was drained off and set aside. An equal volume of anhydrous diethyl ether was added to the organic phase. The mixture was washed successively with 200-mL aliquots of the following aqueous solutions: 10 wt % NaHCO$_3$, 20% NaHSO$_3$, deionized H$_2$O, and brine (saturated NaCl). After each wash, the aqueous phase was allowed to separate, and was drained off and combined with the original aqueous layer which had been set aside earlier. (Note: Washing procedure: shake vigorously for 3 to 5 min; vent separatory funnel frequently to prevent pressure buildup.) The washed organic layer was then dried over MgSO$_4$, filtered through fluted paper, and concentrated on a rotary evaporator to remove residual solvents. The crude dioxane was then distilled at reduced pressure (water aspirator, 15 to 35 mm) either through a Vigreux column, or a Claison head fitted with an ice-water-jacketed condenser and graduated receiver. The fraction at 89° to 104° C. (head temperature) was collected (expected yield 60% to 82%, 340 to 454 g; practical yields less than 300 g). Note: The original aqueous phase and water washings can be extracted with ether reclaim any product which may have been partitioned into the aqueous phase. The extract is then subject to the same series of washings, drying, filtering, and concentrating as the original organic layer.

3,4-Tetramethylene-2-oxa-1,5-pentanediol Diacetate

The diacetate was prepared by an established acetylation method. To 156.1 g of magnetically stirred 4,5-tetramethylene-1,3-dioxane in a 500-mL Erlenmeyer flask was added rapidly an acetylating mixture consisting of 156.1 g acetic anhydride and 1 g conc. H$_2$SO$_4$. The color went from water white to light blue, to dark blue-green, and finally to dark brown. After stirring for several hours at room temperature, the mixture was allowed to stand overnight. The reaction mixture was then neutralized with 4 g of sodium acetate (the color became straw yellow) and filtered through fluted filter paper into a 500-mL round bottom still pot. The excess acetic anhydride was distilled off using a water aspirator vacuum (head temp. 60° to 76° C., pot temp. 740 to 131° C., 40 mm). Distillation was continued using a mechanical pump vacuum through a Claison head or 6-in. Vigreux column. After raking a precut (pot72° to 115° C., head 32° to 75° C., 0.35 to 0.20 mmHg), the diacetate fraction (pot 128° to 155° C., head 100° to 130° C., 0.45 mmHg) was collected. The yield was 196.6 g.

trans-2-Hydroxymethyl-1-cyclohexanol

The diol was prepared from the diacetate by transesterification. The diacetate (196 g) was dissolved in 500 mL methanol in a 1-L Erlenmeyer flask. To the magnetically stirred mixture was added slowly in small pieces 1.2 g metallic sodium. The mixture was a light yellow color with the odor of methyl acetate. Stirring was continued until all the sodium had reacted. The mixture was transferred to a 1-L round-bottom flask, and the methyl acetate/methanol components stilled off at atmospheric pressure (pot 62° to 115° C., head 55° to 75° C.). Upon cooling, the reaction mixture was neutralized with 2 to 3 mL acetic acid. After changing to water aspirator vacuum, the mixture was distilled through a four-plate Oldershaw column. A precut with the odor of formaldehyde was removed (pot 32° to 142° C., head 22° to 50° C., ~40 mmHg). After cooling somewhat, the distillation was continued using a mechanical pump vacuum and the diol fraction collected (pot 134° to 137° C., head 81° to 110° C., 135 to 0.4 mmHg). The yield was 99 g.

Dibutyltin trans-2-Hydroxymethyl-1-cyclohexanol Adduct

The dibutyltin intermediate was prepared by a synthetic procedure reported in the literature. The diol 4 (80.4 g, 0.61 moles) was dissolved in 1 L toluene and transferred to a three-neck, 2-L flask fitted with a mechanical stirrer, thermometer, Dean Stark trap with extension adapter, and a reflux condenser. To the stirred reaction mixture was added 153.8 g 98% purity di-n-butyltin oxide, (Bu)$_2$SnO. The mixture was then heated to reflux to azeotrope off the water of reaction. Initially, considerable foaming resulted and care was taken to prevent overflow into the Stark trap. The last traces of H$_2$O were slowly removed at reflux (4 to 5 hr); total H$_2$O collected: ~11 mL. The mixture (a deep orange-brown color) was cooled to room temperature.

trans/trans-2,3,8,9-di(Tetramethylene)-1,5,7,11-tetraoxaspiro[5.5]undecane

The reaction flask containing the dibutyltin intermediate was fitted with an addition funnel and cold finger condenser (dry ice, acetone). Over a period of 2 hr, 38 to 39 mL of CS$_2$ was added dropwise to the stirred mixture. After addition was completed, the reaction flask was refitted with a thermometer and reflux condenser and heated at reflux (105–110° C.) for about 21 hr. After cooling to room temperature, toluene excess CS$_2$ were stripped off using a rotary evaporator with water aspirator and then mechanical pump. The stripped residue was then distilled at reduced pressure. After removal of a small precut, the main product fraction was collected (pot 187° to 220° C.; head 170° to 205° C., 0.125 to 0.1 mmHg). The yield of crude product, a clean colorless oil was 83.65 g. The distilled product was recrystallized twice from hexane (1 g/mL) to obtain the final product. DSC 86.6° C.; $^1$H NMR (300 MHz, CDCl$_3$) δ 3.2 to 4.0 (m, 6H), 1.8 to 2.0 (m, 10H), 1.45 to 1.6 (m, 1H), 1.2 to 1.45 (m, 6H), 0.8 to 1.0 (m, 1H); $^{13}$C NMR (75 MHz, CDCl$_3$) δ 115.08, 76.32, 76.26, 75.34, 75.22, 67.52, 66.63, 66.52, 39.70, 39.65, 39.58, 31.16, 31.08, 25.55, 25.50, 25.47, 24.92, 24.40, 24.36, 24.26, 24.21; IR (photoacoustic) 2952, 2933, 2867, 1246, 1217, 1163, 1108, 1033, 927 cm$^{-1}$. Anal. calcd. for $C_{15}H_{24}O_4$; C, 67.14; H, 9.01. Found: C, 66.71; H, 8.98.

EXAMPLE 3 trans/trans-2,3,8,9-di(Tetramethylene)-1,5,7,11-tetraoxaspiro[5.5]undecane (DTM$_4$) (Alternate Procedure)

The subject spiroorthocarbonate has also been prepared from trans2-hydroxymethyl-1-cyclohexanol according to the following method, which is summarized in the following synthesis scheme, and based on a reported procedure.

A 1-L round bottom flask was charged with 65.7 g (0.505 mole) diol and 500 mL toluene, and fitted with a Dean-Stark trap, reflux condenser, and thermometer. The diol/toluene mixture was heated at reflux, with magnetic stirring, under N$_2$ for 1.5 hr to azeotrope off any water, and then allowed to cool to RT. Any toluene/water collected in the Dean-Stark trap was removed. p-Toluenesulfonic acid (PTSA, 0.1 g) and tetraethyl orthocarbonate (TEOC) (42.7 g, 0.222 mole) were added to the reaction flask, and the mixture was slowly warmed under N$_2$ to distill off the ethanol by-product. When the distillation temperature reached 110° C., the distillation apparatus was disconnected, and the reaction mixture was refluxed overnight (~16–18 hr) under N$_2$. After cooling to room temperature, the mixture was neutralized with triethylamine (1.5 to 2.0 mL), and the toluene distilled off under water aspirator pressure. After cooling to RT, the mixture was taken up to 500 mL hexanes and dried by stirring for 15 to 30 min with a 3 g mixture of 1:1 anhydrous MgSO$_4$: Magnesol. The mixture was filtered, and low boiling impurities were removed at reduced pressure, and the product was separated by simple distillation under high vacuum, yielding 48.5 g (81.5%) of an oil (bp=140–143° C. at 0.25 mmHg). The oil was crystallized from ~30 mL hexanes to give 28.2 g (47.4%) of the solid spiroorthocarbonate 3, m.p. by DSC=86.6° C. Yields of oil and solid are based on the theoretical amount of SOC expected from 0.222 moles of TEOC.

EXAMPLE 4 trans/trans-2,3,8,9-di(Hexamethylene)-1,5,7,11-tetraoxaspiro-[5.5]Undecane (DHM)

The sequence of synthetic reactions employed in the preparation of this spiroorthocarbonate is set forth in the following synthesis scheme.

2-Carboethoxycyclooctanone

The keto-ester was prepared by the sodium hydride induced acylation of cyclooctanone (1 using diethyl carbonate). A 1-L round bottom flask was charged with NaH (60% dispersion in mineral oil, 17.0 g, 708 mmol). The NaH was washed with three portions of toluene (200 mL), diethyl carbonate (36 mL, 207 mmol) was charged to the flask, and the reaction mixture warmed to 80° C. A solution of cyclooctanone (18.76 g, 149 mmol) in toluene (50 mL) was added dropwise over 1 hr. The temperature was maintained at 80° C. for 1.5 hr after the addition of cyclooctanone. Upon cooling to room temperature, glacial acetic acid (30 mL) was added dropwise, followed by ice water (200 mL). The reaction mixture was stirred until all the solid was in solution (additional water may be necessary). The layers were separated, and the aqueous layer was extracted with toluene (3×100 mL). The organic layer was dried over MgSO$_4$, filtered, and evaporated in vacuo to yield an oil. Purification was achieved by simple high vacuum distillation (91°–93° C. 0.5 to 0.6 mmHg) to yield 20.8 g, 71% of 6; IR (neat) 2950, 2870, 1745, 1710, 1640, 1617, 1468, 1382, 1330, 1250, 1230, 1185, 1100 cm$^{-1}$; $^1$H NMR (CDCl$_3$, 300 MHz) δ (keto-enol mix) 1.23 (t), 1.29 (t), 1.33 to 1.58 (m), 1.62 to 1.76 (m), 1.85 to 1.95 (m), 2.32 to 2.68 (m), 3.5 to 3.6 (m), 4.1 to 4.25 (m), 12.6 (s, enol H).

2-Carboethoxycyclooctanol

The hydroxy-ester was prepared by reduction of the keto-ester with sodium borohydride. A 100-mL round bottom flask was charged with keto-ester 2 (5.0 g 25.3 mmol) and ethanol (50 mL). The reaction mixture was stirred and NaBH$_4$ (1.0 g, 26.7 mmol) was added slowly. The reaction was stirred at RT for 1 hr and monitored by TLC (5:1 hexanes: ethyl acetate). The excess NaBH$_4$ was quenched by carefully adding acetic acid until no bubbles are evolved and pH is ~7. The reaction mixture was poured into EtOAc (250 mL) and washed with water (1×50 mL), followed by brine (1×50 mL). The organic layer was dried over MgSO$_4$, filtered and evaporated in vacuo. The remaining oil was subjected to high vacuum in order to remove the last traces of solvent. The crude oil (4.6 g) was taken on to the next step without further purification. Crude IR indicated reaction was successful. $^1$H NMR (CDCl$_3$, 300 MHz) δ (t, 3H), 1.40–2.50 (m, 12H), 2.7 (m, 1H), 2.8 (brs, 1H), 3.8 (m, 1H), 4.2 (q, 2H).

trans-2-Hydroxymethylcyclooctanol

The diol was prepared by reduction by the hydroxy-ester with lithium aluminum hydride. A 500-mL round bottom flask was charged with hydroxy-ester (4.6 g, 23 mL) and diethyl ether (150 mL) and blanketed with N$_2$. The mixture was cooled to –78° C. using a dry ice/isopropanol bath. Lithium aluminum hydride (1.0 g) was added slowly to the cooled solution. The reaction was allowed to warm to RT and was added slowly to the cooled solution. The reaction was allowed to warm to RT and stir overnight. The excess LiAlH$_4$ was quenched by first adding EtOAc (10 mL) followed by a saturated solution of Rochelle's salt (10 mL). CAUTION: the quench should be done slowly to avoid bubbling over. The reaction mixture was poured into a separatory funnel containing ethyl acetate (150 to 200 mL). The layers were separated and the organic layer was washed with water (1×25 mL), the brine (1×25 mL). The organic layer was dried over MgSO$_4$, filtered, and evaporated in vacuo to yield a colorless oil. High vacuum distillation (99°14 101° C. 0.2 mmHg) yielded 72% of the diol. IR (neat) 3320, 2910, 2850, 1468, 1446, 1034 cm$^{-1}$, $^1$H NMR, (CDCl$_3$, 300 MHz) δ 1.25 to 1.95 (m, 13H), 2.9 (s, 2H), 3.7 (m, 2H), 4.1 (m, 1H); $^{13}$C NMR (CDCl$_3$, 75 MHz) δ 22.08, 23.74, 25.45, 27.31, 27.42, 32.66, 41.65, 67.61, 73.18. Anal. Calcd. for C$_9$H$_{18}$O$_2$: C, 68.31; H, 11.46. Found: C, 68.84; H, 11.91.

trans/trans-2,3,8,9-di(Hexamethylene)-1,5,7,11-tetraoxaspiro[5.5)undecane

The spiroorthocarbonate was prepared by reaction of the dibutyltin/diol adduct with carbon disulfide. A 250-mL round bottom flask, blanketed with N$_2$, was charged with C$_8$-diol 4 (5.1 g, 31.6 mmol), toluene (100 mL), and dibutyltin oxide (7.9 g, 31.7 mmol). The reaction mixture was slowly warmed to reflux using a Dean-Stark trap to collect water. Azeotropic removal of water was continued overnight. The reaction mixture was cooled to RT then to 0° C. Carbon disulfide (1.9 mL, 31.6 mmol) was added to the reaction mixture dropwise using a syringe. Upon complete addition of carbon disulfide the reaction mixture was allowed to warm to RT followed by gentle heating to reflux. Reflux was continued overnight. The reaction mixture was cooled to RT. Toluene was removed in vacuo, and the remaining oil was purified by flash column chromatography using a 3.0 cm ID column. Hexane (500 mL+) was used to pack the column, load column, and collect some fractions.

The hexane was followed by 10:1 hexanes; EtOAc (1 L) as eluent. The fractions were evaporated in vacuo to yield 4.8 g of a clear oil which was taken up in 9 mL hexane and left in a refrigerator to crystallize. The 0.8 g of 6 was isolated, mp 103° to 105° C., and 4.0 g of oil were recovered ($R_f$ 2:1 hexanes: EtOAc; 0.59); IR(neat) 2930, 1471, 1452, 1231, 1214, 1161, 1130, 1058, 995 cm$^{-1}$; $^1$H NMR (CDCl$_3$, 300 MHz) δ 1.2 to 2.2 (m, 13H), 3.5 to 3.7 (m, 1H), 4.0 to 4.15 (m, 1H), 4.2 to 4.4 (m, 1H); $^{13}$C NMR (CDCl$_3$, 75 MHz) δ 22.59, 23.15, 24.93, 25.00, 25.81, 26.03, 26.47, 26.68, 28.25, 28.46, 29.13, 29.29, 36.24, 36.55, 68.88, 69.24, 73.99, 74.76, 119.59. Anal. Calcd. for $C_{19}H_{32}O_4$: C, 70.33; H, 9.94. Found: C, 70.06, H, 10.14.

Inspection of the DSC of the $C_8$-SOC 6, indicates that there are possibly two melting points. A study was conducted to determine if the difference was simply a difference in the conformation of the 8-membered ring. The $C_8$-SOC was heated on the DSC to ~150° C., which is about 25° C. above the first melting point. The compound was cooled and then heated against to 250° C. Note that the first melting point did not appear in the second run, supporting the speculation that the first peak was a different conformer. Upon cooling again, the compound was heated to 400° C. Note there is only one melting point. This study does not confirm different conformers, but it does support the theory.

EXAMPLE 5

2,8-Dimethyl-1,5,7,11-tetraoxaspiro[5.5]undecane (DM)

The synthetic sequence employed in the preparation of the dimethyl spiroorthocarbonate is set forth in the following synthesis schemes.

To a 500 mL three-necked round-bottomed flask, equipped with a reflux condenser, a Dean-Stark trap, a magnetic stir bar and a thermometer, was placed 1,3-butanediol 1 (20 mL, 99%, 0.2208 mole) and 350 mL of toluene under an atmosphere of nitrogen. The mixture was brought to reflux and maintained for 2 hours to azeotropically remove any moisture. The mixture was cooled to room temperature and then a catalytic amount of p-toluenesulfonic acid (PTSA, 0.35 g) was added. The resulting mixture was allowed to stir at room temperature until the solution turned clear. To this solution was then added tetraethylorthocarbonate (TEOC, 99.5%, 21.3 g, 0.1104 mol) and the reaction mixture was brought to reflux. The azeotropic mixture collected in the Dean-Stark trap was poured into salt water to determine the volume of EtOH that was generated. A total of 24.5 mL (theoretically, 25.9 mL) of EtOH was collected. TLC analysis (silica gel, 60% EtOAc/hexanes) revealed that the starting diol was completely consumed and that a new major spot ($R_f$ 0.59) indicated the formation of product. The reaction mixture was then quenched with 2.5 mL of triethylamine so that the solution was of pH 8–9. The mixture was concentrated using a rotary evaporator and dried under vacuum to give 21.2 g of oil was concentrated using a rotary evaporator and dried under vacuum to give 21.2 g of oil (pH~7). The crude material was purified by distillation through a Vigreaux distilling head (1:1 ratio) and the desired 2,8-dimethyl-1,5,7,11-tetraoxaspirol[5.5]undecane 2 (DM) was collected as colorless oil (74–75° C./0.3 mm-Hg) in 84.2% yield (a total of 17.6 g of oil, of which 1.0 g of white solid was separated). GC (150° C., 5 min, 20° C./min to 225° C.) analysis showed that these materials were mixture of three diastereomers (oil: 98.2% pure, 20.6% diastereomer 1, 60.3% diastereomer 2 and 17.3% diastereomer 3; solid 97.8% pure, 50.7% diastereomer 1, 20.9% diastereomer 2 and 26.2% diastereomer 3). $^1$H-NMR (CDCl$_3$, 300 MHz) δ 1.18–1.21 (q, 6H), 1.42.–1.49, 1.60–1.70 (2d, 4H), 3.895–3.92 (m, 4H), 4.16–4.28 (m, 2H); $^{13}$C-NMR (CDCl$_3$, 75 MHz) δ 21.02, 21.22, 31.23, 61.24, 61.36, 62.18, 62.30, 67.57, 67.66, 68.50, 68.69, 114.55; IR (neat) (cm$^{-1}$) 2960, 2920, 2880, 1230, 1150, 1135, 1090, 1080, 1010, 870.

EXAMPLE 6

2,8-Ditrifluoromethyl-1,5,7,11-tetraoxaspiro[5.5] undecane (DTFM)

The synthetic sequence employed in the preparation of this spiroorthocarbonate is set forth in the following synthesis schemes.

Ethyl 3-Hydroxy-4,4,4-trifluorobutyrate

To a 1000 mL three-necked round-bottom flask, equipped with a reflux condenser, a thermometer and a magnetic stir bar, was placed 36.8 g (99%, 0.2 mol) of 1,1,1-trifluoroacetoacetate and 400 mL of ethyl ether anhydrous (dried over 3 molecular sieves) under an atmosphere of $N_2$. The mixture was cooled to 0° C. and the 8.1 g of sodium borohydride (98%, 0.21 mol) was added in several portions over an hour such that the pot temperature was maintained at 2–3° C. The resulting mixture was allowed to slowly come to 5° C. and stirred for an additional hour. The cold bath was removed and the reaction mixture was allowed to stir at room temperature overnight. The reaction mixture was cooled to 10° C. and then neutralized by slow addition of 200 mL of 10% aqueous HCl solution. The resulting mixture was filtered and the organic phase separated. The aqueous phase was extracted with ethyl ether (3×75 mL). The organic phases were combined, swirled over anhydrous potassium carbonate (K$_2$CO$_3$), dried over anhydrous magnesium sulfate (MgSO$_4$) and concentrated under reduced pressure to yield 33.4 g (90%) of oil. The crude material was carried on to the subsequent reaction without further purification. IR (neat) (cm$^{-1}$) 3460, 2995, 2950, 1730, 1370, 1280, 1170, 1130, 1045, 1020, 950, 880.

2,4-Dihydroxy-1,1,1-trifluorobutane

To a 500 mL three-necked round-bottom flask, equipped with an additional funnel, a thermometer and a mechanical stirrer, was placed 12 g (95%, 0.3 mol) of lithium aluminum hydride suspended in 100 mL of ethyl ether anhydrous. The mixture was cooled to 0° C. and a solution of 33.4 g of ethyl 3-hydroxy-4,4,4-trifluorobutyrate in 100 mL of ethyl ether was then added dropwise over a period of 4 hours such that the reaction temperature was maintained at 0–5° C. The additional funnel was replaced with a reflux condenser and the resulting mixture was allowed to come to room temperature while stirring overnight. The reaction mixture was cooled to 0–5° C. and then neutralized to slow addition of 200 mL of 10% aqueous HCl solution. The resulting mixture was filtered and the organic phase separated. The aqueous phase was extracted with ethyl ether (3.75 mL). The organic phases were combined, dried over anhydrous magnesium sulfate and concentrated under reduced pressure to yield 18.5 g of oil. The crude material was purified by distillation via an Vigreux column to give 16.5 g (57.3%) product as a mixture of liquid and solid. Further purification by recrystallization from hexanes gave 6.6 g of crystals along with 5.1 g of liquid. Mp (DSC) 205.6° C.; $^1$H-NMR (CDCl$_3$, 300 MHz) δ 5.20 (s, 1H), 4.22–4.16 (m, 1H), 3.94–3.87 (m, 2H), 2.55 (s, 1H), 2.10–1.84 (m, 2H); $^{13}$C-NMR (CDCl$_3$, 300 MHz) δ 131.00–119.00 (q, J=1118.1 Hz), 69.80–68.40 (q, J=125.4 Hz), 59.55, 31.09; IR (KBr pellet) (cm$^{-1}$) 3380, 2980, 2900, 1435, 1390, 1320, 1280, 1170, 1135, 1050, Anal. Calcd for $C_4H_7F_3O_2$: C, 33.30; H, 4.91; F, 39.60, Found: C, 33.25; H, 4.92; F, 37.27.

2.8-Ditrifluoromethyl-1,5,7,11-tetraoxaspiro[5.5]undecane (DTFM 3)

To a 500 mL three-necked round-bottom flask, equipped with a Dean-Stark trap (20 mL), a reflux condenser, a thermometer and a magnetic stir bar, was placed 16 g (0.111 mol) of 2,4-dihydroxy-1,1,1-trifluorobutane (2) and 400 mL of toluene under an atmosphere of $N_2$. The mixture was brought to reflux and maintained at reflux temperature for 2 hours to azeotropically remove any moisture. About 100 mL (5×20 mL) of azeotropic mixture was collected in the Dean-Stark trap. The mixture was then allowed to slowly cool to room temperature and a catalytic amount (0.3 g) of anhydrous para-toluenesulfonic acid (PTSA) was added, followed by dropwise addition of 11.7 mL (0.056 mol) of tetraethylorthocarbonate (TEOC) The resulting mixture was brought to reflux to azeotropically remove ethanol generated during the reaction. The azeotropic mixture was shaken with salt water to determine the amount (volume) of ethanol collected. The reaction was monitored by GC (5 min at 105° C., 1 20° C./min rise to 225° C., 5 min at 225° C.) and/or TLC (silica gel, 1.5% ether/hexanes). After a total of 160 mL of azeotropic mixture (12.6 mL of ethanol) was collected, the reaction mixture was refluxed for an additional 2 hours and then allowed to stir at 102° C. overnight. The reaction mixture was allowed to slowly cool to room temperature and then neutralized by the addition of 1 mL of triethylamine. The resulting mixture was allowed to stir at room temperature for an additional half hour, dried over anhydrous magnesium sulfate, filtered and concentrated chromatography (silica gel, 10–15% ethyl ether/hexanes) to give clear crystals as a single diastereomer (21% yield) along with two portions (14% and 40% yields, respectively) of liquid as mixture of diastereomers (displayed the same pattern of mass fragmentation as the crystalline isomer by GC-MS analysis) containing by-products of which the structures were not identified. Mp (DSC) 122.4° C.; $^1$H-NMR (crystalline single diastereomer, $CDCl_3$, 300 MHz) δ 4.40–4.10 (m, 6H), 2.18–1.71 (m, 4H); $^{13}$C-NMR (crystalline single diastereomer, $CDCl_3$, 300 MHz) δ 128.74–117.56 (q, J=1108.5 Hz), 114.52, 70.80–69.44 (q, J=136.2 Hz), 61.21, 22.16; IR (crystalline single diastereomer, KBr pellet) ($cm^{-1}$) 3010, 2990, 2930, 1480, 1440, 1410, 1395, 1330, 1280, 1270, 1240, 1185, 1145, 1110, 1085, 1050, 1010, Anal. Calcd for $C_9H_{10}F_6O_4$: C, 36.50; H, 3.40; F, 38.49; Found: C, 36.50, H, 3.45; F, 36.09.

EXAMPLE 7

2,8-Diphenyl-1,5,7,11-tetraoxaspiro[5.5]undecane and 2,10-Diphenyl-1,5,7,11-tetraoxaspiro[5.5]undecane (DP)

These spiroorthocarbonates were synthesized by the sequence of preparative reactions shown in the following synthesis scheme.

3-Phenyl-2-oxa-1,5-pentanediol Diacetate

The diacetate was prepared by an established acetylation method. To 200 g (1.22 moles) of magnetically stirred 4-phenyl-1,3-dioxane in a 1-L round bottom (or Erlenmeyer flask) was added rapidly an acetylating mixture consisting of 200 g (1.95) moles) acetic anhydride and 1 g conc. $H_2SO_4$. A rapid exotherm to 65° to 70° C. persisting for ≈½ hr was observed with a yellow to brown discoloration. After stirring for several hours at room temperature, the reactants were allowed to stand overnight. The reaction mixture was neutralized with 4 g of sodium acetate, transferred to a 500-mL round bottom flask, and the excess acetic anhydride was distilled off using a water aspirator vacuum. The brown oily residue was then distilled using a mechanical pump vacuum and the clear, colorless diacetate 2 fraction boiling at 162° to 163W° C./3 mm was collected in a yield of 311 g (95% of theory). IR: 1735, 1365, 1230, 1120, 1035, 1010, 945, 755, 695 $cm^{-1}$. 1-Phenyl-1,3-propanediol The diol was prepared from the diacetate by transesterification. The diacetate (311 g) was dissolved in 600 mL methanol. To this magnetically stirred mixture was added slowly in small pieces 1.4 g of metallic sodium. Stirring was continued until all the sodium had been added. The mixture was a light yellow color with the odor of methyl acetate. This mixture was transferred to a 1-L round bottom flask and the methyl acetate/methanol components distilled off at a head temperature of 57° to 70° C. at atmospheric pressure. Upon cooling, the pot residue was neutralized with 10 mL acetic acid. Neutralized product was taken up in 3 volumes of anhydrous ether, treated with anhydrous $MgSO_4$ and Magnesol, filtered, and stripped on the rotovap at up to 75° C., and returned to a still pot. A precut with an odor of formaldehyde removed up to 100° C. with water aspirator vacuum. The residue was distilled under mechanical pump vacuum and the fraction boiling at 140° to 160° C./0.1 mm was collected. The yield of diol was 165.9 g (90% of theory). The product was a viscous yellow oil which was essentially one component via GC analysis. 1-Phenyl-1,3-propanediol dibutyltin adduct.

The dibutyltin intermediate was prepared by a synthetic procedure reported in the literature. Diol 3 (165.9 g, 1.09 moles) was dissolved in 1L toluene and transferred to a 3-neck, 2-L flask fitted with a mechanical stirrer, reflux condenser, thermometer, and a Dean Stark trap. To the stirred reaction mixture was added 277 g 98% purity (1.09 moles) of dibutyltin oxide. The mixture was then heated to reflux to azeotrope off the water of reaction. Initially considerable foaming resulted and care was taken to prevent overflow into the Dean Stark trap. The last traces of water were slowly removed at reflux to complete the formation of the dibutyltin adduct. A total of 19 mL was collected out of 19.6 mL theory.

2,8-Diphenyl-1,5,7,11-tetraoxaspiro[5.5]undecane and 2,10-Diphenyl-1,5,7,11-tetraoxaspiro[5.5]undecane The reaction flask containing was cooled to room temperature and fitted with a dropping funnel and a cold finger condenser (dry ice, acetone). Carbon disulfide (75 mL) was added dropwise to the stirred reaction mixture and slowly heated to reflux (~95° C.) approximately 1 hr. The coldfinger was replaced with a water condenser fitted with a drying tube, and refluxing was continued for an additional 3 hr. The final reflux temp was 100° C. The mixture was allowed to cool to room temperature, and the solvent and residual $CS_2$ stripped off on the rotary evaporator. The last residual toluene was removed with a mechanical pump attached to the rotary evaporator.

The viscous oily residue was extracted with boiling heptane. On cooling hard crystallites of the SOC were obtained; however, a viscous oil phase also separated. The extraction was repeated several times to obtain more SOC; however, an oil phase was always present. The first crystal crop was the purest and after one recrystallization from heptane, 25 g was obtained as a white hard crystalline mass (m.p. 109° to 111° C.). This product was analyzed by GC at 225° C. and found to be 97+% one component, which proved to be the 2,8-diphenyl isomer. To obtain an analytical sample of each isomer, 9 g of the crystalline material was stirred in heptane (90 mL) and heated for 30 min. Limited solubility was noted. After cooling to room temperature, the remaining solid was removed and the mother liquor placed in a crystallizing dish. The mother liquor was allowed to evaporate overnight at room temperature. A white crystalline material (0.4 g) and an oily residue (0.6 g) were isolated. The crystals were recrystallized from heptane to yield a rosette-shaped crystalline white solid. The solid isolated in the first recrystallization was subjected to several recrystallizations from heptane to yield a crystalline white solid.

2,8-Diphenyl-1,5,7,11-tetraoxaspiro[5.5]undecane: DSC 128.8° C.; $^1$H NMR (300 MHz, CDCl$_3$) δ 7.3 to 7.5 (m, 10H), 5.0 (dd, 2H), 4.5 to 4.6 (m, 2H), 4.10 to 4.20 (m, 2H), 2.0 to 2.2 (m, 2H), 1.7 to 1.8 (m, 2H); $^{13}$C NMR (75 MHz, CDCl$_3$) δ 140.84, 128.48, 127.93, 126.10, 115.51, 73.56, 62.73, 32.08; IR (photoacoustic) 3090, 3039, 2962, 2927, 1495, 1457, 1389, 1307, 1254, 1213, 1147, 1089, 1009, 861 cm$^{-1}$. Anal. calcd. for C$_{19}$H$_{20}$O$_4$: C, 73.06; H, 6.45. Found: C, 72.74; H, 6.37.

2,10-Diphenyl-1,5,7,11-tetraoxaspiro[5.5]undecane (5b): DSC 99.5° C.; $^1$H NMR (300 MHz, CDCl$_3$) δ 7.26 to 7.46 (m, 10H), 5.36 to 5.43 (dd, 1H), 5.01 to 5.38 (dd, 1H), 4.44 to 4.54 (m, 1H), 4.01 to 4.20 (m, 3H), 1.97 to 2.17 (m, 2H), 1.68 to 1.80 (m, 2H), $^{13}$H NMR (75 MHz, CDCl$_3$) δ 140.75, 140.56, 128.48, 128.29, 127.99, 127.74, 126.00, 125.80, 115.46, 74.28, 73.66, 61.68, 61.83, 32.18, 33.02; IR (photoacoustic) 3066, 3033, 3017, 2984, 2927, 1499, 1452, 1386, 1250,1201, 1150, 1078,1012, 962 cm$^{-1}$. Anal. calcd. for C$_{19}$H$_2$O$_4$; C, 73.06; H, 6.45. Found: C, 73.19; H, 6.33.

EXAMPLE 8

3,9-Diacetoxtmethyl-3,9-diethyl-1,5,7,11-tetraoxaspiro[5.5]undecane (DAMDE)

The sequence of synthetic reaction employed in the preparation of this spiroorthocarbonate is set forth in the following synthesis schemes.

The title TOSU was prepared via derivatization of the corresponding parent molecule, 3,9-diethyl-3,9-dihydroxymethyl-1,5,711-tetraoxaspiro[5.5]undecane (DEDHM 1), by treatment with acetic anhydride in the presence of pyridine. To a 250 mL round-bottomed flask was placed 3,9-diethyl-3,9-dihydroxymethyl-1,5,7,11-tetraoxaspiro[5.5]undecane (DEDHM 1, 5.0 g, 0.018 mol) and pyridine (25 mL) under an atmosphere of N$_2$. To this solution was added acetic anhydride (25.5 mL, 0.27 mol). The resulting mixture was allowed to stir at room temperature for 4 hours and the reaction progress monitored by TLC. The reaction mixture was then concentrated under reduced pressure using a rotary evaporator to give a viscous oil which crystallized upon standing in the refrigerator overnight. these crystals were further purified by recrystallization from cyclohexane (6.2 g of the crude product was dissolved in 30 mL of refluxing cyclohexane, and then allowed to slowly cool to room temperature). The crystals were collected by filtration, washed with cyclohexane (3×10 mL) and dried in vacuo. The desired 3,9-diacetoxymethyl-3,9-diethyl-1,5,7,11-tetraoxaspiro[5.5]undecane (DAMDE 2) was obtained as white crystals in 81% (5.3 g) yield. Mp (DSC) 71.4° C.; $^1$H-NMR (CDCl$_3$, 300 MHz) δ 0.79 (t, 6H), 1.33 (q, 4H), 2.02 (s, 6H), 3.71 (m, 4H), 3.79 (m, 4H), 4.14 (s, 4H); $^{13}$C-NMR (CDCl$_3$, 75 MHz) δ 7.04, 20.70, 23.29, 35.27, 63.34, 66.66, 67.05. 114.60, 170.68; FTIR-PAS (cm$^-$1) 2975, 2940, 2920, 2884, 1463, 1381, 1364, 1259, 1211, 1187, 1104, 1076, 1050, 1024, 1000, 969; Anal. Calcd. for C$^1$$_{17}$H$_{28}$O$_8$: C, 56.65; H, 7.83; Found: C, 56.89; H, 7.94.

EXAMPLE 9

3,9-Diethyl -3,9-dipropionyloxymethyl-1,5,7,11-tetraoxaspiro[5.5]undecane (DEDPM)

The sequence of synthetic reaction employed in the preparation of this spiroorthocarbonate is set forth in the following synthesis schemes.

The title TOSU was prepared via derivatization of the corresponding parent molecule, 3,9-diethyl-3,9-diethyl-3,9-dihydroxymethyl-1,5,7,11-tetraoxaspiro[5.5]undecane (DEDHM 1), by treatment with propionic anhydride in the presence of pyridine. To a 100 mL round-bottomed flask was placed 3,9-diethyl-3,9-dihydroxymethyl-1,5,7,11-tetraoxaspiro[5.5]undecane (DEDHM 1, 5.0 g, 0.018 mol) and pyridine (25 mL) under an atmosphere of N$_2$. To this solution was added propionic anhydride (34.8 mL, 0.27 mol). The resulting mixture was allowed to stir at room temperature for 4 hours and the reaction monitored by TLC. Pyridine and any unreacted propionic anhydride were removed by distillation under reduced pressure (note: the pot temperature should not exceed 40° C. during the distillation). The vicious residue was then dried in vacuo for 3 hours, which crystallized upon standing at room temperature. The resulting crystals were purified by recrystallization from cyclohexane (the crystals were dissolved in 18 mL of cyclohexane, allowed to slowly cool to room temperature and then kept in refrigerator overnight). The white crystals were collected by filtration, washed with cyclohexane (3×5 mL) and dried in vacuo. The desired 3,9-diethyl-3,9-dipropionyloxymethyl-1,5,7,11-tetraoxaspiro[5.5]undecane (DAMDE 2) was obtained as white crystals in 71.1% (5.0 g) yield. Mp (DSC) 68.1° C.; $^1$H-NMR (CDCl$_3$, 300 MHz) δ 0.81 (t, 6H), 1.11 (t, 6H), 1.35 (q, 4H), 2.32 (q, 4H), 3.73–3.81 (m, 8H), 4.15 (s, 4H); $^{13}$C-NMR )CDCl$_3$, 75 MHz) δ 7.10, 9.05, 23.38, 27.44, 35.42, 63.20, 66.74, 67.10, 114.66, 174.06; FTIR-PAS (cm$^{-1}$) 3543, 3524, 2957, 2940, 2913, 2883, 2859, 1738, 1460, 1382, 1363, 1262, 1223, 1215, 1190, 1157, 1121, 1083, 1070, 1009, 991, 957, 936; Anal. Calcd. for C$_{19}$H$_{32}$O$_8$: C, 58.75; H, 8.30; Found: C, 58.86; H, 8.53.

EXAMPLE 10

3,9-Diacetoxtmethyl-3,9-diphenyl-1,5,7,11-tetraoxaspiro[5.5]undecane (DAMDP)

The sequence of synthetic reaction employed in the preparation of this spiroorthocarbonate is set forth in the following synthesis schemes.

To a 100 mL round-bottomed flask was placed 3,9-dihydroxymethyl-3,9-diphenyl-1,5,7,11-tetraoxaspiro[5.5] undecane (CHMDP 1, 3.8 g, 0.01 mol) and pyridine (23 mL) under an atmosphere of N$_2$ (the starting DHMDP was not completely dissolved in pyridine). To the mixture was added acetic anhydride (14 mL, 0.15 mL) and the mixture became clear solution upon stirring. The reaction mixture was allowed to stir at room temperature for 3 hours and the reaction progress was monitored by TLC (2:3 Hexanes/EtOAc). The reaction mixture was then concentrated under reduced pressure using a rotary evaporator to give a viscous oil. The crude material was purified by column chromatography (silica gel, 30–50% hexanes/EtOAc; Note: the crude material was absorbed onto small amount of Silica get (~10 g) and then loaded onto a column (3.0 cm i.d.) packed with ~100 g of silica gel) to give 4.0 g of white viscous oil which was further purified by recrystallization from cyclohexane (the material was dissolved in 30 mL of refluxing cyclohexane and a sticky solid precipitated upon cooling to room temperature). The white solid was then collected by filtration, dried in vacuo to give the desired DAMDP 2 in 82.6% (3.8 g) yield. Mp (DSC) 31.0° C. (broad peak); $^1$H-NMR (CDCl$_3$, 300 MHz) δ 1.95 (s, 6H), 4.21 (s, 4H), 4.29 (d, 2H), 4.46 (d, 2H), 4.59 (s, 4H), 7.20–7.39 (m, 10H); $^{13}$C-NMR (CDCl$_3$, 75 MHz) δ 20.69, 39.17, 65.30, 66.63, 67.09, 114.25, 125.73, 128.68, 127.48, 138.41, 170.51;

FTIR-PAS (cm$^{-1}$) 2937, 1749, 1480, 1460, 1377, 1255, 1230, 1172, 1120, 1024, 964, 774, 709; Anal. Calcd. for $C_{25}H_{28}O_8$: C, 65.78; H, 6.18; Found: C, 58.85; H, 6.22.

EXAMPLE 11

5,5-Diethyl-19-oxadispiro [1,3-dioxane-2,2'-1,3-dioxane -5',4"-bicyclo [4.1.0]heptane ] (DECHE) (3,3-Diethyl-11,12-epoxy-1,5,7,16-tetraoxadispiro[5.2.5.2] hexadecane)

The synthetic sequence employed in the preparation of this epoxy spiroorthocarbonate is set forth in the following synthesis schemes.

5,5-Diethyl-1,3-dioxane-2-thione (1)

The thiocarbonate 1 was prepared by a variation of the thiocarbonylation procedure developed by Corey and Hopkins. To a three-necked round-bottomed flask, equipped with a mechanical stirrer and an additional funnel, was placed 2,2-diethyl-1,3-propanediol (15.86 g, 120 mmol), 4-dimethylaminopyridine (DMAP, 29.32 g, 240 mmol) and 120 mL of toluene under an atmosphere of nitrogen. The mixture was allowed to stir at room temperature until a homogeneous solution was reached. The mixture was cooled to 0–5° C. and then a solution of thiophosgene (9.43 mL, 120 mmol) in 90 mL of toluene was added dropwise via the additional funnel over a period of 90 min. This resulted in the formation of a bright orange DMAP-thiophosgene complex. After the completion of addition, the reaction mixture was allowed to stir for an hour at 0–5° C. and then slowly warmed to room temperature. The reaction mixture was allowed to stir at room temperature for an additional hour and then the precipitated DMAP-HCl salt was removed by filtration. The filtrate was concentrated under reduced pressure using a rotary evaporator. The crude material was purified by recrystallization (the crude material was dissolved in refluxing ether, allowed to cool to room temperature and slowly evaporated) or by column chromatography (silica gel, 2:1 methylene chloride/hexanes). The desired thiocarbonate 1 was obtained as white crystalline in 70% yield. Mp (DSC) 64.4° C. $^1$H-NMR (CDCl$_3$, 300 MHz) δ 4.17 (s, 4H), 1.51–1.43 (q, 4H, J=7.5 Hz), 0.92–0.87 (t, 6H, J=7.5 Hz); $^{13}$C-NMR (CDCl$_3$, 75 MHz) δ 189.53, 76.08, 33.67, 23.09, 6.97; IR (KBr pellet) (cm$^{-1}$) 2960, 2920, 1455, 1395, 1380, 1290, 1240, 1200, 1180, 1060, 990, 930, 720.

3,3-Dibutyl-2,4-dioxa-3-stannaspiro[5.5]undec-8-ene (2)

The tin adduct 2 and DECH 3 were prepared employing the procedures developed by Stansbury and Bailey. To a three-necked round-bottomed flask, equipped with a thermometer, a reflux condenser and a Dean-Start trap with an extension condenser, was placed a heterogeneous mixture of 2,2-cyclohexene-dimethanol (8.48 g, 59.6 mmol, purified by recrystallization from ethyl ether) and dibutyltin oxide (98%, 15.14 g, 59.6 mmol) in 250 mL of toluene. The mixture was brought to reflux and became clear solution. The reaction mixture was allowed to reflux for 3 hours while the liberated water was collected (with toluene) in the Dean-Stark trap (5×20 mL of the azeotropic mixture was collected). The Dean-Stark trap was removed and the reaction mixture was then allowed to reflux for additional 2 hours and then slowly cooled to room temperature under an atmosphere of nitrogen. The 3,3-dibutyl-2,4dioxa-3-stannaspiro[5.5]undec-8-ene 2 thus generated in situ was carried on to the subsequent reaction without further purification.

Note: The starting diol, 2,2-cyclohexene-dimethanol (98%, ACROS), needed to be purified prior to use, otherwise the reaction would fail to yield the desired tin adduct 2.

3,3-Diethyl-1,5,7,16-tetraoxadispiro[5.2.5.2]hexadec-11-ene (DECH 3)

To the above solution of 3,3-dibutyl-2,4-dioxa-3-stannaspiro[5.5]undec-8-ene 2 was added 5,5-diethyl-1,3-dioxane-2-thione 1 (10.39 g, 59.6 mmol) in several small portions at room temperature over a period of 20 min. The resulting mixture was allowed to stir at room temperature for 24 hours. The reaction was monitored by TLC (silica gel, 25% ether/hexanes). The reaction mixture was then concentrated under reduced pressure and the residue taken up with ethyl ether (white suspension formed upon standing). The ether solution was filtered and concentrated under reduced pressure to give light yellowish oil. The crude material was purified by column chromatography (silica gel, 10–15% ethyl ether/hexanes). The desired 3,3-diethyl-1,5,7,16-tetraoxadispiro[5.2.5.2]hexadec-11-ene (DECH 3) was obtained as colorless oil in 94% yield. $^1$H-NMR (CDCl$_3$, 300 MHz) δ 5.68–5.58 (m, 2H), 3.74–3.68 (4s, 8H), 2.08–1.94 (m, 4H), 1.63–1.56 (t, 2H, J=6.6 Hz), 1.46–1.37 (q, 4H, J=7.5 Hz), 0.84–0.76 (t, 6H, J=7.5 Hz); $^{13}$C-NMR (CDCl$_3$, 75 MHz) δ 126.03, 124.16, 114.68, 70.03, 69.32, 34.27, 30.50, 26.44, 23.14, 21.30, 13.92, 7.01; IR (neat) (cm$^{-1}$) 3020, 2960, 2880, 1640, 1450, 1360, 1250, 1220, 1200, 1185, 1160, 1105, 1020, 995, 920, 730, 655; Anal. Calcd for $C_{16}H_{26}O_4$: C, 68.06%; H, 9.28%; Found: C, 68.20%; H, 9.59%.

5,5-Diethyl-19-oxadispiro[1,3-dioxane-2,2'-1,3-dioxane-5',4"-[bicyclo[4.1.0]heptane] (DECHE 4) (3,3-Diethyl-11,12-epoxy-1,5,7,16-tetraoxadispiro[5.2.5.2] hexadecane)

The spiroorthocarbonate 4 was prepared employing the biphasic epoxidation procedure described by Anderson and Veysoglu due to the acid sensitive nature of this class of compounds. To a round-bottomed flask was placed 3,3-diethyl-1,5,7,16-tetraoxadispiro[5.2.5.2]hexadec-11-ene (DECH 3, 10.02 g, 35.4 mmol) and 350 mL of methylene chloride (CH$_2$Cl$_2$. To this solution was added 0.5 M aqueous solution of sodium bicarbonate (110 mL, pH ~8). The resulting biphasic mixture was allowed to stir vigorously at room temperature and then m-chloroperbenzoic acid (57–86% mCPBA, 9.00 g, ~35.77 mmol) was slowly added in several portions over a period of 30 minutes. The resulting mixture was allowed to stir for 5 hours at room temperature and the reaction progress was monitored by TLC (silica gel, 25% ether/hexanes). The two phases were separated and the organic phase was washed successively with 1 N aqueous NaOH (2×100 mL) and water 2×100 mL). The organic phases were combined, dried over anhydrous Na$_2$SO$_4$, and concentrated under reduced pressure to give an off-white solid. The crude material was washed with 5 mL of cold ether (pre-cooled at 0° C.) and purified by flash chromatography (silica gel, 15% ethyl ether/hexanes) or by recrystallization two times from diethyl ether/hexanes (the crude material was dissolved in refluxing ether, allowed to cool to room temperature and then hexanes was slowly added). The desired product DECHE 4 was obtained as white crystals in 90% yield. Mp (DSC) 67.4° C.; $^1$H-NMR (CDCl$_3$, 300 MHz, mixture of diastereomers) δ 3.70–3.50 (m, 8H), 3.16–3.04 (m, 2H), 2.08–1.92 (m, 2H), 1.80–1.60 (m, 2H), 1.44–1.18 (m, 6H), 0.86–0.70 (m, 6H), $^{13}$C-NMR (CDCl$_3$, 300 MHz, mixture of diastereomers) δ 114.53, 71.56, 69.45, 69.33, 68.98, 51.57, 50.07, 34.30, 31.43, 29.41, 29.29, 23.21, 23.09, 22.79, 19.86, 13.95, 7.07, 7.00; IR (KBr pellet) (cm$^{-1}$) 2970, 1455, 1365, 1255, 1225, 1205, 1180, 1110, 1060, 1020, 1000, 920, 810, 795, 780, 730; Anal. Calcd for $C_{16}H_{26}O_5$: C, 64.41; H, 8.78; Found: C, 64.86; H, 8.93.

5 wt % of the DECH in BDDGE/PTHF (80/20) dissolved by heating it at 80–85° C. for 20 min. By including DECH, the DECH/BDDGE/PTHF mixture is more reactive than BDDGE/PTHF (80/20) alone in parallel mixes with or without EDMAB. 5 wt % of the DECH in bis (epoxycyclopentyl ether) (BECPE) dissolved by heating it to 60° C. The mixture was more reactive than BECPE alone (induction time: 35 sec. vs. 56 sec.; peak max time: 77 sec. vs. 128 sec.) in parallel mixes with EDMAB. The mixtures were much less reactive without EDMAB (not complete with 20 min. irradiation). 10 wt % of the DECH in BECPE dissolved by heating it at 80–85° C. for 40 min. This mixture was more reactive than the above mixtures, which only contained 5 wt % DECH. The induction time was 23 sec. The peak max time was 47 sec. EDMAB was used.

The synthesis scheme for making DECHE is shown below:

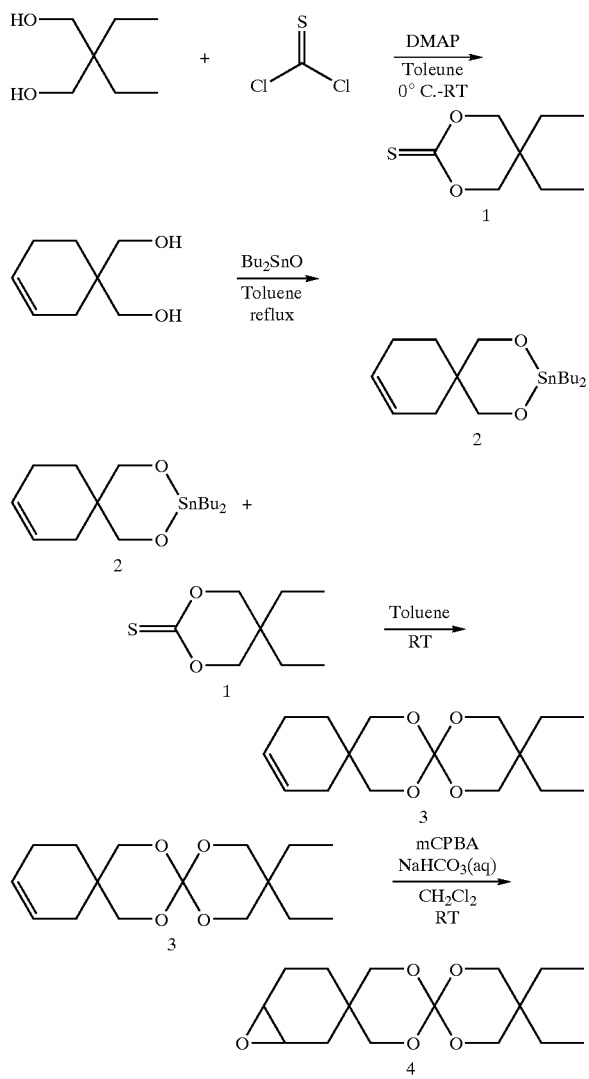

EXAMPLE 12

7,26-Dioxatrispiro [bicyclo [4.1.0]hephane 4,5'-1,3-dioxane -2',2''-1,3-dioxane-5'',3'''-bicyclo [4.1.0] heptane (DCHE)
(5,6:16,17-Diepoxy-1,10,12,21-tetraoxatrispiro[5.2.2.5.2.2] henicosane)

The synthetic sequence employed in the preparation of this epoxy spiroorthocarbonate is set forth in the following synthesis schemes.

8,10,19,20-Tetraoxatrispiro[5.2.2.5.2.2]henicosa-2,14-diene (DCH 2)

To a three-necked round-bottomed flask, equipped with a Dean-Stark trap (20 mL), a reflux condenser, a thermometer and a magnetic stir bar, was placed 2,2-cyclohexene-dimethanol 1 (15.78 g, 111 mmol) and 400 mL of toluene under an atmosphere of $N_2$. The mixture was brought to reflux and maintained at reflux temperature for 2 hours to azeotropically remove any moisture. About 100 mL (5×20 mL) of azeotropic mixture was collected in the Dean-Stark trap. The mixture was then allowed to slowly cool to room temperature and 0.3 g of anhydrous para-toluenesulfonic acid (PTSA) was added, followed by dropwise addition of tetraethylorthocarbonate (TEOC, 11.7 mL, 56 mmol). The resulting mixture was brought to reflux to azeotropically remove ethanol generated during the reaction. The azeotropic mixture was shaken with salt water to determine the amount (volume) of ethanol collected. The reaction was monitored by GC (5 min at 105° C., a 20° C./min rise to 225° C.) and/or by TLC (silica gel, 15% ether/hexanes). After a total of 160 m L of azeotropic mixture (12.3 mL of ethanol) was collected, the reaction mixture was allowed to reflux for an additional 2 hours and then allowed to stir at 102° C. overnight. The reaction mixture was allowed to slowly cool to room temperature and then neutralized by the addition of 1 mL of triethylamine. The resulting mixture was allowed to stir at room temperature for an additional 30 min, dried over anhydrous magnesium sulfate, filtered and concentrated under reduced pressure to give a light yellowish solid. The crude material was then purified by flash chromatography (silica gel, 15–25% ether/hexanes) or by recrystallization from refluxing ethyl ether/hexanes (v/v 1:1). The desired product 8,10,19,20-tetraoxatrispiro[5.2.2.5.2.2]henicosa-2,14-diene 2 (DCH) was obtained as white crystals in 80% yield. Mp (DSC) 118° C.; $^1$H-NMR (CDCl$_3$, 300 MHz) a 126.20, 124.29, 114.82, 70.21, 30.62, 26.56, 21.42; IR (KBr pellet) (cm$^{-1}$) 3020, 2920, 2850, 1630, 1440, 1365, 1250, 1225, 1190, 1100, 1025, 1000, 935, 920, 650; Anal. Calcd for $C_{16}H_{26}O_5$: C, 69.84; H, 8.27; Found: C, 69.68; H, 8.42.

7,26-Dioxatrisprio[bicyclo[4.1.0]heptane-4,5'-1,3-dioxane-2',2''-1,3-dioxane-5'',3'''-bicyclo[4.1.0]heptane (DCHE 3)
(5,6:16,17-Diepoxy-1,10,12,21-tetraoxatrispiro[5.2.2.5.2.2] henicosane)

The spiroorthocarbonate 3 was prepared employing the biphasic epoxidation procedure described by Anderson and Veysoglu due to the acid sensitive nature of this class of compounds. To a round-bottomed flask was placed a solution of 8,10,19,20-tetraoxatrispiro[5.2.2.5.2.2]henicosa-2,14-diene 2 (DCH-TOSU, 5.0 g, 17.1 mmol) in 250 mL of methylene chloride (CH$_2$Cl$_2$). To this solution was added 0.5 M aqueous solution of sodium bicarbonate (105 mL, pH ~8). The resulting biphasic mixture was stirred vigorously at room temperature and then m-chloroperbenzoic acid (57–86% mCPBA, 5.44 g, ~34.54 mmol) was slowly added in several portions over a period of 20 minutes. The resulting mixture was allowed to stir for 5 hours at room temperature and the reaction progress was monitored by TLC (silica gel, 25% ether/hexanes). The two phases were separated and the organic phase was washed successively with 1 N aqueous NaOH (2×75 mL) and water (2×75 mL). The organic phases were combined, dried over anhydrous Na$_2$SO$_4$, and concentrated under reduced pressure to give an off-white solid. The crude material was washed with 5 mL of cold ether (pre-cooled at 0° C.) and recrystallized two times from diethyl ether. The desired product DCHE 3 was obtained as white crystals in 90% yield. Mp (DSC) 184.65° C.; $^1$H-NMR (CDCl$_3$, 300 MHz, mixture of diastereomers) δ 3.70–3.44

(m, 8H), 3.16–3.04 (m, 4H), 2.12–1.15 (m, 12H); $^{13}$C-NMR (CDCl$_3$, 300 MHz, mixture of diastereomers) δ 114.34, 114.30, 71.71, 71.59, 71.47, 71.36, 69.11, 68.99, 68.95, 51.56, 50,05, 29.37, 29.32, 29.29, 29.23, 22.74, 19.82, 19.78; IR (KBr pellet) (cm$^{-1}$) 2920, 1440, 1365, 1250, 1225, 1200, 1100, 1000, 930, 860, 800, 780; Anal. Calcd for C$_{17}$H$_{24}$O$_6$: C, 62.95; H, 7.46; Found: C, 62.49; H, 7.26.

The synthesis scheme for making DCHE is shown below:

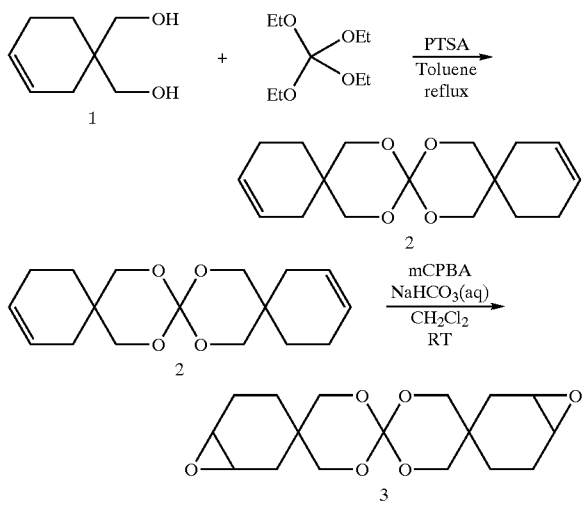

EXAMPLE 13

5,5-diethyl-18-oxadispiro[1,3-dioxane -2,2'-1,3-dioxane-5',3"bicyclo[3.1.0]hexane] (DECPE)
(11,11-Diethyl-2,3-epoxy-7,9,13,14-tetraoxadispiro [4.2.5.2]pentadecane)
(3,3-Diethyl-11,12-epoxy-1,5,7,15-tetraoxadispiro[5.2.4.2] pentadecane)

The synthetic sequence employed in the preparation of this epoxy spiroorthocarbonate is set forth in the following synthesis schemes.

5,5-Diethyl-1,3-dioxane-2-thione(1)

The thiocarbonate 1 was prepared in a variation of the thiocarbonylation procedure developed by Corey and Hopkins. To a three-necked round-bottomed flask, equipped with a mechanical stirrer and an additional funnel, was placed 2,2-diethyl-1,3-propanediol (15.86 g, 120 mmol), 4-dimethylaminopyridine (DMAP, 29.32 g, 240 mmol) and 120 mL of toluene under an atmosphere of nitrogen. The mixture was allowed to stir at room temperature until a homogeneous solution was reached. The mixture was cooled to 0–5° C. and then a solution of thiophosgene (9.43 mL, 20 mmol) in 90 mL of toluene was added dropwise via the additional funnel over a period of 90 min. This resulted in the formation of a bright orange DMAP-thiophosgene complex. After the completion of addition, the reaction mixture was allowed to stir for an hour at 0–5° C. and then slowly warmed to room temperature. The reaction mixture was allowed to stir at room temperature for an additional hour and then the precipitated DMAP-HCl salt was removed by filtration. The filtrate was concentrated under reduced pressure using a rotary evaporator. The crude material was purified by recrystallization (the crude material was dissolved in refluxing ether, allowed to cool to room temperature and slowly evaporated) or by column chromatography (silica gel, 2:1 methylene chloride/hexanes). The desired thiocarbonate 1 was obtained as white crystalline in 70% yield. Mp (DSC) 64.4° C.; $^1$.-NMR (CDCl$_3$ 300 MHz) δ 4.17 (s, 4H), 1.51–1.43 (q, 4H, J=7.5 Hz), 0.92–0.87 (t, 6H, J=7.5 Hz); $^{13}$C-NMR (CDCl$_3$, 300 MHz) δ 189.53, 76.08, 33.67, 23.09, 6.97; IR (Kbr pellet) cm$^{-1}$) 2960, 2920, 1455, 1395, 1380, 1290, 1240, 1200, 1180, 1060, 990, 930, 720.

Methyl 1-(Methoxycarbonyl)cyclopent-3-enecarboxylate (2)

(Dimethyl 3-Cyclopentene-1,1-dicarboxylate)

The dimethyl diester 2 was prepared employing Déprés and Greene's procedure. To a flame dried round-bottomed flask was placed dimethyl malonate (ACROS, 99+%, 26.7 g, 23.1 mL, 200 mmol) and anhydrous dimethylformamide (DMF, 300 mL). The mixture was cooled to 0° C. under an atmosphere of nitrogen while stirring. To this solution was then added lithium hydride (ACROS, 98%, 4.06 g, 500 mmol) powder in one portion. The resulting mixture was allowed to stir at 0° C. until the evolution of hydrogen ceased (~3 hours). To this heterogeneous mixture was then slowly added cis-1,4-dichloro-2-butene (ACROS, 95%, 30 g, 25.3 mL, 228 mmol). The resulting mixture was allowed to slowly come to room temperature and then allowed to stir for 72 hours (the color of the heterogeneous mixture changed from white to brown overnight). The reaction progress was monitored by TLC (silica gel, 20% ethyl ether/hexanes). The reaction mixture was diluted with 20% ethyl ether/hexanes (500 mL) and the solution poured into cold water (350 mL). The organic phase was separated, washed successively with water (300 mL) and brine (300 mL), dried over anhydrous sodium sulfate and concentrated under reduced pressure to give a light yellow solid. The crude material was recrystallized from refluxing hexanes (or ethyl ether). The desired dimethyl diester 2 was obtained as white needles in 50% yield. Mp (DSC) 63.48° C., 1H-NMR (CD$_{13}$, 300 MHz) δ 5.56 (s, 2H), 3.68 (2s, 6H), 2.97 (s, 4H); $^{13}$C-NMR (CDCl$_3$, 300 MHz) δ 172.47, 127.64, 58.60, 52.66, 40.78; FT-IR (CH$_2$Cl$_2$) (cm$^{-1}$) 3061, 2955, 1733, 1624, 1436, 1266, 1076, 975.

[1-(Hydroxymethyl)cyclopent-3-enyl]methan-1-ol (3)
(1,1-bis(Hydroxymethyl)-3-cyclopenene)

The desired diol was prepared via LAH reduction of the corresponding diester 2. To a flame dried round-bottomed flask was placed lithium aluminum hydride (LAH, Aldrich, 95%, 6.99 g, 175 mmol) and anhydrous tetrahydrofuran (THF, 235 mL). The resulting suspension was cooled to 0° C. and then a solution of the dimethyl diester 2 in 58 mL of anhydrous THF was added dropwise via an additional funnel. The resulting mixture was allowed to stir at 0° C. for 4 hours while monitored by TLC. The reaction mixture was then carefully quenched by sequential addition of 6 mL of water, 6 mL of 3 N aqueous solution of NaOH and 17.5 mL of water. The resulting mixture was allowed to slowly come to room temperature and then filtered through a bed of celite. The resultant solid cake was washed repeatedly with refluxing THF (total of 250 mL). The filtrate was dried over anhydrous sodium sulfate and concentrated under reduced pressure to afford alight yellow oil which was dissolved in 10 mL of refluxing toluene and the water was azeotropically removed. removal of the remaining toluene gave an off-white solid, which was recrystallized from refluxing toluene. The desired diol 3 was obtained as white needles in 86.2% yield, Mp (DSC) 81.21° C.; 1H-NMR (CD$_{13}$, 300 MHz) δ 5.59 (s, 2H), 3.73 (s, 2H), 3.63 (s, 4H), 2.16 (s, 4H); $^{13}$C-NMR (CD$_{13}$, 300 MHz) δ 128.69, 69.19, 47.53, 38.61; FT-IR (CH$_2$Cl$_2$) (cm$^{-1}$) 3323, 3055, 2918, 2846, 1619, 1442, 1419, 1357, 1266, 1114, 1093, 1025, 955, 909, 896.

8,8-Dibutyl-7,9-dioxa-8-stannaspiro[4.5]dec-2-ene (4)
(3,3-Dibutyl-2,4-dioxa-3-stannaspiro[5.4]dec-8-ene)

The tin adduct 4 and DECP 5 were prepared employing the procedures developed by Stansbury and Bailey. To a three-necked round-bottomed flask, equipped with a thermometer, a reflux condenser and a Dean-Stark trap with an extension condenser, was placed a heterogeneous mixture of [1-hydroxymethyl)cyclopent-3-enyl]methan-1-ol(3,7.73 g, 60.3 mmol) and dibutyltin oxide (Aldrich, 98%, 15.32 g, 60.3 mmol) in 250 mL of toluene. The mixture was brought to reflux and became clear solution. The reaction mixture was allowed to reflux for 3 hours while the liberated water was collected (with toluene) in the Dean-Stark trap (5×20 mL of the azeotropic mixture was collected). The Dean-Stark trap was removed and the reaction mixture was then allowed to reflux for additional 2 hours and then slowly cooled to room temperature under an atmosphere of nitrogen. The 8,8-dibutyl-7,9-dioxa-8-stannaspiro[4.5]undec-2-ene 4 thus generated in situ was subjected to the subsequent reaction without further purification.

11,11-Diethyl-7,9,13,14-tetraoxadispiro[4.2.5.2]pentadec-2-ene (DECP 5)
(3,3-Diethyl-1,5,7,15-tetraoxadispiro[5.2.4.2]pentadec-11-ene)

To the above solution of 8,8-dibutyl-7,9-dioxa-8-stannaspiro[4.5]dec-2-ene 4 was added 5,5-diethyl-1,3-dioxane-2-thione 1 (10.1 g, 60.3 mmol) in several small portions at room temperature over a period of 20 min. The resulting mixture was allowed to stir at room temperature for 24 hours. The reaction was monitored by TLC (silica gel, 25% ether/hexanes). The reaction mixture was then concentrated under reduced pressure and the residue taken up with ethyl ether (white suspension formed upon standing). The ether solution was filtered and concentrated under reduced pressure to give light yellowish oil. The crude material was purified by column chromatography (silica gel, 10–15% ethyl ether/hexanes). The desired 11,11-diethyl-7,9,13,14-tetraoxadispiro[4.2.5.2]pentadec-1-ene (DECP 5) was obtained as white solid in 72% yield. Mp (DSC) 95.19° C., $^1$H-NMR (CD$_{13}$, 300 MHz) δ 5.60 (s, 2H), 3.80 (s, 4H), 3.69 (s, 4H), 2.27 (s, 4H), 1.45–1.37 (q, 4H, J=7.8 Hz), 0.82–0.77 (t, 6H, J=7.8 Hz); $^{13}$C-NMR (CD$_{13}$, 300 MHz) δ 128.52, 114.39, 71.04, 69.48, 39.76, 34.33, 23.16, 7.12; FT-IR (Kbr pellet) (cm$^{-1}$) 3053, 2968, 1619, 1457, 1360, 1266, 1212, 1178, 1001, 938; Anal. Calcd for C1H24O4: C, 67.14; H, 901; Found: C, 67.44; H, 9.22.

5,5-Diethyl-18-oxadispiro[1,3-dioxane-2,2'-1,3-dioxane-5'3"-bicyclo[3.1.0]hexane] (DECPE 6)
(11,11-Diethyl-2,3-epoxy-7,9,13,14,-tetraoxadispiro[4.2.5.2]pentadecane)
(3,3-Diethyl-11,12-epoxy-1,5,7,15-tetroxadispiro[5.2.4.2]pentadecane)

The spiroorthocarbonate 6 was prepared employing the biphasic epoxidation procedure described by Anderson and Veysoglu due to the acid sensitive nature of this class of compounds. To a round-bottomed flask was placed 11,11-diethyl-7,9,13,14-tetraoxadispiro[4.2.5.2]pentadec-1-ene (DECP 5,2.65 g, 9.88 mmol) and 130 mL of methylene chloride (CH$_2$Cl$_2$). To this solution was added 0.5 M aqueous solution of sodium bicarbonate (3 mL, pH ~8). The resulting biphasic mixture was allowed to stir vigorously at room temperature and then mchloroperenzoic acid (Aldrich, 57.86% mCPBA, 2.74 g, ~10.87 mmol) was slowly added in several portions over a period of 30 minutes. The resulting mixture was allowed to stir overnight at room temperature and the reaction progress was monitored by TLC (silica gel, 50% ether/hexanes). The two phases were separated and the organic phase was washed successively with 1 N aqueous NaOH (2×100 mL) and water (2×75 mL). The organic phases were combined, dried over anhydrous Na$_2$SO$_4$, and concentrated under reduced pressure to give an off-white solid. The crude material was washed with 5 mL of cold ether (pre-cooled at 0° C.) and purified by flash chromatography (silica gel, 50% ethyl ether/hexanes) or by recrystallization two times from hexanes (the crude material was dissolved in refluxing hexanes, allowed to cool to room temperature and slow evaporization ). The desired produce DECPE 6 was obtained as white crystals in 81% yield. Mp (DSC) 93.16° C. 1H-NMR (CD$_{13}$, 300 MHz) δ 3.76–3.67 (3s, 8H), 3.50 (s, 2H), 2.14–2.09 (d, 2H, J=7.5 Hz), 1.58–1.54 (d. 2H, J=15 Hz), 1.44–1.36 (q, 4H, J=7.5 Hz), 0.82–0.77 (t, 6H, J=7.5 Hz); $^{13}$C-NMR (CD$_{13}$, 300 MHz) δ 114.24, 72.31, 71.27, 69.51, 57.61, 38.56, 34.81, 34.36, 23.17, 7.13; FT-IR (Kbr pellet) (cm$^{-}$1) 2968, 1483, 1460, 1422, 1365, 1266, 1255, 1221, 1205, 1181, 1110, 1060, 1024, 1004, 870, 837, 795, 762, 744; Anal. Calcd for C$_{15}$H$_{24}$O$_5$: C, 63.36; H, 8.51; Found: C, 63.60; H, 8.75.

The synthesis scheme for making DECPE is shown below:

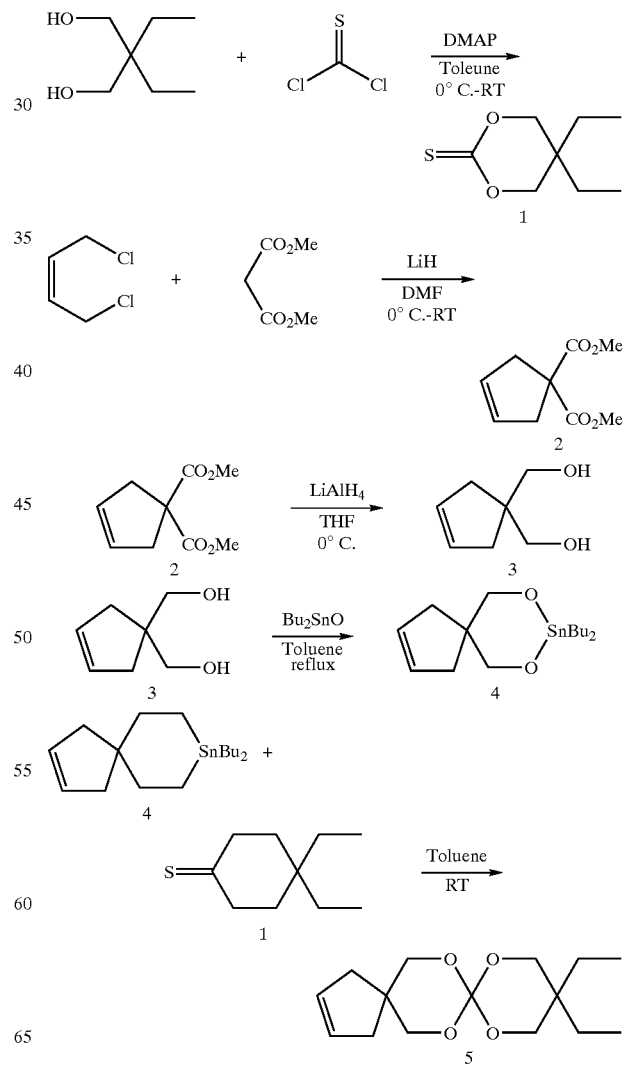

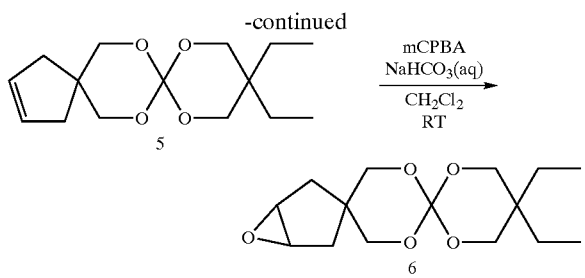

EXAMPLE 14

6,24-Dioxatrispiro[bicyclo[3.1.0]hexane-3,5'-1,3-dioxane-2'2"-1,3-dioxane-5"3'"-bicyclo[3.1.0]hexane (DCPE)

The synthetic sequence employed in the preparation of this epoxy spiroorthocarbonate is set forth in the following synthesis schemes.

Methyl 1-(Methoxycarbonyl)cyclopent-3-enecarboxylate (1)
(Dimethyl 3-Cyclopentene-1,1-dicarboxylate)

The dimethyl diester 1 was prepared employing Deprés and Greene's procedure. To a flame dried round-bottomed flask was placed dimethyl malonate (ACROS, 99+%, 26.7 g, 23.1 mL, 200 mmol) and anhydrous dimethylformamid (DMF, 300 mL). The mixture was cooled to 0° C. under an atmosphere of nitrogen while stirring. To this solution was then added lithium hydride (ACROS, 98%, 4.06 g, 500 mmol) powder in one portion. The resulting mixture was allowed to stir at 0° C. until the evolution of hydrogen ceased (~3 hours). To this heterogeneous mixture was then slowly added cis-1,4-dichloro-2-butene (ACROS, 95%, 30 g, 25.3 mL, 228 mmol). The resulting mixture was allowed to slowly come to room temperature and then allowed to stir for 72 hours (the color of the heterogeneous mixture changed from white to brown overnight). The reaction progress was monitored by TLC (silica gel, 20% ethyl ether/hexanes). The reaction mixture was diluted with 20% ethyl ether/hexanes (500 mL) and the solution poured into cold water (350 mL). The organic phase was separated, washed successively with water (300 mL) and brine (300 mL), dried over anhydrous sodium sulfate and concentrated under reduced pressure to give a light yellow solid. The crude material was recrystallized from refluxing hexanes (or ethyl ether). The desired dimethyl diester 1 was obtained as white needles in 50% yield. Mp (DSC) 63.48° C.; $^1$H-NMR (CDCl$_3$, 300 MHz) δ 5.56 (s, 2H), 3.68 (2s, 6H), 2.97 (s, 4H); $^{13}$C-NMR (CDCl$_3$, 300 MHz) δ 172.47, 127.64, 58.60, 52.66, 40.78; FT-IR (CH$^2$Cl$^2$) (cm$^{-1}$) 3061, 2955, 1733, 1624, 1436, 1266, 1076, 975.

[1-(Hydroxymethyl)cyclopent-3-enyl]methan-1-ol (2)
(1,1-bis(Hydroxymethyl)-3-cyclopentene)

The desired diol 2 was prepared via LAH reduction of the corresponding diester 1. To a flame dried round-bottomed flask was placed lithium aluminum hydride (LAH, Aldrich 95%, 6.99 g, 175 mmol) and anhydrous tetrahydrofuran (THF, 235 mL). The resulting suspension was cooled to 0° C. and then a solution of the dimethyl diester 1 in 58 mL of anhydrous THF was added dropwise via an additional funnel. The resulting mixture was allowed to stir at ° C. for 4 hours while monitored by TLC. The reaction mixture was then carefully quenced by sequential addition of 6 mL of water, 6 mL of 3 N aqueous solution of NaOH and 17.5 mL of water. The resulting mixture was allowed to slowly come to room temperature and then filtered through a bed of Celite. The resultant solid cake was washed repeatedly with refluxing THF (total of 250 mL). The filtrate was dried over anhydrous sodium sulfate and concentrated under reduced pressure to afford a light yellow oil which was dissolved in 150 mL of refluxing toluene and the water was azeotropically removed. Removal of the remaining toluene gave an off-white solid, which was recrystallized from refluxing toluene. The desired diol 2 was obtained as white needles in 86.2% yield. Mp (DSC) 81.21° C., $^1$H-NMR (CDCl$_3$, 300 MHz) δ 5.59 (s, 2H), 3.73 (s, 2H), 3.63 (s, 4H), 2.16 (S, 4H); $^{13}$C-NMR (CDCl$_3$, 300 MHz) δ 128.69, 69.19, 47.53, 38.61; FT-IR (CH$_2$Cl$_2$) (cm$_{-1}$) 3323, 3055, 2918, 2846, 1619, 1442, 1419, 1357, 1266 1114, 1093, 1025, 955, 909, 896.

7,9,17,18-Tetraoxatrispiro[4.2.2.4.2.2]nonadeca-2,13-diene (DCP 3)

To a three-necked round-bottomed flask, equipped with a Dean-Stark trap (20 mL), a reflux condenser, a thermometer and a magnetic stir bar, was placed diol 1 (14.8 g, 115.5 mmol) and 370 mL of toluene under an atmosphere of N$_2$. The mixture was brought to reflux and maintained at reflux temperature for 2 hours to azeotropically remove any moisture. About 100 mL (5×20 mL) of azeotropic mixture was collected in the Dean-Stark trap. The mixture was then allowed to slowly cool to room temperature and 0.2 g of anhydrous para-toluenesulfonic acid (PTSA) was added, followed by dropwise addition of tetraethylorthocarbonate (TEOC, 4563-91-2, 99.1%, 12.2 mL, 57.8 mmol). The resulting mixture was brought to reflux to azeotropically remove ethanol generated during this reaction. The azeotropic mixture was shaken with sale water to determine the amount (volume) of ethanol collected. After a total of 140 mL of azeotropic mixture (12.5 mL of ethanol) was collected, the reaction mixture was allowed to reflux for an additional 2 hours and then allowed to stir at 102° C. overnight. The reaction mixture was allowed to slowly cool to room temperature and then neutralized by the addition of 1 mL of triethylamine. The resulting mixture was allowed to stir at room temperature for an additional 30 min, and was stripped off solvents to give an off white solid. The crude material was then purified by flash chromatography (silica gel, CH$_2$Cl$_2$/hexanes 2/1 v/v) or by recrystallization from refluxing toluene. The desired product 7,9,17,18-tetroaxatrispiro[4.2.2.4.2.2]nonadeca-2,13-diene (DCP 3) was obtained as white crystals in 62% yield. Mp (DSC) 174.53° C.; $^1$H-NMR (CDCl$_3$, 300 MHz) δ 5.61 (s, 2H), 3.82 (s, 4H), 2.29 (s, 4H); $^{13}$C-NMR (CDCl$_3$, 300 MHz) δ 28.53, 114.14, 71.07, 39.79; FT-IR (CH$_2$Cl$_2$) (cm$^{-1}$) 3052, 2947, 2928, 2880, 2842, 1614, 1481, 1267, 1210, 1171, 1014, 990, 738, 671; Anal. Calcd for C$_{15}$H$_{20}$O$_4$: C, 68.16; H, 763; Found: C, 68.18; H, 7.81.

6,24-Dioxatrispiro[bicyclo[3.1.0]hexane-3-5'-1,3-dioxane-2'2"-1,3-dioxane-5"3'"-bicyclo[3.1.0[hexane] (DCPE 4)

The spiroorthocarbonate 4 was prepared employing the biphasic epoxidation procedure described by Anderson and Vesoglu due to the acid sensitive nature of this class of compounds. To a round-bottomed flask was placed a solution of 7,9,17,18-tetroxatrispiro[4.2.2.4.2.2]nonadeca-2, 13-diene (DCP 3, 4.3 g, 16.27 mmol) in 215 mL of methylene chloride (CH$_2$Cl$_2$). To this solution was added 0.5 M aqueous solution of sodium bicarbonate (113 mL, pH ~8). The resulting biphasic mixture was allowed to stir vigorously at room temperature and then m-chloroperbenzoic acid (Aldrich, 57–86% mCPBA, 8.6g, ~35.8 mmol) was slowly added in several portions over a period of 20 minutes. The resulting mixture was allowed to stir overnight at room temperature and the reaction progress was monitored by TLC (silica gel, 95% CH$_2$Cl$_2$/Et$_2$O, v/v). The two phases were separated and the organic phase was washed successively with 1 N aqueous NaOH (2×150 mL) and water (2×100 mL). The aqueous phase was back extracted with 100 mL CH$_2$Cl$_2$. The organic phases were combined, dried over anhydrous Na2SO$_4$, and concentrated under reduced pressure to give an off-white solid. The crude material was purified by flash chromatography (silica gel, 95% CH$_2$Cl$_2$/Et$_2$O, v/v). The desired produce DCPE 4 was obtained as white crystals in 75% yield. Mp (DSC) 256.55° C. $^1$H-NMR (CD$_{13}$, 300 MHz) δ 3.75–3.68 (m, 8H), 3.50 (s, 4H), 2.14–2.08 (dd, 4H, J=15 3 Hz), 1.58–1.53 (d, 4H, J=15 Hz); $^{13}$C-NMR (CD$_{13}$, 300 MHz) δ 113.76, 72.33, 71.29, 57.59, 38.54, 34.84, 34.75; FT-IR (CH$_2$Cl$_2$) (cm−1) 3012, 2945, 1486, 1434, 1266, 1210, 1105, 1047, 1019, 991, 830, 739; Anal. Calcd for C$_{15}$H$_{24}$O$_5$: C, 60.80; H, 6.80; Found: C, 60.55; H, 6.97.

The synthesis scheme for making DCPE is shown below:

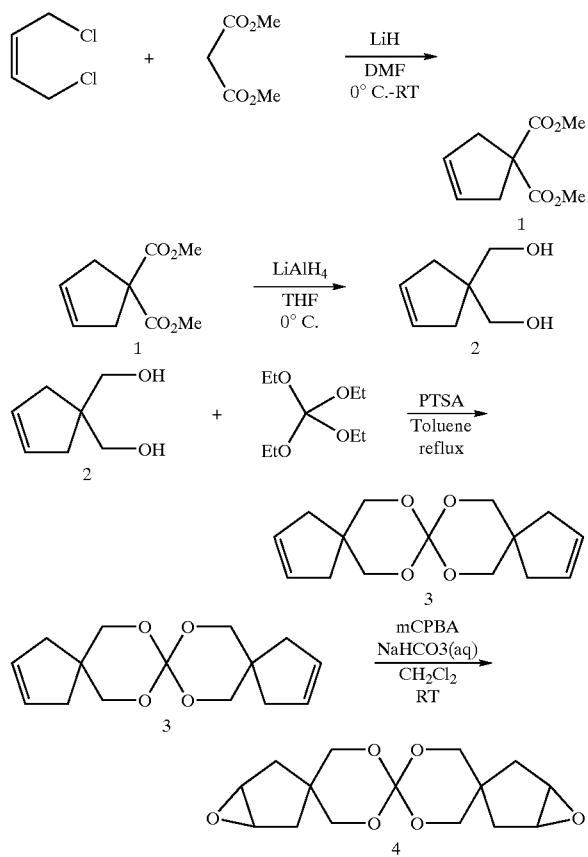

The photopolymerizable compositions of the invention are prepared by simply admixing, under "safe light" conditions, the components of the inventive compositions. Suitable inert solvents may be employed if desired when effecting this mixture. Any solvent may be used which does not react appreciably with the components of the inventive compositions and which does not substantially interfere with cationic cure of the composition at or below body temperature. Examples of suitable solvents include acetone, dichloromethane, and acetonitrile. A liquid material to be polymerized (at body temperature or less, if desired) may be used as a solvent for another liquid or solid material to be polymerized. Solventless compositions can be prepared by simply dissolving the aromatic iodonium complex salt, sensitizer, and donor in the vinyl ether based system with or without the use of mild heating to facilitate dissolution.

The compositions of the present invention provide a very useful combination of cure speed, cure depth and shelf life. They cure well even when loaded with large amounts of fillers, and can be used in a variety of applications including graphic arts imaging (e.g. for color proofing systems, curable inks, or silverless imaging), printing plates (e.g. projection plates or laser plates), photoresists, solder masks, electronic conformal coatings, coated abrasives, magnetic media, photocurable adhesives (e.g. for orthodontics) and photocurable composites (e.g., for autobody repair or dentistry).

The effectiveness of the vinyl ether/photoinitiator system of the present invention is illustrated by the following tables and examples. Tables 1 and 2 show that the time for polymerization of a vinyl ether is faster when a ternary photoinitiator system is included.

For the experiments reported in Table 1, 98.0 wt % ethylene glycol divinyl ether (EGDVE), 1.5 wt % (4-octyloxyphenyl)phenyliodonium hexafluoroantimonate (OPIA), and 0.5 wt % camphorquinone (CQ) were combined to make a resin. Various amounts of various electron donor compounds were added to the resin, as shown in Table 1. The resin was cured at 37° C. and at wavelengths greater than 418 nm for 20 minutes or until the reaction stopped (ca. 9 mW/cm$^2$, 11 mg sample size, 40 cc N$_2$/min). The results shown in Table 1 indicated that the preferred donor compounds are ethyl 4-(dimethylamino)benzoate (EDMAB), 4-dimethylaminobenzoic acid (4-DMABA), 3-dimethylaminobenzoic acid (3-DMABA), 4-dimethylaminobenzoin (DMAB), N-phenylglycine (NPG), 1,2,4-trimethoxybenzene (TMB), and 4-dimethylaminobenzaldehyde (DMABAL). EDMAB at 0.53 wt % resulted in an unresolved bimodal reaction exotherm profile. The first peak was the major peak, and the peak maxium time in Table 1 for this entry corresponds to this peak. 4-(Dimethylamino)phenethanol (4-DMAPE) at 0.1 wt % resulted in a baseline-resolved bimodal endotherm profile. The second peak reached a slightly higher heat flow value than the earlier peak. The peak maximum time in Table 1 for this entry corresponds to the second peak.

TABLE 1

COMPARISON OF THE POLYMERIZATION OF A VINYL ETHER WITH
VARIOUS ELECTRON DONOR COMPOUNDS AND WITHOUT A ELECTRON DONOR COMPOUND

| Reaction Promotor | Wt % Added to 1 Gram Resin | Induction Time (sec) | Time to Exotherm Peak Max. (sec) | Enthalpy ΔH (J/g) | Photoinduced Potential (mV) |
|---|---|---|---|---|---|
| None | 0.00 | 156 | 213 | 38 | −25 |
| Ethyl 4-(dimethylamino) benzoate (EDMAB) | 0.53 | 11 | 13 | 161 | 200 |
| Ethyl 4-(dimethylamino) benzoate (EDMAB) | 0.37 | 11 | 16 | 436 | 200 |
| Ethyl 4-(dimethylamino) benzoate (EDMAB) | 0.10 | 10 | 13 | 434 | 200 |
| 4-Dimethylaminobenzoic acid (4-DMABA) | 0.10 | 15 | 22 | 513 | 184 |
| 3-Dimethylamino benzoic acid (3-DMABA) | 0.10 | 19 | 30 | 382 | 115 |
| 1,2,4-Trimethoxybenzene (TMB) | 0.10 | 11 | 27 | 215 | 233 |
| 4-Dimethylaminobenzoin (DMAB) | 0.10 | 22 | 73 | 450 | 261 |
| N-phenylglycine (NPG) | 0.10 | 12 | 19 | 348 | 161 |
| 4-Dimethylaminobenzaldehyde (DMABAL) | 0.10 | 16 | 27 | 495 | 245 |
| 4-(Dimethylamino) phenethanol (4-DMAPE) | 0.10 | 38 | 280 | 480 | 17 |
| N,N-dimethylaniline (DMA) | 0.10 | 28 | 48 | 180 | 54 |
| Triethanolamine (TEA) | 0.10 | 91 | 109 | 10 | −162 |

The data in Table 1 shows significant rate enhancement with the use of certain electron donors in the system and inhibition may occur with others. The data further shows that the use of too much electron donor can slow the reaction rate.

For the experiments reported in Table 2, the photopolymerization of various vinyl ethers with and without the use of an electron donor to promote the reaction are reported. Data showing runs where EDMAB was used to promote the reaction are shown in parentheses after the numbers corresponding to runs without EDMAB. These results show using an electron donor compound, such as EDMAB, can promote polymerization of the various vinyl ethers and decrease the induction time and the time to the reaction's peak maximum relative to compositions not having an electron donor.

TABLE 2

VINYL ETHER HOMOPOLYMERIZATION PDSC

| Vinyl Ether | Enthalpy (J/g) | Induction Time (sec) | Time to Max. (sec) | Conversion at Max. (%) | Enthalpy (kcal/mole eq) | Rate Constant k (l/min) |
|---|---|---|---|---|---|---|
| EGDVE | 473 (371) | 52 (12) | 89 (14) | 50 (18) | 6.45 (5.06) | 3.6 (10.6) |
| DEGDVE | 539 33) | 58 (37) | 121 (113) | 44 (30) | 10.44 (6.39) | 1.3 (1.40) |
| TEGDVE | 417 (526) | 59 (17) | 70 (20) | 13 (19) | 10.07 (12.70) | 2.1 (11.1) |
| HDDVE | 537 (451) | 80 (51) | 139 (58) | 61 (23) | 9.25 (7.77) | 1.4 (15.5) |
| CHDMDVE | 330 (145) | 123 (30) | 204 (76) | 57 (24) | 7.74 (3.40) | 0.5 (2.8) |
| GVE | 797 (429) | 78 (56) | 284 (242) | 48 (51) | 9.53 (5.13) | 1.1 (0.8) |
| CEVE | ND | — | — | — | — | — |
| POMDO | ND | — | — | — | — | — |
| BDVE | 370 (371) | 381 (103) | 537 (176) | 34 (45) | 10.27 (10.30) | 1.1 (3.6) |

Notes:
OPIA/CQ 0.25/0.5 mole % based on moles of functional groups; 20 min. irradiation; 37° C.; 418 nm filter; 11.6 mW/cm2; sample size ≈ 11 mg.
With EDMAB runs in parentheses.

Table 3 also shows the effects of curing various vinyl ether compositions with and without an electron donor compound. The data shows that reaction rates are faster when an electron donor compound is used.

TABLE 3

PDSC PARAMETERS OF TEGDVE/ERL 4206 BASED MIXTURES CURED USING UV LIGHT, OR VISIBLE LIGHT WITH AND WITHOUT ELECTRON DONOR COMPOUND (EDMAB)

| Component | (Mole %) | $H_{photo}$ (J/g) | | | Induction Time (sec) | | | Time to Max. (sec) | | | Conversion at Max. (%) | | |
|---|---|---|---|---|---|---|---|---|---|---|---|---|---|
| | | $UV^a$ | $VIS^b$ | $VIS + E^c$ | $UV^a$ | $VIS^b$ | $VIS + E^c$ | $UV^a$ | $VIS^b$ | $VIS + E^c$ | $UV^a$ | $VIS^b$ | $VIS + E^c$ |
| ERL4206 | (50) | 642 | 590 | 600 | 7 | 169 | 30 | 9 | 562 | 86 | 14 | 59 | 17 |
| TEGDVE | (50) | | | | | | | | | | | | |
| ERL4206 | (45) | 400 | 507 | 494 | 6 | 191 | 27 | 10 | 324 | 60 | 19 | 22 | 8 |
| TEGDVE | (45) | | | | | | | | | | | | |
| PTHF | (10) | | | | | | | | | | | | |
| ERL4206 | (45) | 431 | 461 | 416 | 14 | 369 | 34 | 21 | 855 | 90 | 25 | 56 | 15 |
| TEGDVE | (45) | | | | | | | | | | | | |
| SOC DEDPM | (10) | | | | | | | | | | | | |
| ERL4206 | (40.5) | 364 | 378 | 362 | 12 | 328 | 38 | 19 | 577 | 79 | 25 | 30 | 17 |
| TEGDVE | (40.5) | | | | | | | | | | | | |
| PTHF | (9.0) | | | | | | | | | | | | |
| SOC DEDPM | (10.0) | | | | | | | | | | | | |

$^a$UV = 285–445 nm; 50 mW/cm2
$^b$VIS = >418 nm; 5 mW/cm2
$^c$VIS + E = Same as VIS only 0.1 wt % EDMAB added to mixtures.
Note:
Mixes on a mole equivalent basis; [OH]/[epoxy] = constant; temp = 37° C.; CD 1012/CQ = 0.25/0.5 mole %

Examples 15, 16 and 17 further illustrate the importance of including an electron donor compound in the present invention. These examples show the variation in gel time when an electron donor compound is included compared with when no donor compound is included.

EXAMPLE 15

Ternary Photoinitiator System for Curing Vinyl Ether Resin Compositions

A stock solution ("SL1") of a vinyl ether mixture was prepared by combining 15 grams of VECTOMER 2020 (Allied Signal) and 15 grams VECTOMER 4010 (Allied Signal) and stirring until homogeneous.

Two photoinitiator systems were evaluated in SL1 for cure speed. Two compositions were prepared as follows:

| Composition A | |
|---|---|
| SL1 | 9.50 g |
| Camphorquinone | 0.05 g |
| Diphenyliodonium hexafluoroantimonate | 0.15 g |
| Composition B | |
| SL1 | 9.80 g |
| Camphorquinone | 0.05 g |
| Diphenyliodonium hexafluoroantimonate | 0.15 g |
| 4-Dimethylaminobenzoic acid | 0.05 g |

Each composition was prepared by combining the ingredients at room temperature and stirring until homogeneous. Samples were evaluated for cure speed according to the following procedure. Previously prepared molds made from 2-mm thick "Teflon" sheet with a 4-mm diameter hole through the sheet were clamped to a square of clear polyester film. The hole was filled with a vinyl ether composition and then irradiated at a distance of 10 mm with a Visilux 2 (3M) dental curing light. The light source provided approximately 300–400 mw/cm$^2$ of energy between 400 and 500 nanometers. Irradiation continued for 120 seconds or until a soft or hard gel was formed. Results are reported below.

| Composition | Donor | Gel Time |
|---|---|---|
| A | None | No Cure |
| B | DMABA | 50 seconds |

The data illustrates that a vinyl ether composition can be rapidly photopolymerized when the electron donor 4-dimethylaminobenzoic acid (DMABA) is used in combination with the photosensitizer camphorquinone and proton source diphenyliodonium hexafluoroantimonate. No curing was observed in the absence of the donor DMABA.

EXAMPLE 16

Ternary Photoinitiator System for Curing Vinyl Ether Resin Compositions

Five photoinitiator systems were evaluated in the bis hydroxybutyl vinyl ether isophthalate; (VECTOMER 4010 (Allied Signal)) for cure speed. Five compositions were prepared as follows:

| Composition A | |
|---|---|
| VECTOMER 4010 | 9.80 g |
| Camphorquinone | 0.05 g |
| Diphenyliodonium hexafluoroantimonate | 0.15 g |
| Composition B | |
| VECTOMER 4010 | 9.80 g |
| Camphorquinone | 0.05 g |
| Diphenyliodonium hexafluoroantimonate | 0.15 g |
| Ethy 4-dimethylaminobenzoate (EDMAB) | 0.05 g |

-continued

| Composition C | |
|---|---|
| VECTOMER 4010 | 9.80 g |
| Camphorquinone | 0.05 g |
| Diphenyliodonium hexafluoroantimonate | 0.15 g |
| 4-Dimethylaminobenzoic acid (DMABA) | 0.05 g |
| Composition D | |
| VECTOMER 4010 | 9.80 g |
| Camphorquinone | 0.05 g |
| Diphenyliodonium hexafluoroantimonate | 0.15 g |
| N-phenylglycine (NPG) | 0.05 g |
| Composition E | |
| VECTOMER 4010 | 9.80 g |
| Camphorquinone | 0.05 g |
| Diphenyliodonium hexafluoroantimonate | 0.15 g |
| N,N-Dimethylaniline (DMA) | 0.05 g |

Each composition was prepared by combining the ingredients at room temperature and stirring until homogeneous. Samples were evaluated for cure speed according to the procedure of Example 1. Results are reported below.

| Composition | Donor | Gel Time | Comments |
|---|---|---|---|
| A | None | 115 sec | slight surface cure |
| B | EDMAB | 25 sec | exotherm/color |
| C | DMABA | 25 sec | exotherm |
| D | NPG | 70 sec | |
| E | DMA | No cure | |

The data illustrates that the vinyl ether VECTOMER 4010 can be rapidly photopolymerized when several low basicity electron donor compounds are used in combination with the photosensitizer camphorquinone and proton source diphenyliodonium hexafluoroantimonate. Limited photocuring was observed in the absence of the electron donors or in the presence of the higher basicity electron donor DMA.

EXAMPLE 17

A variety of visible light absorbing sensitizers were evaluated in vinyl ether formulations containing approximately 1.50% diphenyliodonium hexafluoroantimonate (DPISbF$_6$), 0.50 sensitizer compound and optionally 0.50% EDMAB by weight. Solutions A and B without and with EDMAB respectively were prepared as shown below:

| Ingredient | Parts by weight |
|---|---|
| Solution A | |
| VECTOMER 4010 | 100.00 |
| Diphenyliodonium hexafluoroantimonate | 1.50 |
| Solution B | |
| VECTOMER 4010 | 100.00 |
| Diphenyliodonium hexafluoroantimonate | 1.50 |
| 4-Dimethylaminobenzoic acid | 0.50 |

Sensitizers were evaluated by transferring 0.0020 grams of the sensitizer to a 2 dram glass vial followed by the addition of 2 drops dichloromethane solvent and 1.0 grams of solution A. Compositions were mixed until homogeneous and evaluated for gel time as described below. One drop of each vinyl ether composition was applied to a clear 1 cm×1 cm square of clear polyester film. Samples were irradiated with a "GE Light Engine" (a white light source available from General Electric) or alternatively with a Visilux dental curing light (available from 3M), where indicated by an * in the table below. The samples were irradiated at a distance of about 5–6 centimeters and were probed to establish gel times up to a maximum of 90 seconds. Samples were also examined for initial color and any observable color change. The same procedure was repeated for solution B. Set out below are the sensitizer, the gel times with and without EDMAB and any key observations.

| | Gel Time (seconds) | | |
|---|---|---|---|
| Sensitizer | No EDMAB | With EDMAB | Comments |
| None | No Cure | No Cure | |
| Camphorquinone | No Cure | 20 | |
| Rose bengal | No Cure | 35 | red to yellow |
| Rose bengale | No Cure | 63 | red to yellow |
| Acridine Orange | 45 | 15 | * Visilux light |
| Malachite Green | No Cure | 55 | |
| Methylene Blue | No Cure | 43 | blue to yellow |
| Toluidine Blue | 81 | 32 | blue to yellow |
| Safranine O | 25 | 11 | * Visilux light orange to yellow |
| 4,5-dibromofluorescein | 31 | 23 | orange to yellow |

Examples 15–17 show a variety of vinyl ether systems that contain a ternary photoinitiator system. The data shows that use of an electron donor as part of the ternary photoinitiator system shortens reaction time. Still further, the data illustrates that an array of visible light sensitizers, in combination with DPISbF$_6$ and the electron donor EDMAB, photocures faster than those formulations with sensitizer and DPISbF$_6$ alone.

EXAMPLE 18

The effect of an electron donor compound on the photohomopolymerization of selected vinyl ethers is further illustrated by the graph in FIG. 1. A*, B*, and C* show the photopolymerization of certain vinyl ethers containing 0.1 wt % of the electron donor compound ethyl 4-dimethylaminobenzoate (EDMAB). A, B, and C show the polymerization of certain vinyl ethers with no electron donor compound. Specifically, A and A* show the effect of an electron donor compound on ethylene glycol divinyl ether (EGDVE). B and B* show the effect of an electron donor compound on tri(ethylene glycol) divinyl ether (TEGDVE). C and C* show the effect of an electron donor compound on hexanediol divinyl ether (HDDVE). The OPIA/CQ equaled 0.25/0.5 mole % based on moles of vinyl groups. The experiments illustrated in FIG. 1 were performed at 37° C., at wavelengths greater than 418 nm, and 11.6 mW/cm$^2$.

A substantial amount of vinyl ether is used in all of the photopolymerizable compositions of the present invention. The term "substantial amount of vinyl ether" means that of all the polymerizable components in the composition, vinyl ether is present in the greatest amount. Thus, a composition that has a substantial amount of vinyl ether is predominately vinyl ether. Preferably, any matrix that is formed from the compositions of the present invention is primarily defined by vinyl ether.

The use of vinyl ether as the substantial component of the formulations of the present invention provides several advantages. Compositions that include a substantial amount of vinyl ether with an SOC provide a matrix for taking advantage of the potential volume expansion properties of SOCs. Because most SOCs are solids at room temperature and are polymerizable to any significant extent only at elevated temperatures over extended time periods, polymerized SOCs result in polymers that have relatively poor physical properties. By creating mixtures of vinyl ethers, SOCs, and a photoinitiator system, polymerization can occur at room temperature. Data from the photopolymerization of various vinyl ether/SOC compositions of the present invention is shown in Tables 4 and 5.

TABLE 4

VE/TOSU PHOTOPOLYMERIZATION COMPOSITIONS AND RESULTS

| No. | VE | TOSU | Wt. % | PI | Wt. % | RP | WT. % | $\Delta H_{theory}$ (J/g) | $\Delta H_{EXPER}$ (J/g) | Reacted (%) | Ind. Time (sec) | Peak Max (sec) | $\Delta H_{exper}$ at Max. (%) |
|---|---|---|---|---|---|---|---|---|---|---|---|---|---|
| 1 | TEGDVE | DEDPM | 25 | CE1012 | 0.5 | — | — | 438 | 392 | 89 | 91 | 137 | 16 |
| 2 | TEGDVE | DEDPM | 25 | CD1012 | 0.5 | EDMAB | 0.1 | 438 | 380 | 87 | 29 | 33 | 18 |
| 3 | TEGDVE | DEDPM | 25 | RHO2074 | 0.5 | — | — | 439 | 382 | 87 | 109 | 141 | 21 |
| 4 | TEGDVE | DEDPM | 25 | RHO2074 | 0.5 | EDMAB | 0.1 | 439 | 393 | 90 | 31 | 37 | 22 |
| 5 | TEGDVE | DECHE | 25 | CD1012 | 0.5 | — | — | 516 | 348 | 67 | 130 | 235 | 35 |
| 6 | TEGDVE | DECHE | 25 | CD1012 | 0.5 | EDMAB | 0.1 | 515 | 428 | 83 | 39 | 71 | 31 |
| 7 | TEGDVE | DTM | 25 | OPIA | 0.5 | — | — | 464 | 321 | 69 | 50 | 91 | 8 |
| 8 | GVE | DEDPM | 25 | OPIA | 0.5 | — | — | 1139 | 221 | 19 | 207 | 754 | 61 |
| 9 | GVE | DECHE | 25 | CD1012 | 0.5 | — | — | 1218 | 210 | 17 | 117 | 366 | 34 |
| 10 | GVE | DECHE | 25 | CD1012 | 0.5 | EDMAB | 0.1 | 1218 | 232 | 19 | 36 | 232 | 30 |
| 11 | GVE | DECHE | 25 | RHO2074 | 0.5 | — | — | 1219 | 245 | 20 | 170 | 558 | 45 |
| 12 | GVE | DTM | 25 | OPIA | 0.5 | — | — | 1139 | 94 | 8 | 177 | 479 | 37 |
| 13 | HDDVE | DEDPM | 25 | OPIA | 0.5 | — | — | 520 | 194 | 37 | 506 | 659 | 33 |
| 14 | HDDVE | DEDPM | 25 | OPIA | 0.5 | EDMAB | 0.1 | 520 | 498 | 96 | 30 | 46 | 14 |
| 15 | HDDVE | DECHE | 25 | CD1012 | 0.5 | — | — | 600 | — | — | — | — | — |
| 16 | HDDVE | DM | 25 | CD1012 | 0.5 | — | — | 520 | — | — | — | — | — |

Notes:
All runs contained 1 wt % CQ as the photosensitizer; Reaction not completed after standard 20 minutes irradiation.

Table 4 shows that when an electron donor, such as EDMAB, is used, the polymerization proceeds quicker and the polymer is more completely cured. This table further shows that certain vinyl ether/SOC combinations are more reactive than others.

TABLE 5

VE/TOSU PHOTOPOLYMERIZATE PRODUCTS

| No. | Wt. Lost | Description of Post PDSC Product |
|---|---|---|
| 1 | 0 | Colorless clear elastomeric gel; no resistance to puncture |
| 2 | 0.2 | Black center, dark brown, soft brittle disk |
| 3 | 1.2 | Dark brown center, yellow-brown flexible removable disk |
| 4 | 0.2 | Brown black brittle easily crumbled disk |
| 5 | 0 | Elastomeric solid, tacky surface |
| 6 | 0 | Yellow, hard, can be scratched |
| 7 | 0 | Cured hard, can be scratched |
| 8 | 4.7 | Soft elastomeric gel |
| 9 | 3.3 | Brittle, crumbled easily |
| 10 | 4.0 | Brittle, crumbled easily |
| 11 | 3.2 | Clear, brittle, easily crumbled, somewhat elastomeric |
| 12 | 5.9 | Skin on top, still liquid below surface |
| 13 | 1.1 | Soft, semi-gel |

TABLE 5-continued

VE/TOSU PHOTOPOLYMERIZATE PRODUCTS

| No. | Wt. Lost | Description of Post PDSC Product |
|---|---|---|
| 14 | 0.6 | Clear, tough, flexible, removable disk |
| 15 | 0 | Liquid, no change |
| 16 | 0.1 | Liquid, no change |

Table 5 includes data that shows that less weight is lost when an electron donor is used in the composition, which indicates a more complete conversion of the reaction materials.

The vinyl ether/epoxide/polyol polymerizable composition of the present invention includes a substantial amount of vinyl ether. By using an epoxide with a vinyl ether, the physical properties of the vinyl ether are improved. Data from the photopolymerization of various vinyl ether/epoxide/polyol compositions is shown in Tables 6A, 6B, and 6C. The numbers shown in parentheses show data where an electron donor was present. The reaction proceeded faster when an electron donor was used.

TABLE 6A

VINYL ETHER/DIEPOXIDE/POLYOL PHOTOPOLYMERIZATIONS: SERIES 1A (UVR6105)

| No. | Vinyl Ether | Enthalpy (J/g) | Induction Time (sec) | Time to Max. (sec) | Conversion at Max (%) | Enthalpy (kcal/mole eq) |
|---|---|---|---|---|---|---|
| 17 | EGDVE | 230 | 137 | 287 | 20 | 4.56 |
| 18 | DEGDVE | NC | — | — | — | — |
| 19 | TEGDVE | 345 (353) | 76 (16) | 121 (33) | 12 (15) | 9.55 (9.77) |
| 20 | HDDVE | NC | — | — | — | — |
| 21 | CHDMDVE | 189 | 106 | 184 | 24 | 5.12 |
| 22 | GVE | 270 (320) | 60 (14) | 102 (24) | 19 (22) | 5.84 (6.92) |

TABLE 6A-continued

VINYL ETHER/DIEPOXIDE/POLYOL PHOTOPOLYMERIZATIONS: SERIES 1A (UVR6105)

| No. | Vinyl Ether | Enthalpy (J/g) | Induction Time (sec) | Time to Max. (sec) | Conversion at Max (%) | Enthalpy (kcal/mole eq) |
|---|---|---|---|---|---|---|
| 23 | POMDO | NC | — | — | — | — |
| 24 | BDVE | 351 (418) | 233 (23) | 376 (47) | 53 (35) | 10.33 (12.34) |

Notes:
Vinyl Ether: UVR6105/pTHF 1:1.
OPIA/CQ 0.25/o.5 mole % based on moles of functional groups; 20 min irradiation; 37° C.; 418 nm filter; 11.6 mW/cm$^2$; sample size ≈ 11 mg;
NC = no reaction or reaction not completed.

TABLE 6B

VINYL ETHER/DIEPOXIDE/POLYOL PHOTOPOLYMERIZATIONS: SERIES 1B (ERL4206)

| No. | Vinyl Ether | Enthalpy (J/g) | Induction Time (sec) | Time to Max. (sec) | Conversion at Max (%) | Enthalpy (kcal/mole eq) |
|---|---|---|---|---|---|---|
| 17 | EGDVE | 338 | 213 | 542 | 48 | 5.17 |
| 18 | DEGDVE | 572 | 76 | 232 | 46 | 10.40 |
| 19 | TEGDVE | 577 (478) | 66 (16) | 144 (42) | 26 (17) | 11.97 (9.83) |
| 20 | HDDVE | 492 | 113 | 324 | 35 | 8.41 |
| 21 | CHDMDVE | NC | — | — | — | — |
| 22 | GVE | 289 (532) | 57 (11) | 123 (25) | 34 (32) | 2.79 (5.14) |
| 23 | POMDO | NC | — | — | — | — |
| 24 | BDVE | 497 (351) | 199 (42) | 286 (203) | 31 (29) | 11.11 (7.86) |

Notes:
Vinyl Ether: ERL 4206/pTHF 1:1.
OPIA/CQ 0.25/o.5 mole % based on moles of functional groups; 20 min irradiation; 37° C.; 418 nm filter; 11.6 mW/cm$^2$; sample size ≈ 11 mg;
NC = no reaction or reaction not completed.
With EDMAB runs in parentheses.

TABLE 6C

Vinyl Ether/Diepoxide/Polyol Photopolymerizations: series II (Preferred Reactants)

| | Reactions | | Ratio | Enthalpy (kcal/mol kg.) | | Enthalpy (sec) | | Induction Time (sec) | | Time to Max (%) | | Conv. At Max. | | Rat Const. | |
|---|---|---|---|---|---|---|---|---|---|---|---|---|---|---|---|
| No. | VE | Epoxide | V:E | w/o ED | w/ED | w/o ED | w/ED | w/o ED | w/ED | w/o ED | w/ED | w/o ED | w/ED | w/o ED | w/ED |
| 25 | TEGDVE | 6105/pTHF | 2:1 | 360 | 351 | 9.56 | 9.32 | 87 | 18 | −249 | 62 | 43 | 38 | 0.4 | 2.2 |
| 26 | | | 1:1 | 345 | 353 | 9.55 | 9.77 | 76 | 16 | 121 | 33 | 12 | 15 | 0.2 | 0.9 |
| 27 | | | 1:2 | 280 | 477 | 8.10 | 13.80 | 58 | 13 | 104 | 15 | 22 | 18 | 1.4 | 10.4 |
| 28 | GVE | 6105/pTHF | 2:1 | 170 | 66 | 3.13 | 1.22 | 75 | 15 | 142 | 38 | 22 | 24 | 0.5 | 5.3 |
| 29 | | | 1:1 | 270 | 320 | 5.84 | 6.92 | 60 | 14 | 102 | 24 | 19 | 22 | 0.7 | 11.0 |
| 30 | | | 1:2 | 147 | 315 | 3.67 | 7.89 | 122 | 11 | 396 | 22 | 43 | 21 | 0.6 | 8.6 |
| 31 | BDVE | 6105/pTHF | 2:1 | 401 | 332 | 11.60 | 9.60 | 278 | 22 | 400 | 38 | 28 | 29 | 1.7 | 29.0 |
| 32 | | | 1:1 | 351 | 418 | 10.33 | 12.34 | 233 | 23 | 376 | 47 | 53 | 35 | 2.2 | 36.0 |
| 33 | | | 1:2 | 198 | 422 | 5.96 | 12.70 | 163 | 28 | 233 | 42 | 32 | 26 | 3.3 | 18.6 |
| 34 | TEGDVE | 4206/pTHF | 2:1 | 61 | 507 | 1.33 | 11.05 | 344 | 22 | 800 | 114 | 62 | 43 | 0.2 | 1.0 |
| 35 | | | 1:1 | 577 | 478 | 11.87 | 9.83 | 66 | 16 | 144 | 42 | 26 | 17 | 0.5 | 0.9 |
| 36 | | | 1:2 | 548 | 400 | 10.61 | 7.75 | 58 | 12 | 127 | 15 | 27 | 18 | 1.2 | 8.3 |
| 37 | GVE | 4206/pTHF | 2:1 | 597 | 358 | 8.14 | 4.88 | 52 | 9 | 114 | 23 | 25 | 30 | 0 9 | 11.0 |
| 38 | | | 1:1 | 289 | 532 | 2.79 | 5.14 | 57 | 11 | 123 | 25 | 34 | 32 | 1.8 | 13.7 |
| 39 | | | 1:2 | 467 | 578 | 7.14 | 8.84 | 59 | 9 | 135 | 13 | 30 | 20 | 0.9 | 12.0 |
| 40 | BDVE | 4206/pTHF | 2:1 | 479 | 456 | 11.57 | 11.02 | 387 | 54 | 479 | 102 | 45 | 26 | 27.2 | 2.3 |
| 41 | | | 1:1 | 497 | 352 | 11.11 | 7.86 | 199 | 42 | 286 | 203 | 31 | 29 | 1.2 | 0.6 |
| 42 | | | 1:2 | 444 | 218 | 9.13 | 4.48 | 150 | 37 | 278 | 67 | 24 | 22 | 0.8 | 2.6 |

Note:
UVR 6105/pTHF 80/20 wt %; ERL 4206 pTHF 80/20 wt %; OPIA/CQ 0.25/0.5 mole % based on moles of functional groups; 37° C., 418 nm filter, 11.6 mW/cm$^2$; sample size ≈ 11 mg.
ED = EDMAB Still further, a substantial amount of vinyl ether is present in mixtures of vinyl ethers, SOCs, epoxides, polyols and the ternary photoinitiator system, which form photopolymerizable compositions of the present invention. In these mixtures, the vinyl ethers can provide a way to control the reactivity of the formulation during polymerization. By using an epoxide with a vinyl ether, the physical properties of the vinyl ether are improved. This vinyl ether-based composition is further improved by the addition of a polyol which increases the reaction rate of the epoxide. In addition, the low amount of shrinkage and possible expansion of SOCs during polymerization further adds benefit to the vinyl ether-based composition. While SOCs tend to retard the reaction rate somewhat, the benefits provided by them outweigh these disadvantages for certain applications, especially when an electron donor is used to promote the reaction. Still further, for a given level of SOCs, varying the amount of vinyl ether in the composition provides another way to control the reactivity and resultant physical properties of this vinyl ether/SOC/epoxide/polyol mixture. The photopolymerization of various vinyl ether/epoxide/polyol/SOC compositions is shown by the data in Tables 7A, 7B, and 7C. The data in these tables shows that reaction rates increased when an electron donor was used.

TABLE 7A

VINYL ETHER/DIEPOXIDE/POLYOL/TOSU PHOTOPOLYMERIZABLE COMPOSITIONS

| No. | DE/pTHF | VE | VE/EPOXY | TOSU | Wt. % | PI | PS | ED* |
|---|---|---|---|---|---|---|---|---|
| 43 | UVR6105 | TEGDVE | 1/1 | DEDPM | 30 | CD1012 | CQ | — |
| 44 | UVR6105 | TEGDVE | 2/1 | DEDPM | 30 | CD1012 | CQ | — |
| 45 | UVR6105 | TEGDVE | 1/1 | DEDPM | 30 | CD1012 | CQ | X |
| 46 | UVR6105 | TEGDVE | 2/1 | DEDPM | 30 | CD1012 | CQ | X |
| 47 | UVR6105 | TEGDVE | 1/1 | DECHE | 30 | OPIA | CQ | — |
| 48 | UVR6105 | TEGDVE | 2/1 | DECHE | 30 | OPIA | CQ | — |
| 49 | UVR6105 | TEGDVE | 1/1 | DECHE | 30 | OPIA | CQ | X |
| 50 | UVR6105 | TEGDVE | 2/1 | DECHE | 30 | OPIA | CQ | X |
| 51 | UVR6105 | TEGDVE | 1/2 | DECHE | 30 | OPIA | CQ | — |
| 52 | UVR6105 | TEGDVE | 1/2 | DECHE | 30 | OPIA | CQ | X |
| 53 | UVR6105 | TEGDVE | 1/1 | DM | 30 | RHO2074 | CQ | — |
| 54 | UVR6105 | TEGDVE | 1/1 | DM | 30 | RHO2074 | CQ | X |
| 55 | UVR6105 | GVE | 1/1 | DTM | 30 | CD1012 | CQ | — |
| 56 | UVR6105 | GVE | 1/1 | DTM | 30 | CD1012 | CQ | X |
| 57 | UVR6105 | GVE | 1/1 | DEDPM | 30 | CD1012 | CQ | — |
| 57A | UVR6105 | GVE | 1/1 | DEDPM | 30 | CD1012 | CQ | Y |
| 58 | UVR6105 | GVE | 1/1 | DECHE | 30 | CD1012 | CQ | X |
| 59 | UVR6105 | GVE | 1/1 | DEDPM | 30 | RHO2074 | CQ | — |
| 60 | UVR6105 | GVE | 1/1 | DEDPM | 30 | RHO2074 | CQ | X |
| 61 | UVR6105 | BDVE | 1/1 | DTM | 30 | CD1012 | CQ | — |
| 62 | UVR6105 | BDVE | 1/1 | DTM | 30 | CD1012 | CQ | X |
| 63 | UVR6105 | BDVE | 1/1 | DEDPM | 30 | CD1012 | CQ | X |
| 64 | UVR6105 | BDVE | 1/1 | DECHE | 30 | CD1012 | CQ | — |
| 64A | UVR6105 | BDVE | 1/1 | DECHE | 30 | CD1012 | CQ | Y |
| 65 | UVR6105 | BDVE | 1/1 | DTM | 30 | RHO2074 | CQ | — |
| 66 | UVR6105 | BDVE | 1/1 | DTM | 30 | RHO2074 | CQ | X |
| 67 | ERL4206 | TEGDVE | 1/1 | DTM | 30 | CD1012 | CQ | — |
| 68 | ERL4206 | TEGDVE | 1/1 | DTM | 30 | CD1012 | CQ | X |
| 69 | ERL4206 | TEGDVE | 1/1 | DEDPM | 30 | CD1012 | CQ | X |
| 70 | ERL4206 | TEGDVE | 1/1 | DECHE | 30 | CD1012 | CQ | — |
| 70A | ERL4206 | TEGDVE | 1/1 | DECHE | 30 | CD1012 | CQ | Y |
| 71 | ERL4206 | GVE | 1/1 | DEDPM | 30 | CD1012 | CQ | — |
| 72 | ERL4206 | GVE | 1/1 | DEDPM | 30 | CD1012 | CQ | X |
| 73 | ERL4206 | GVE | 1/1 | DECHE | 30 | CD1012 | CQ | — |
| 74 | ERL4206 | GVE | 1/1 | DECHE | 30 | CD1012 | CQ | X |
| 75 | ERL4206 | BDVE | 1/1 | DTM | 30 | CD1012 | CQ | — |
| 76 | ERL4206 | BDVE | 1/1 | DTM | 30 | CD1012 | CQ | X |
| 77 | ERL4206 | BDVE | 1/1 | DEDPM | 30 | CD1012 | CQ | — |
| 78 | ERL4206 | BDVE | 1/1 | DECHE | 30 | CD1012 | CQ | X |
| 79 | RD2 | TEGDVE | 1/1 | DCHE | 5 | OPIA | CQ | — |
| 80 | RD2 | TEGDVE | 1/1 | DCHE | 5 | OPIA | CQ | X |

*X = Bis(diethylamino) benzophenone (BDEAB);
Y = Ethyl 4-(diethylamino) benzoate (EDMAB)

TABLE 7B

VINYL ETHER/DIEPOXIDE/POLYOL/TOSU PHOTOPOLYMERIZATION RESULTS

| No. | $\Delta H_{theory}$ (J/g) | $\Delta H_{exper}$ (J/g) | Reacted (%) | Ind. Time (sec) | Peak Max (sec) | $\Delta H_{exper}$ at Max. (%) | Rate con (l/min) | Comments (20 min irradiation) |
|---|---|---|---|---|---|---|---|---|
| 43 | 415 | 268 | 65 | 110 | 141 | 10 | 0.12 | |
| 44 | 411 | 303 | 74 | 119 | 233 | 34 | 0.49 | 0.49 |
| 45 | 415 | 303 | 73 | 23 | 44 | 11 | 0.32 | |
| 46 | 411 | 325 | 79 | 27 | 49 | 10 | 0.95 | |
| 47 | 510 | 264 | 52 | 127 | 202 | 16 | 0.27 | not quite complete |
| 48 | 507 | 295 | 58 | 135 | 212 | 17 | 0.25 | |
| 49 | 510 | 339 | 66 | 27 | 54 | 13 | 0.39 | |

TABLE 7B-continued

VINYL ETHER/DIEPOXIDE/POLYOL/TOSU PHOTOPOLYMERIZATION RESULTS

| No. | $\Delta H_{theory}$ (J/g) | $\Delta H_{exper}$ (J/g) | Reacted (%) | Ind. Time (sec) | Peak Max (sec) | $\Delta H_{exper}$ at Max. (%) | Rate con (l/min) | Comments (20 min irradiation) |
|---|---|---|---|---|---|---|---|---|
| 50 | 507 | 420 | 83 | 37 | 74 | 11 | 0.28 | |
| 51 | 510 | 275 | 54 | 37 | 106 | 19 | 0.98 | |
| 52 | 510 | 285 | 56 | 24 | 46 | 15 | 1.19 | |
| 53 | 435 | 66 | 15 | 219 | 489 | 43 | 0.35 | not complete |
| 54 | 435 | 203 | 47 | 20 | 100 | 23 | 0.55 | not quite complete |
| 55 | 672 | 135 | 20 | 157 | 431 | 40 | 0.27 | not complete |
| 56 | 672 | 253 | 38 | 27 | 97 | 23 | 0.51 | not quite complete |
| 57 | 671 | 217 | 32 | 82 | 129 | 16 | 0.35 | |
| 57A | 671 | 148 | 22 | 92 | 212 | 29 | 0.77 | not complete |
| 58 | 764 | 361 | 47 | 20 | 41 | 15 | 1.60 | |
| 59 | 672 | 159 | 24 | 26 | 155 | 13 | 0.20 | not complete |
| 60 | 672 | 262 | 39 | 26 | 55 | 13 | 0.33 | not quite complete |
| 61 | 392 | 76 | 19 | 164 | 789 | 53 | 0.45 | not complete |
| 62 | 392 | 302 | 77 | 96 | 193 | 31 | 1.40 | not quite complete |
| 63 | 395 | 331 | 84 | 33 | 60 | 26 | 26.40 | |
| 64 | 485 | 258 | 53 | 296 | 490 | 33 | 0.69 | not complete |
| 64A | 485 | 276 | 57 | 61 | 138 | 23 | 0.69 | not quite complete |
| 65 | 398 | 153 | 38 | 378 | 805 | 52 | 0.41 | not complete |
| 66 | 398 | 308 | 77 | 33 | 143 | 31 | 1.40 | |
| 67 | 540 | 240 | 45 | 155 | 280 | 23 | 0.30 | not complete |
| 68 | 540 | 317 | 59 | 24 | 59 | 18 | 1.04 | |
| 69 | 544 | 484 | 89 | 23 | 52 | 31 | 59.49 | |
| 70 | 635 | 404 | 64 | 105 | 184 | 21 | 0.42 | not quite complete |
| 70A | 635 | 277 | 44 | 52 | 110 | 16 | 0.37 | not complete |
| 71 | 866 | 413 | 48 | 108 | 161 | 16 | 0.50 | not quite complete |
| 72 | 866 | 483 | 56 | 22 | 46 | 19 | 2.41 | |
| 73 | 968 | 399 | 41 | 101 | 155 | 14 | 0.28 | not complete |
| 74 | 968 | 491 | 51 | 32 | 63 | 16 | 0.72 | |
| 75 | 498 | 307 | 62 | 279 | 631 | 48 | 0.58 | not complete |
| 76 | 498 | 389 | 78 | 29 | 101 | 35 | 1.91 | |
| 77 | 504 | 425 | 84 | 205 | 365 | 34 | 7.77 | |
| 78 | 590 | 512 | 87 | 34 | 47 | 19 | 33.46 | |
| 79 | 596 | 353 | 59 | 76 | 116 | 24 | 4.88 | |
| 80 | 596 | 371 | 62 | 22 | 47 | 16 | 2.43 | not quite complete |

TABLE 7C

VINYL/ETHER/DIEPOXIDE/POLYOL/TOSU PHOTOPOLYMERIZATE PRODUCTS

| No. | Wt. Loss (mg) | Description of Post PDSC Product |
|---|---|---|
| 43 | 0 | Clear, soft, tearable disk |
| 44 | 0 | Clear, rubbery, tearable disk |
| 45 | 0 | Clear, soft, easily punctured and scratched |
| 46 | 0 | Clear, easily punctured |
| 47 | 0.4 | Clear, hard, tough solid |
| 48 | 0 | Clear, soft solid, can be scratched and scraped |
| 49 | 0 | Clear, hard, resisted scratching, slightly tacky |
| 50 | 0 | Clear, hard, can be punctured and scraped |
| 51 | 0.2 | Clear, hard, indentable solid |
| 52 | 1.3 | Clear, hard, resisted scratching and puncture |
| 53 | 0 | Partial think skin on liquid surface |
| 54 | 0.1 | Clear soft gel |
| 55 | 1.0 | Skin on top, liquid beneath surface |
| 56 | 0.6 | Clear, hard, resisted scratching and puncture |
| 57 | 0.7 | Clear, flexible, tearable disk |
| 57A | 0.3 | Tack solid |
| 58 | 0.3 | Clear, hard, resisted scratching and puncture |
| 59 | 0.1 | Clear, elastomeric, easily torn and punctured |
| 60 | 0.2 | Clear, elastomeric, easily torn and punctured |
| 61 | 0.4 | Mostly liquid, little evidence of cure |
| 62 | 0 | Clear, elastomeric, tacky surface, torn and punctured easily |
| 63 | 0 | Clear, flexible, easily torn and punctured |
| 64 | 0 | Clear, elastomeric, tacky surface, resisted tearing and puncture |
| 64A | 0 | Elastomeric solid |
| 65 | 0.3 | Clear, skin on surface, liquid beneath |
| 66 | 0 | Clear, soft gel |
| 67 | 0 | Elastomeric, tacky, easily punctured and torn |
| 68 | 0.4 | Clear, elastomeric, easily punctured and torn |
| 69 | 0 | Light brown hard elastomer, could be scratched and punctured |
| 70 | 0.9 | Very hard, clear, resisted scratching |
| 70A | 0 | Hard, resisted scratching |
| 71 | 0.6 | Clear, hard, resisted scratching and puncture |
| 72 | 0 | Clear, hard, tough elastomer, resisted scratching and puncture |
| 73 | — | Hard, tacky surface, resisted puncture |
| 74 | — | — |
| 75 | 0.1 | Clear, thin skin, liquid beneath surface |
| 76 | 0.7 | Clear, thick soft skin, liquid beneath surface |
| 77 | 0.4 | Brown, soft gel, liquid at surface |
| 78 | 0 | Brown center, amber solid, soft, easily torn and punctured |
| 79 | 0 | Soft, tearable solid |
| 80 | 0.1 | Soft, tearable solid |

The photopolymerizable compositions of the present invention, especially those containing a spiroorthocarbonate, are particularly useful as dental restorative materials, with the reaction product forming a matrix in which nonreactive dental fillers may be dispersed. More specically, a matrix is created from a cationic initiated reaction product of the various components of the polymerizable composition, and a dental filler material is dispersed in the matrix in an amount of between about 10 to 90% by weight based on the total weight of the dental restorative material.

In dental applications, in general, increasing amounts of spiroorthocarbonates in the reaction mixture cause decreasing shrinkage of the polymerizable composition. Although vinyl ether is still used in a substantial amount, high loadings of spiroorthocarbonates are desirable in the reaction mixtures of the present invention that are used as dental composites. When used as dental materials suitable ratios of the epoxy/hydroxyl-containing material to the SOCs range from 90:10 to 40:60 wt % and more preferably from 80:20 to 50:50 wt %. Still further, the present invention provides a system for curing polymerizable compositions in an acceptable time frame and to sufficient depth using visible light source equipment already available in dental offices. The components of the photopolymerizable composition are present in amounts sufficient to provide cure of the composition by exposure to visible light to a cure depth of at least about 1 mm.

The unique dental restorative materials of the present invention may be filled or unfilled and include dental materials such as direct aesthetic restorative materials (e.g., anterior and posterior restoratives), adhesives and primers for oral hard tissues, sealants, veneers, cavity liners, orthodontic bracket adhesives for use with any type of bracket (such as metal, plastic and ceramic), crown and bridge cements, prostheses, artificial crowns, artificial teeth, dentures, and the like. These dental materials are used in the mouth and may be disposed adjacent to natural teeth. The phrase "disposed adjacent to" as used herein will refer to the placing of a dental material in temporary or permanent bonded (e.g., adhesive) or touching (e.g., occlusal or proximal) contact with a natural tooth. The term "composite" as used herein will refer to a filled dental material. The term "adhesive" as used herein will refer to a dental material used for binding two substrates. The term "restorative" as used herein will refer to a composite which is polymerized after it is disposed adjacent to a tooth or in direct contact with an adhesive or liner which is adjacent to a tooth. The term "prosthesis" as used herein will refer to a composite which is shaped and polymerized for its final use (e.g., as a crown, bridge, veneer, inlay, onlay or the like) before it is disposed adjacent to a tooth. The term "sealant" as used herein will refer to a lightly filled composite or to an unfilled dental material which is cured after it is disposed adjacent to a tooth. "Polymerizable," as used herein, refers to curing or hardening the dental material, e.g., by free-radical, ionic or mixed reaction mechanisms.

Polymerization of vinyl ether-based reaction mixtures is initiated by adding suitable amounts of the ternary photoinitiator system and activating the initiator by exposure to a suitable light source. As one example, the following elements are combined with the reactants: (a) photoinitiator comprising (4-octyloxyphenyl)phenyl-iodonium hexafluoroantimonate at a concentration level of 1 wt. percent; (b) the photosensitizer viz., camphorquinone, concentration level of 0.5 wt. percent; and (c) ethyl 4-dimethylaminobenzoate at 0.1 wt. percent. The reactants and the photoinitiator system components are then mixed by a suitable mixer to form a homogenized mixture. Following mixing, the photopolymerizable formulation is light activated by exposure to a light source such as a XL-3000 dental curing light (3M Co.).

The photopolymerizable compositions of the present invention have utility as adhesives, composites and in other applications. Notably, the lack of volume contraction and, in some instances, a slight expansion during polymerization make the copolymer compositions particularly useful in dental applications, such as for dental fillings, precision castings, and strain-free composite matrix resins.

Filler particles can optionally be blended with the alicyclic spiroorthocarbonate and multifinctional copolymer composition to form a composite resin matrix for dental applications. The filler particles can be made of any suitable material but typically are inorganic in nature. Among the properties to be considered in selecting a filler are desired filler volume level, particle size, particle size distribution, index of refraction, radiopacity and hardness. Silicone dioxide is one example of a suitable filler. The filler particles can be produced by grinding or milling a material such as quartz or glass to an acceptable size, such as from 0.02 $\mu$m to 100 $\mu$m. A range of particles sizes is typically used to increase the amount of loading of filler material in the resin matrix. The amount of filler which can be added to the copolymer composition is dependent upon the total surface area of the filler particles. If colloidal size particles in the range of 0.02 to 0.04 $\mu$m are used, addition of as little as 5% by weight of the particles will be sufficient to modify the viscosity of the copolymer. Desirably, the filler can be present in an amount of between 20% and 80% by weight.

In order to increase the strength of the composite, a coupling agent can be used to increase the bonding strength between the filler particles and the polymerizable resin. Usually, when a coupling agent is used, it is used to treat the surface of the filler particles. This enhanced bonding can improve the physical and mechanical properties of the composite and can provide hydrolytic stability by preventing water from penetrating along the interface between the copolymer and the filler.

A coupling agent should be chosen which is compatible with the copolymer and filler and will not significantly contribute to shrinkage of the composite during polymerization. Preferably, the coupling agent does not inhibit cationic curing. Organosilanes are generally suitable coupling agents. Other examples of coupling agents include gamma-methacryloxypropyltrimethoxysilane, beta-(3,4-epoxycyclohexyl)ethyl-trimethoxysilane, gamma-glycidoxypropyltri-methoxysilane, and the like. Preferably, 3-glycidoxypropyltrimethoxysilane is used as a coupling agent when silicone dioxide is used as the filler material.

The photopolymerizable compositions of the invention are sensitive throughout the visible spectral region, and can photocure rapidly in the absence of heat, and in fact, they can cure at or below body temperature, to polymers having desirable properties. For purposes of the present invention, visible light is defined as light having a wavelength of between about 400 and 700 nanometers. The photopolymerization of the compositions of the invention occurs on exposure of the compositions to any source of radiation emitting actinic radiation within the visible spectral region at the wavelength of absorption of the photosensitizer. Exposures may be from less than about 1 second to 10 minutes or more, depending upon the amounts and particular components of the compositions utilized and depending upon the radiation source and distance from the source and the thickness of the composition to be cured. The compositions of the invention are typically one-part, stable compositions having very good shelf life and good thermal stability.

Still further, the polymerizable compositions of the present invention are capable of rapidly undergoing photoinitiated polymerization with less volume shrinkage and yielding polymers with less stress than conventional compositions so that they are more desirable for use as dental materials, such as for sealing cracks and fixtures in tooth structures and tooth restoratives. These compositions possess the mechanical and physical properties necessary for use as a composite material, including as a dental material matrix. In addition, these polymerizable compositions are capable of forming chemical bonds with substrates in a multifunctional group for use as an adhesive. This adhesive can be a cationically photoinitiated adhesive that is compatible with a cationically photoinitiated dental material system so as to obtain reduced shrinkage and enhanced bond strength when adhesive bonding low stress dental restorative materials to dentin and enamel substrates. In addition, these compositions can be cationically photopolymerized by visible light irradiation.

In certain applications, the use of a filler may be appropriate. The choice of filler affects important properties of the composite such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. Vinyl ether compositions of the invention, either alone or in admixture with diluent monomer, can be prepared with refractive indices which approach or approximate the refractive indices of fillers such as quartz (refractive index 1.55), submicron silica (1.46), and 5.5:1 mole ratio $SiO_2:ZrO_2$ non-vitreous microparticles (1.54). In this way the appearance of the dental material can, if desired, be made to closely approximate the appearance of natural dentition.

Radiopacity is a measurement of the ability of the composite to be detected by x-ray examination. Frequently a radiopaque composite will be desirable, for instance, to enable the dentist to determine whether or not a filling remains sound. Under other circumstances a non-radiopaque composite may be desirable.

The amount of filler which is incorporated into the composite (referred to herein as the "loading level" and expressed as a weight percent based on the total weight of the dental material) will vary depending on the type of filler, the vinyl ether resin and other components of the composition, and the end use of the composite.

For certain dental material applications (e.g., adhesives, composites, and sealants), the monomeric compositions of the invention can be lightly filled (e.g., having a loading level of less than about 40 weight percent) or unfilled. Preferably, the viscosity of the dental material is sufficiently low to allow its penetration into pits and fissures of occlusal tooth surfaces as well as into etched areas of enamel, thereby aiding in the retention of the dental material. In applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level of between about 70 and 90 weight percent is generally preferred.

Fillers may be selected from one or more of any material suitable for incorporation in compositions used for medical applications, such as fillers currently used in dental restorative compositions and the like. The filler is finely divided and preferably has a maximum particle diameter less than about 50 micrometers and an average particle diameter less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or non-radiopaque. Still further, the filler should not inhibit the cationic curing of the polymerizable composition.

Examples of suitable inorganic fillers are naturally-occurring or synthetic materials such as quartz, nitrides (e.g., silicon nitride), glasses derived from, for example, Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50," "130," "150" and "200" silicas sold by Degussa dn "Cab-O-Sil M5" silica sold by Cabot Corp.). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169. Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials.

The dental materials of the present invention can also contain suitable adjuvants such as accelerators, inhibitors, absorbers, stabilizers, pigments, dyes, viscosity modifiers, surface tension depressants and wetting aids, antioxidants, fluoride release agents, and other ingredients well known to those skilled in the art.

The amounts and types of each ingredient in the dental material should be adjusted to provide the desired physical and handling properties before and after cure. For example, the cure rate, cure stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

When the dental material is applied to a tooth, the tooth can optionally be pre-treated with a primer such as dentin or enamel adhesive by methods known to those skilled in the art.

From the foregoing, it will be seen that this invention is one well adapted to attain all the ends and objects hereinabove set forth together with other advantages that are obvious and inherent to the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

Having thus described the invention, what is claimed is:
1. A compound of the formula:

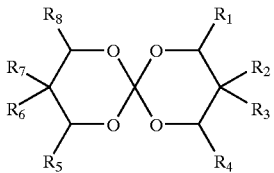

wherein
R₁–R₈ are independently selected from the group consisting of hydrogen; alkyl; aryl; substituted alkyl; substituted aryl; 6-oxabicyclo[3.1.0]hex-2-yl; 6-oxabicyclo[3.1.0]hex-3-yl; (6-oxabicyclo[3.1.0]hex-2-yl)methyl; (6-oxabicyclo[3.1.0]hex-3-yl)methyl; (6-oxabicyclo[3.1.0]hex-2-yl)methoxy; (6-oxabicyclo[3.1.0]hex-3-yl)methoxy; 7-oxabicyclo[4.1.0]hept-2-yl; 7-oxabicyclo[4.1.0]hept-3-yl; (7-oxabicyclo[4.1.0]hept-2-yl)methyl; (7-oxabicyclo[4.1.0]hept-3-yl)methyl; (7-oxabicyclo[4.1.0]hept-2-yl)methoxy; (7-oxabicyclo[4.1.0]hept-3-yl)methoxy; and —(CH₂)ₙ—O—(O=C)—R₉, where n=1 through 9 and R₉=H, alkyl, aryl, substituted alkyl and substituted aryl, or R₁•R₂, R₂•R₃, R₅•R₆, and R₆•R₇ are independently selected from the group consisting of —CH₂(CH₂)ₙCH₂— where n=3, 4, 5, and 6 and —CH₂-epoxy-(CH₂)ₙ—CH₂— where n=0, 1, and 2, and —O— so as to form an alicyclic ring or an oxirane ring between R₁ and R₂, R₂ and R₃, R₅ and R₆, or R₆ and R₇;

provided that the compound contains at least one epoxy or oxirane group and provided that R₁, R₄, R₅, and R₈ are hydrogen when R₂ is independently selected from the group consisting of 6-oxabicyclo[3.1.0]hex-2-yl, 6-oxabicyclo[3.1.0]hex-3-yl, (6-oxabicyclo[3.1.0]hex-2-yl)methyl, (6-oxabicyclo[3.1.0]hex-3-yl)methyl, (6-oxabicyclo[3.1.0]hex-2-yl)methoxy, (6-oxabicyclo[3.1.0]hex-3-yl)methoxy, 7-oxabicyclo[4.1.0]hept-2-yl, 7-oxabicyclo[4.1.0]hept-3-yl, (7-oxabicyclo[4.1.0]hept-2-yl)methyl, (7-oxabicyclo[4.1.0]hept-3-yl)methyl, (7-oxabicyclo[4.1.0]hept-2-yl)methoxy, (7-oxabicyclo[4.1.0]hept-3-yl)methoxy, and R₃, R₆, and R₇ are independently selected from the group consisting of hydrogen, alkyl, aryl, substituted alkyl, and substituted aryl;

R₁, R₄, R₅, and R₈ are hydrogen when R₂ and R₃ are independently selected from the group consisting of 6-oxabicyclo[3.1.0]hex-2-yl, 6-oxabicyclo[3.1.0]hex-3-yl, (6-oxabicyclo[3.1.0]hex-2-yl)methyl, (6-oxabicyclo[3.1.0]hex-3-yl)methyl, (6-oxabicyclo[3.1.0]hex-2-yl)methoxy, (6-oxabicyclo[3.1.0]hex-3-yl)methoxy, 7-oxabicyclo[4.1.0]hept-2-yl, 7-oxabicyclo[4.1.0]hept-3-yl, (7-oxabicyclo[4.1.0]hept-2-yl)methyl, (7-oxabicyclo[4.1.0]hept-3-yl)methyl, (7-oxabicyclo[4.1.0]hept-2-yl)methoxy, (7-oxabicyclo[4.1.0]hept-3-yl)methoxy, and R₃ and R₇ are independently selected from the group consisting of hydrogen, alkyl, aryl, substituted alkyl, and substituted aryl;

R₃, R₄, R₅, R₆, R₇, and R₈ are independently selected from the group consisting of the group consisting of hydrogen, alkyl, aryl, substituted alkyl, and substituted aryl, when R₁•R₂=—O— so as to form an oxirane ring between R₁ and R₂;

R₃, R₄, R₇, and R₈ are independently selected from the group consisting of the group consisting of hydrogen, alkyl, aryl, substituted alkyl, and substituted aryl, when R₁•R₂ and R₅•R₆=—O— so as to form an oxirane ring between R₁ and R₂ and between R₅ and R₆;

R₁, R₄, R₅, and R₈ are hydrogen when R₂ and R₃ are ethyl and R₆•R₇ are —CH₂-epoxy-(CH₂)ₙ—CH₂— where n=1 and 2 so as to form an alicyclic ring between R₆ and R₇; and R₁, R₄, R₅, and R₈ are hydrogen when R₂•R₃ and R₆•R₇ are —CH₂-epoxy-(CH₂)ₙ—CH₂— where n=1 and 2 so as to form an alicyclic ring between R₂ and R₃ and R₆ and R₇.

2. The compound of claim 1, wherein said compound is selected from the group consisting of 5,5-diethyl-19-oxadispiro[1,3-dioxane-2,2'-1,3-dioxane-5'4"-bicyclo[4.1.0]heptane], 7,26-dioxatrispiro[bicyclo[4.1.0]heptane-4,5'-1,3-dioxane-2'2"-1,3-dioxane-5",4"bicyclo[4.1.0]heptane], 5-5-diethyl-18-oxadispiro[1,3-dioxane-2,2'-1,3-dioxane-5'3"-bicyclo[3.1.0]hexane], and 6,24-dioxatrispiro[bicyclo[3.1.0]hexane-3,5'-1,3-dioxane-2'2"-1,3-dioxane-5"3"'-bicyclo[3.1.0]hexane], 3,3-diethyl-1,5,7,11-tetraoxa-9-[(6-oxabicyclo[3.1.0]hex-3-yl)methoxy]spiro[5.5]undecane, 3,9-bis[(6-oxabicyclo[3.1.0]hex-3-yl)methoxy]-3-ethyl-1,5,7,11-tetraoxaspiro[5.5]undecane, 3,3-diethyl-1,5,7,11-tetraoxa-9-[(6-oxabicyclo[3.1.0]hex-2-yl)methoxy]spiro[5.5]undecane, 3,9-bis[(6-oxabicyclo[3.1.0]hex-2-yl)methoxy]-3-ethyl-1,5,7,11-tetraoxaspiro[5.5]undecane, 3,3-diethyl-1,5,7,11-tetraoxa-9-[(6-oxabicyclo[3.1.0]hex-3-yl)methyl]spiro[5.5]undecane, 3,9-bis[(6-oxabicyclo[3.1.0]hex-2-yl)methyl]-3-ethyl-1,5,7,11-tetraoxaspiro[5.5]undecane, 3,3-diethyl 1,5,7,11-tetraoxa-9-[(6-oxabicyclo[3.1.0]hex-2-yl)methyl]spiro[5.5]undecane, 3,9-bis[(6-oxabicyclo[3.1.0]hex-2-yl)methyl]-3-ethyl-1,5,7,11-tetraoxaspiro[5.5]undecane, 3,3-diethyl-1,5,7,11-tetraoxa-9-(7-oxabicyclo[4.1.0]hept-3-yl)methyl]spiro[5.5]undecane, 3,9-bis(7-oxabicyclo[4.1.0]hept-3-yl)methyl]-3-ethyl-1,5,7,11-tetraoxaspiro[5.5]undecane, 3,3-diethyl-1,5,7,11-tetraoxa-9-(7-oxabicyclo[4.1.0]hept-2-yl)methyl]spiro[5.5]undecane, 3,9-bis(7-oxabicyclo[4.1.0]hept-2-yl)methyl]-3-ethyl-1,5,7,11-tetraoxaspiro[5.5]undecane, 3,3-diethyl-1,5,7,11-tetraoxa-9-(6-oxabicyclo[3.1.0]hex-3-yl)spiro[5.5]undecane, 3,9-bis(6-oxabicyclo[3.1.0]hex-3-yl)-3-ethyl-1,5,7,11-tetraoxaspiro[5.5]undecane, 3,3-diethyl-1,5,7,11-tetraoxa-9-(6-oxabicyclo[3.1.0]hex-2-yl)spiro[5.5]undecane, 3,9-bis(6-oxabicyclo[3.1.0]hex-2-yl)-3-ethyl-1,5,7,11-tetraoxaspiro[5.5]undecane, 3,9-bis(7-oxabicyclo[3.1.0]hex-3-yl)-3-ethyl-1,5,7,11-tetraoxaspiro[5.5]undecane, 3,3-diethyl-1,5,7,11-tetraoxa-9-(7-oxabicyclo[3.1.0]hex-3-yl)spiro[5.5]undecane, 3,9-bis(7-oxabicyclo[3.1.0]hex-2-yl)-3-ethyl-1,5,7,11-tetraoxaspiro[5.5]undecane, 3,3-diethyl-1,5,7,11-tetraoxa-9-(7-oxabicyclo[3.1.0]hex-2-yl)spiro[5.5]undecane, 2,4,7,9,11,14-hexaoxaspiro[bicyclo[4.1.0]heptane-3,3'bicyclo[4.1.0]heptane], 8,10,13-trioxaspiro[1,3-dioxane-2,3'-bicyclo[4.1.0]heptane], 5,12-dimethyl-2,4,7,9,11,14-hexaoxaspiro[bicyclo[4.1.0]heptane-3,3'bicyclo[4.1.0]heptane], 4,5,5,11-tetramethyl-8,10,13-trioxaspiro[1,3-dioxane-2,3'-bicyclo[4.1.0]heptane], and 5,5-dimethyl-8,10,13-trioxaspiro[1,3-dioxane-2,3'-bicyclo[4.1.0]heptane].

* * * * *

UNITED STATES PATENT AND TRADEMARK OFFICE
CERTIFICATE OF CORRECTION

PATENT NO. : 6,653,486 B2
DATED : November 25, 2003
INVENTOR(S) : Chappelow et al.

It is certified that error appears in the above-identified patent and that said Letters Patent is hereby corrected as shown below:

Column 4,
Line 19, delete "R4" and insert -- $R_4$ -- therefor.
Line 19, delete "R6" and insert -- $R_6$ -- therefor.

Column 5,
Line 45, delete "[5.5S]undecane" and insert -- [5.5]undecane -- therefor.

Column 8,
Line 25, delete "$Ar_1$ and $Ar_2$" and insert -- $Ar^1$ and $Ar^2$ -- therefor.
Line 54, delete "phenyl4-" and insert -- phenyl-4- -- therefor.

Column 14,
Line 58, delete "VR-6216" and insert -- UVR-6216 -- therefor.

Column 20,
Line 19, delete "3,9-bis(p7-oxabicyclo[4.1.0]hept-3-yl)methyl]-3-" and insert -- 3,9-bis (7-oxabicyclo[4.1.0]hept-3-yl)methyl]-3- -- therefor.

Column 27,
Line 57, delete "Diacetate" and insert -- diacetate -- therefor.

Column 28,
Lines 10 and 28, delete "Hydroxymethyl" and insert -- hydroxymethyl -- therefor.
Line 28, delete "Adduct" and insert -- adduct -- therefor.

Column 30,
Line 42, delete "99°14 101°" and insert -- 99° - 101° -- therefor.
Line 50, delete "tetraoxaspiro[5.5)undecane" and insert -- tetraoxaspiro[5.5]undecane -- therefor.

Column 31,
Line 20, delete "against" and insert -- again -- therefor.
Line 56, delete "was concentrated using a rotary".
Line 57, delete "evaporator and dried under vacuum to give 21.2 g of oil".

Column 33,
Line 4, delete "()" and insert -- ( -- therefore.
Line 15, delete "(TEOC) The" and insert -- (TEOC). The -- therefor.
Line 21, delete "1.5%" and insert -- 15% -- therefor.

UNITED STATES PATENT AND TRADEMARK OFFICE
CERTIFICATE OF CORRECTION

PATENT NO.     : 6,653,486 B2
DATED          : November 25, 2003
INVENTOR(S)    : Chappelow et al.

It is certified that error appears in the above-identified patent and that said Letters Patent is hereby corrected as shown below:

Column 34,
Line 5, insert -- . -- after "propanediol".
Line 25, delete "1-Phenyl-1,3-propanediol".
Line 26, insert -- 1-Phenyl-1,3-propanediol -- before "dibutyltin".
Line 26, delete "." after "adduct".
Line 42, delete "containing".

Column 35,
Line 20, delete "$^{13}$H" and insert -- $^{13}$C -- therefor.
Line 24, delete "1250,1201" and insert -- 1250, 1201 -- therefor.
Line 24, delete "1078,1012" and insert -- 1078, 1012 -- therefor.
Line 25, delete "$C_{19}H_2O_4$" and insert -- $C_{19}H_{20}O_4$ -- therefor.
Line 27, delete "Diacetoxtmethyl" and insert -- Diacetoxymethyl -- therefore.
Line 58, delete "$_1$)" and insert -- $^1$) -- therefor.

Column 36,
Line 2, delete "3,9-diethyl-3,9-diethyl" and insert -- 3,9-diethyl -- therefor.
Line 37, delete "Diacetoxtmethyl" and insert -- Diacetoxymethyl -- therefor.

Column 37,
Line 60, delete "2,4dioxa" and insert -- 2,4-dioxa -- therefor.

Column 38,
Line 54, delete "was" and add -- were -- therefor.

Column 40,
Line 35, delete "a" and insert -- δ -- therefor.

Column 42,
Line 1, delete "$^1$-NMR" and insert -- $^1$H-NMR -- therefor.
Line 58, delete "alight" and insert -- a light -- therefor.
Line 60, delete "removal" and insert -- Removal -- therefor.

Column 44,
Line 60, delete "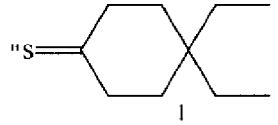" and insert 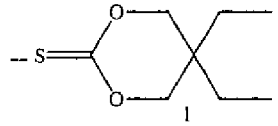 therefor.

UNITED STATES PATENT AND TRADEMARK OFFICE
CERTIFICATE OF CORRECTION

PATENT NO. : 6,653,486 B2
DATED : November 25, 2003
INVENTOR(S) : Chappelow et al.

It is certified that error appears in the above-identified patent and that said Letters Patent is hereby corrected as shown below:

<u>Column 46,</u>
Line 56, delete "28.53" and insert -- 128.53 -- therefor.
Line 61, delete "[3.1.0[hexane]" and insert -- [3.1.0]hexane] -- therefor.

<u>Column 47,</u>
Line 17, delete "Na2SO₄" and insert -- $Na_2SO_4$ -- therefor.

<u>Column 48,</u>
Line 52, delete "4-(dimethylamino)benzoate" and insert -- 4-(dimethylamino) benzoate -- therefor.
Line 61, delete "maxium" and insert -- maximum -- therefor.

<u>Column 50,</u>
Table 2, line 6, beginning DEGDVE, delete "539 33)" and insert -- 539 (33) -- therefor.

<u>Column 51,</u>
Line 51, delete "9.50" and insert -- 9.80 -- therefor.

<u>Columns 57, 58,</u>
Table 6C, line 3, delete "Rat Const." and insert -- Rate Const. -- therefor.
Table 6C, line 17, beginning No. 37, delete "0 9" and insert -- 0.9 -- therefor.

<u>Column 60,</u>
Table 7B, line 6, beginning No. 44, delete "0.49" under the Comments column heading.

<u>Column 61,</u>
Table 7B, line 35, beginning No. 77, delete "365" and insert -- 305 -- therefor.
Table 7C, line 15, beginning No. 53, delete "think" and insert -- thin -- therefor.
Line 20, beginning No. 57A, delete "Tack" and insert -- Tacky -- therefor.

<u>Column 63,</u>
Line 1, delete "specically" and insert -- specifically -- therefor.

<u>Column 64,</u>
Line 9, delete "multifinctional" and insert -- multifunctional -- therefor.

<u>Column 67</u>
Line 58, delete "consisting of the group".

UNITED STATES PATENT AND TRADEMARK OFFICE
CERTIFICATE OF CORRECTION

PATENT NO. : 6,653,486 B2
DATED : November 25, 2003
INVENTOR(S) : Chappelow et al.

It is certified that error appears in the above-identified patent and that said Letters Patent is hereby corrected as shown below:

<u>Column 68</u>
Line 55, delete "2,4,7,9,11,1" and insert -- 2,4,7,9,11,14 -- therefor.
Line 56, delete "4" before "-hexaoxapiro".

Signed and Sealed this

Thirty-first Day of May, 2005

JON W. DUDAS
*Director of the United States Patent and Trademark Office*